US012661151B2

(12) United States Patent
Mast et al.

(10) Patent No.: US 12,661,151 B2
(45) Date of Patent: Jun. 23, 2026

(54) SPINAL TETHERING DEVICES, SYSTEMS, AND METHODS

(71) Applicant: Highridge Medical, LLC, Westminster, CO (US)

(72) Inventors: Randall G. Mast, Denver, CO (US); Allison Christine Capote, Boulder, CO (US); Thomas J. Serra, Arvada, CO (US); John Spohn, Westminster, CO (US); Anup Gandhi, Superior, CO (US); Amy Claeson, Westminster, CO (US)

(73) Assignee: Highridge Medical, LLC, Westminster, CO (US)

( * ) Notice: Subject to any disclaimer, the term of this patent is extended or adjusted under 35 U.S.C. 154(b) by 27 days.

(21) Appl. No.: 18/784,607

(22) Filed: Jul. 25, 2024

(65) Prior Publication Data

US 2024/0374293 A1     Nov. 14, 2024

Related U.S. Application Data

(62) Division of application No. 17/565,253, filed on Dec. 29, 2021, now Pat. No. 12,048,460.

(Continued)

(51) Int. Cl.
*A61B 17/70*          (2006.01)
*A61B 17/68*          (2006.01)

(52) U.S. Cl.
CPC ...... *A61B 17/7022* (2013.01); *A61B 17/7032* (2013.01); *A61B 17/7044* (2013.01); *A61B 2017/681* (2013.01)

(58) Field of Classification Search
CPC ............ A61B 17/7022; A61B 17/7032; A61B 17/7044; A61B 2017/681

(Continued)

(56)          References Cited

U.S. PATENT DOCUMENTS 10,653,453 B2     5/2020   Ziemek et al.
10,905,474 B2     2/2021   Mast
(Continued)

OTHER PUBLICATIONS

International Search Report and Written Opinion for International (PCT) Patent Application No. PCT/US2021/065562, dated May 6, 2022 13 pages.

(Continued)

*Primary Examiner* — Eduardo C Robert
*Assistant Examiner* — David C Comstock

(57)          ABSTRACT

Various implants and surgical techniques for dynamic spinal tethering systems are discussed. In an example, a spinal tethering system can comprise a flexible elongate spinal tethering cord and a plurality of vertebral implants connecting the cord across at least four spinal levels. In this example, each vertebral implant of the plurality of vertebral implants can include a dynamic head coupling each vertebral implant to the cord. The dynamic head of each vertebral implant can be configured to share cord tension across multiple spinal levels by releasing a first tension generated at a first level between two vertebral implants of the plurality of vertebral implants to generate a second tension across two spinal levels between three vertebral implants of the plurality of vertebral implants, wherein the second tension is lower than the first tension.

20 Claims, 45 Drawing Sheets

Related U.S. Application Data

(60) Provisional application No. 63/138,678, filed on Jan. 18, 2021.

(58) Field of Classification Search
USPC ....... 606/246, 263, 254, 255, 257, 260, 264, 606/265, 268, 270, 271, 272, 301, 306, 606/308, 310, 319, 323, 329, 105
See application file for complete search history.

(56) References Cited

U.S. PATENT DOCUMENTS

| | | | |
|---|---|---|---|
| 10,939,941 | B2 | 3/2021 | Serra et al. |
| 12,048,460 | B2 | 7/2024 | Serra et al. |
| 2004/0220569 | A1 | 11/2004 | Wall et al. |
| 2005/0277920 | A1 | 12/2005 | Slivka |
| 2006/0217715 | A1 | 9/2006 | Serhan et al. |
| 2007/0191844 | A1 | 8/2007 | Carls et al. |
| 2008/0140122 | A1 | 6/2008 | Bethell |
| 2009/0292286 | A1 | 11/2009 | Carls et al. |
| 2010/0174219 | A1* | 7/2010 | Franke .................. A61F 5/0125 602/26 |
| 2016/0310170 | A1 | 10/2016 | Carls |
| 2018/0064469 | A1 | 3/2018 | Blakemore et al. |
| 2019/0262039 | A1 | 8/2019 | Gordon et al. |
| 2020/0078053 | A1* | 3/2020 | Sanders ............... A61B 17/863 |
| 2020/0330132 | A1 | 10/2020 | Grewal |
| 2022/0110662 | A1 | 4/2022 | LaColla |

OTHER PUBLICATIONS

International Preliminary Report on Patentability for International (PCT) Patent Application No. PCT/US2021/065562, dated Jul. 27, 2023 12 pages.

Official Action for U.S. Appl. No. 17/565,253, dated Dec. 22, 2022 6 pages, Restriction Requirement.

Official Action for U.S. Appl. No. 17/565,253, dated Jul. 21, 2023 14 pages.

Final Action for U.S. Appl. No. 17/565,253, dated Nov. 14, 2023 8 pages.

Notice of Allowance for U.S. Appl. No. 17/565,253, dated Mar. 6, 2024 8 pages.

* cited by examiner

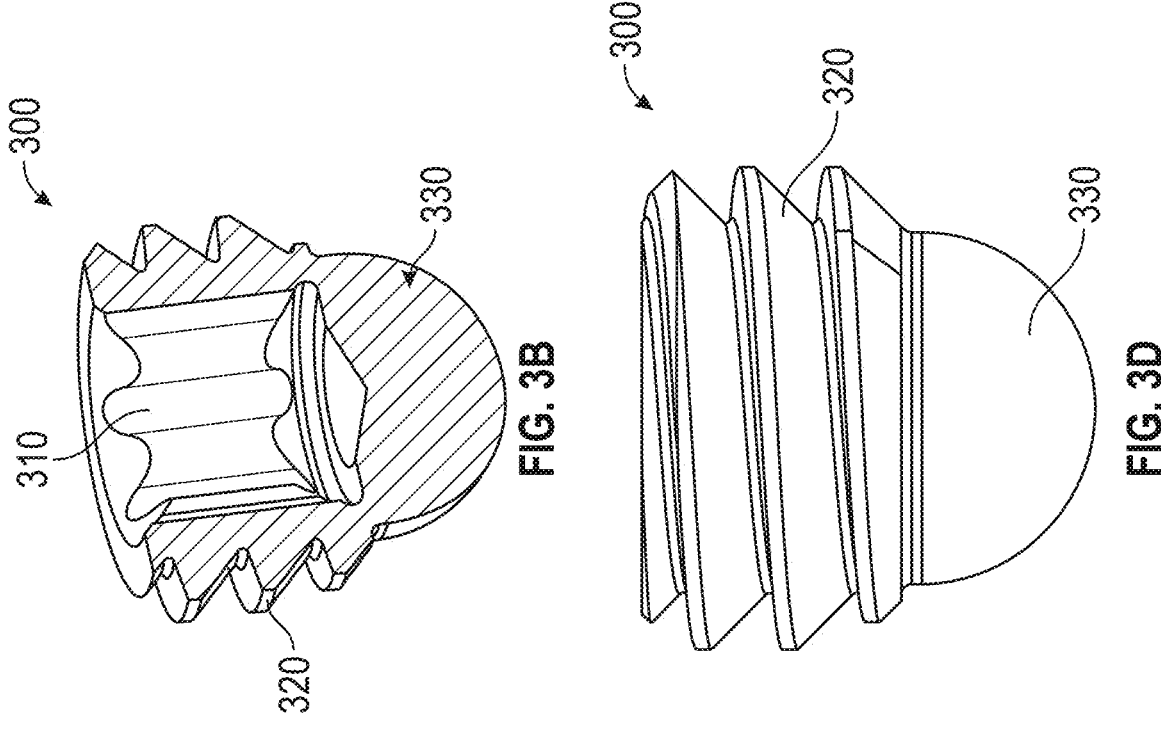
FIG. 3B
FIG. 3D
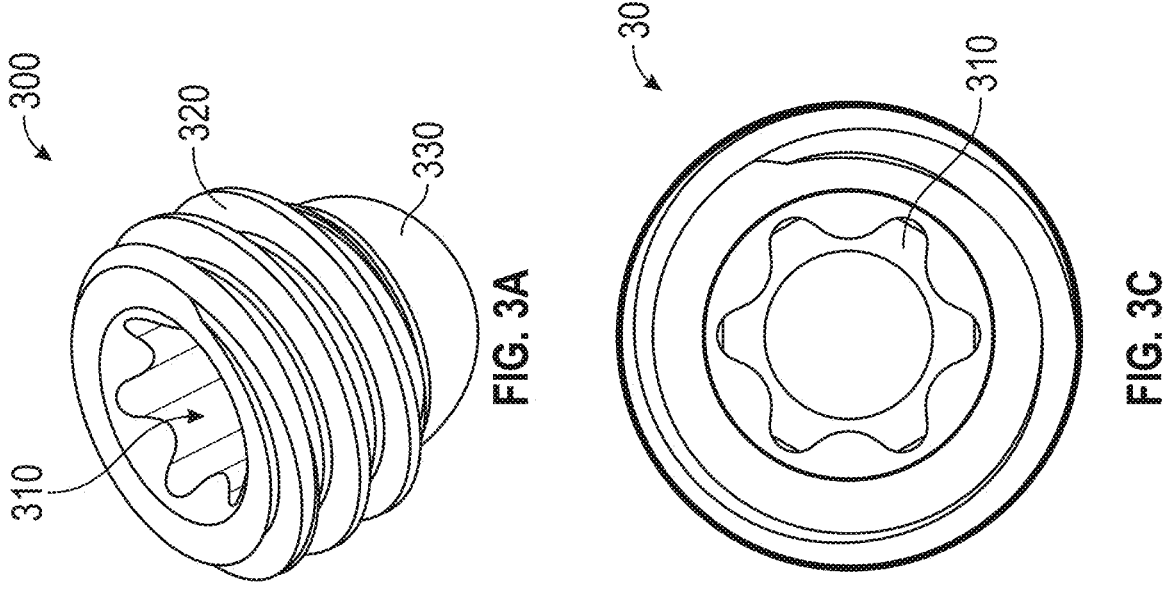
FIG. 3A
FIG. 3C

FIG. 8H            FIG. 8I

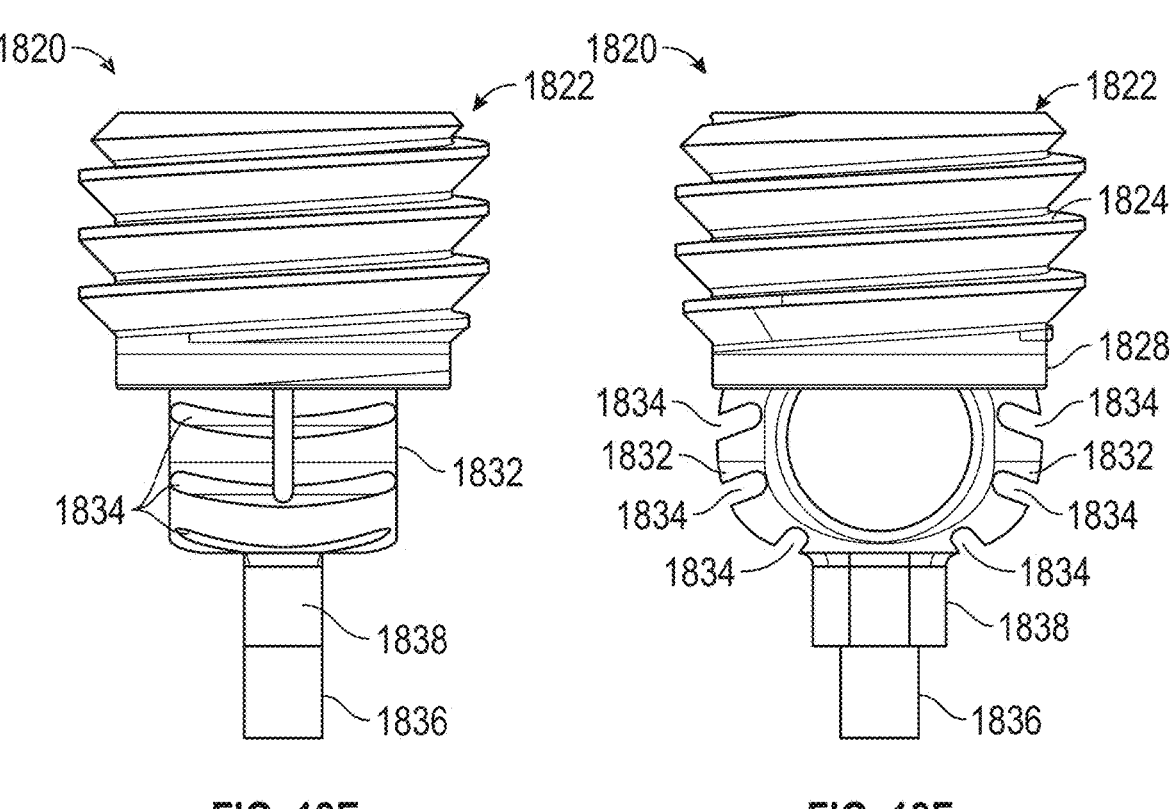
FIG. 18E
FIG. 18F
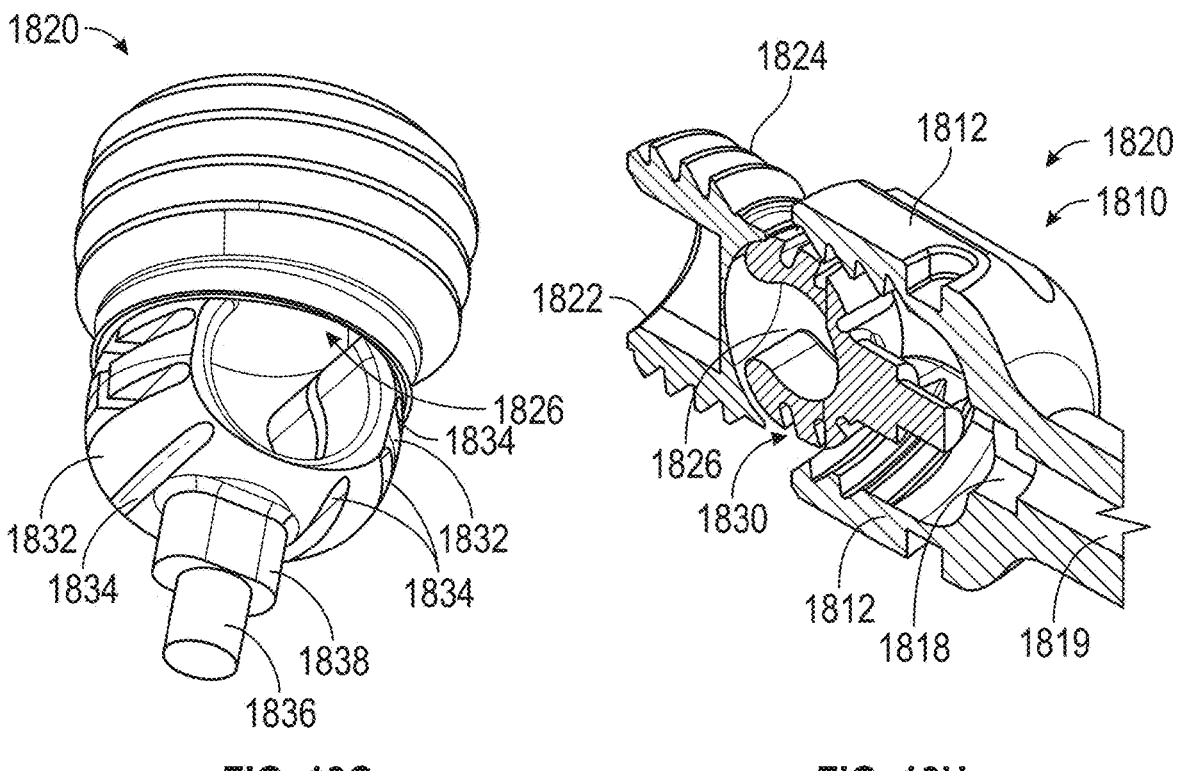
FIG. 18G
FIG. 18H

SPINAL TETHERING DEVICES, SYSTEMS, AND METHODS

CLAIM OF PRIORITY

This application is a divisional of U.S. patent application Ser. No. 17/565,253, filed on Dec. 29, 2021; which claims the benefit of U.S. Provisional Patent Application No. 63/138,678, filed on Jan. 18, 2021; all of the foregoing of each of which are incorporated by reference herein in their entirety.

FIELD OF THE DISCLOSURE

The present document relates to surgical techniques and devices for use in correcting spinal deformities, such as scoliosis. More specifically, this document discusses various vertebral implants for use in securing a flexible elongate member (e.g., tether or cord) between vertebral bodies and techniques for correction of spinal deformities using the disclosed implants.

BACKGROUND

Dynamic stabilization techniques, such as vertebral body tethering, are used in spinal treatment procedures for juveniles to permit enhanced mobility of the spine while also providing sufficient counter loading of a spinal curvature to effect treatment through bone growth modulation, particularly during times of rapid growth. Such dynamic stabilization systems may include fixed, uniaxial, or polyaxial bone anchors installed in adjacent or nearby vertebrae of the spine, various cord clamping devices, and a flexible cord secured to the bone anchors, with the cord tensioned between the bone anchors.

Current techniques and implants suffer from various deficiencies such as screw plow (migration), cord/tether failure, and difficulties in implantation among other things. The following disclosure discusses various implants and surgical procedures to address these and other short comings with traditional approaches to spinal tethering.

SUMMARY

The present inventors have recognized, among other things, that improving various aspects of spinal tethering systems can involve improvements such as implant (e.g., bone screw and/or anchor) revisions to mitigate screw migration, cord securing mechanisms (e.g., cord clamping) to reduce stress on the cord or reduce implantation time, construct strengthening to reduce or eliminate construct failure, and construct changes to prevent overcorrection, among others. Details of various concepts are provided below.

This overview is intended to provide an overview of subject matter of the present patent application. It is not intended to provide an exclusive or exhaustive explanation of the invention. The detailed description is included to provide further information about the present patent application.

BRIEF DESCRIPTION OF DRAWINGS

FIGS. 3A-D are various views of a spherical bottom set screw in accordance with the present disclosure.

FIGS. 8A-8J are various views of bone anchor concepts in accordance with the present disclosure.

FIGS. 18A-18H are various views of another cord clamping set screw in accordance with the present disclosure.

Figures 1A, 1B, 1C:
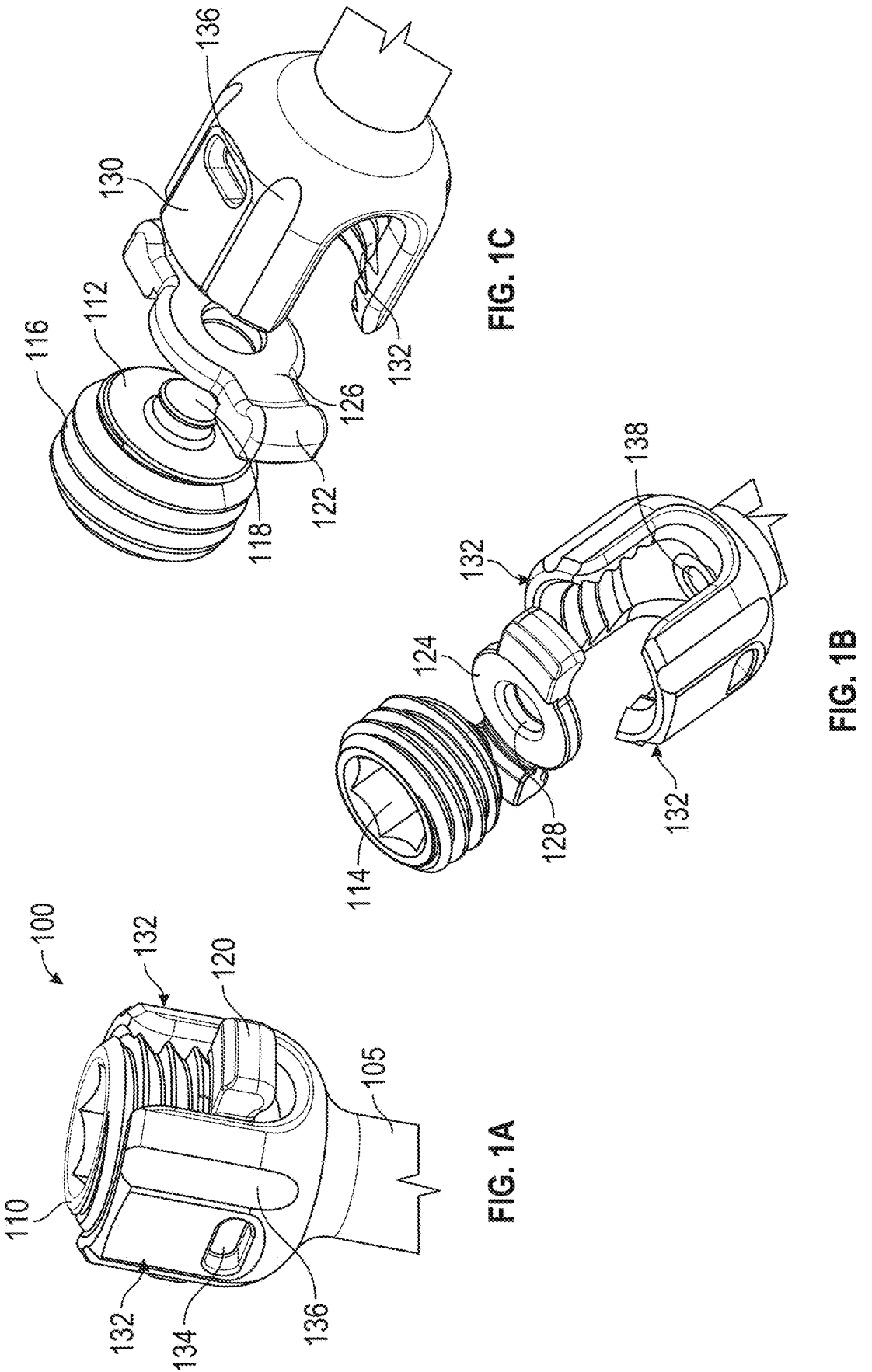
FIGS. 1A-1L are various views of a saddle insert cord washer and set screw combination in accordance with the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Exemplary embodiments will now be described more fully with reference to the accompanying drawings. The present disclosure provides details on concepts for improving various aspects of a spinal tethering system, such as a spinal tethering system detailed U.S. Pat. No. 10,653,453 titled "DYNAMIC STABILIZATION SYSTEMS AND ASSOCIATED METHODS", which is hereby incorporated by reference in its entirety. The improvements discussed also relate to aspects of the spinal tethering instruments discussed in U.S. Pat. No. 10,905,474 titled "SURGICAL CORD TENSIONING DEVICES, SYSTEMS, AND METHODS" and U.S. Pat. No. 10,939,941 titled "SURGICAL CORD TENSIONING DEVICES, SYSTEMS, AND METHODS", which are both hereby incorporated by reference in their entirety.

The following description discusses various implants used in a spinal tethering system, such as bone screws and anchors (staples). Most spinal tethering systems utilize bone screw designs from traditional spinal fixation systems targeting similar portions of the spine, such as fixed head pedicle screws. These traditional bone screws were originally designed to couple solid spinal rods between vertebral bodies, and can induce unwanted stress on a flexible cord or tether when used in a spinal tethering system. Spinal fixation systems often include fixed, uni-axial, and multi-axial bone screws, where the screw head (e.g., tulip or saddle) is fixed or allowed to move (uni-axial or multi-axial) in reference to the shaft of the bone screw. Bone screws from spinal fixation systems were typically designed to receive spinal fusion rods rather than flexible elongate members, such as a cord or tether. The improvements outlined below are discussed in reference to these commonly available bone screw designs. The anchors (staples) referenced below involve an implant that is designed to surround at least a portion of a bone screw and engage surrounding bone surface to distribute loads from the bone screw over a greater area of cortical bone. Again, improvements outlined below to anchors are discussed in reference to these anchor or staple designs.

Bone screw and anchor designs discussed below can provide numerous benefits over traditional pedicle screws for use in spinal tethering. The benefits can include providing a stronger construct, reducing screw plow (e.g., movement/migration of the screw in the vertebral body over time), enhancing cord clamping, reducing cord breakage, reducing surgical procedure steps (eliminate multiple steps for separate anchor and screw placement), and providing for dual cords to increase strength and provide redundancy.

Other devices discussed below include cord clamping mechanisms that deviate from use of set screws and typical tulip head pedicle screws. The cord clamping mechanisms discussed below provide benefits such as reducing stress points on the flexible cord, increasing holding strength, and allowing for controlled distribution of tension across multiple implant levels, among others. Additional benefits of each different implant is discussed below in reference to the illustrations of the specific designs.

FIGS. 1A-1L are various views of a saddle insert cord washer 120, 140, 150 and set screw 110 combination. FIG. 1A is an isometric view of an implant 100 including fixed tulip head (screw head) 130, a large cord washer 120, a set screw 110, and a screw shaft 105 extending from the screw head 130. The implant 100 is designed to enhance the strength of the grip on a cord extending through screw head 130 between the threaded sidewalls 132. The cord washers, large cord washer 120, medium cord washer 140 and small cord washer 150 (collectively referenced as cord washer 120, 140, 150 or simply cord washer 120), are designed to allow for dynamic cord slip at certain cord tension levels. Most of the embodiments are illustrated with the large cord washer 120, but any of the other cord washers can be used within the disclosed embodiments. The cord tension where slip occurs will be above the tension possible with a tensioning instrument during implantation, but below the cord's working tension limit (and well below the breaking strength of the cord). In some examples, the cord tension where slip occurs will be above the tension possible with the tensioning instrument and below the level of tension where screw plow occurs for a particular bone screw design. Dynamic constructs using cord slip are discussed below in more detail in reference to FIGS. 6A-6C.

In this example, the implant 100 includes a set screw 110. The set screw 110 can include a washer interface 112 that is a donut-shaped flat surface designed to mate with a similar surface, the set screw recess 124, on the superior side of the cord washer 120. The large surface area allows for distribution of the force generated by tightening the set screw 110 to push the cord washer 120 down on the cord. The washer interface 112 further includes a washer peg 118 extending from the center of the donut-nut shaped flat surface. The washer peg 118 is designed to engage a set screw bore 128 in the center of the cord washer 120. In some examples, the washer peg 118 includes in small ridge protruding from the distal end to generate a friction fit with the set screw bore 128 that keeps the cord washer 120 attached to set screw 110 during implantation. The set screw 110 also includes external threads 116 and a driver interface 114. The threads 116 engage with the threaded sidewalls 132 of the screw head 130. The driver interface 114 is designed to receive a torqueing instrument to enable tightening the set screw 110 into screw head 130. In this example, the driver interface 114 is a HEX shaped recess. In some examples, the implantation technique will include a torqueing instrument with a torque limiter set to put a pre-defined amount of pressure on the cord, which results in cord slip within a defined range of cord tension.

In this example, the implant 100 includes a tulip-head style screw head 130 with two opposing threaded sidewalls 132. The threaded sidewalls 132 include internal threads designed to receive the set screw 110. The screw head 130 also includes various implant instrument interfaces, such as instrument interface recesses 134 and instrument interface grooves 136. The instrument interface recesses 134 are oval shaped recesses on opposing sides of the screw head 130 within an outer surface of the threaded sidewalls 132. The instrument interface recesses 134 can be used to attach access instrumentation to the sides of screw head 130. The instrument interface grooves 136 are longitudinal grooves cut into each corner of the screw head 130. The instrument interface grooves 136 can be used to attached access instrumentations or instruments to implant the screw (torqueing instruments, such as a specialized screwdriver).

Figures 1D, 1E, 1F:
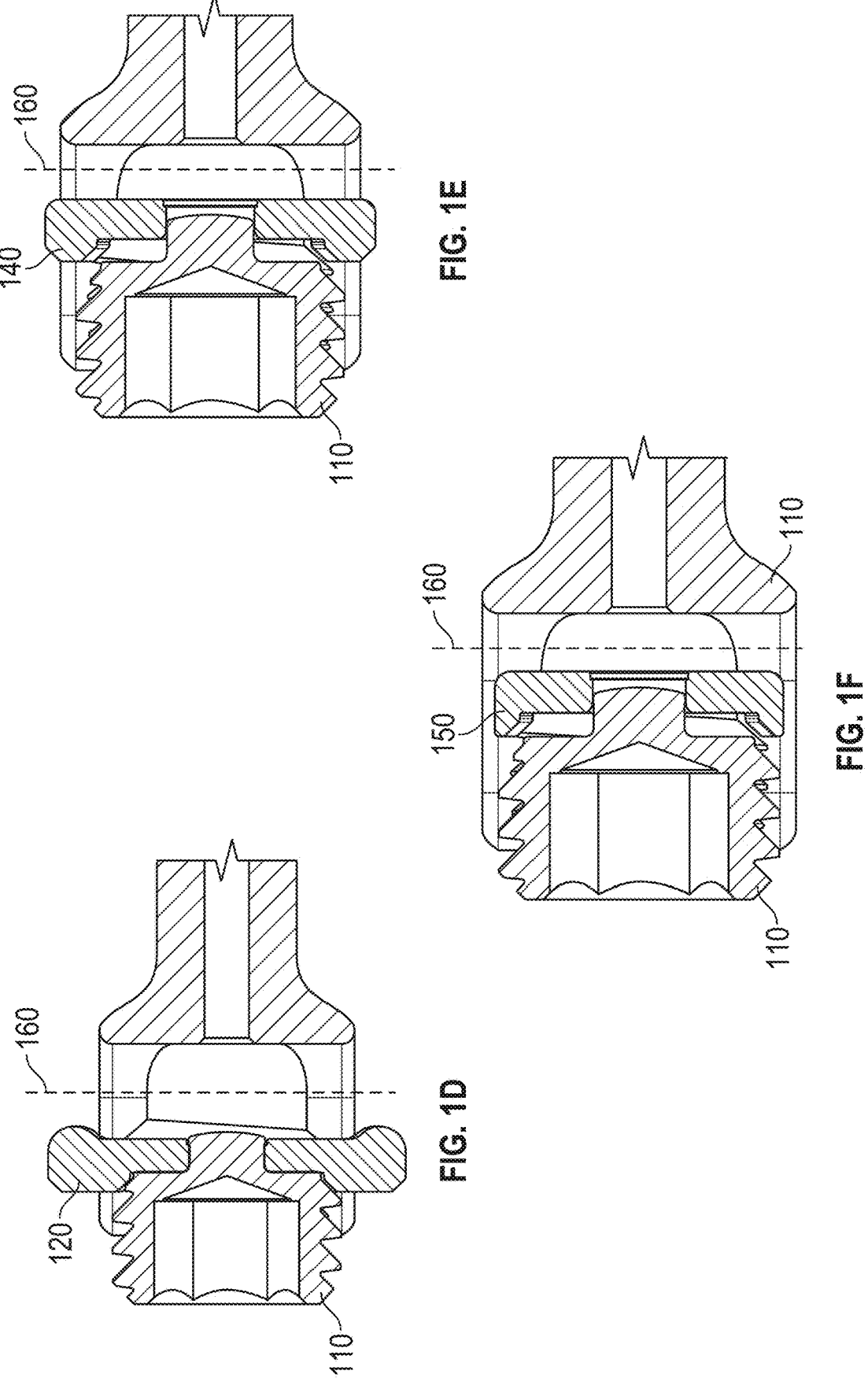
Figures 1G, 1H, 1I:
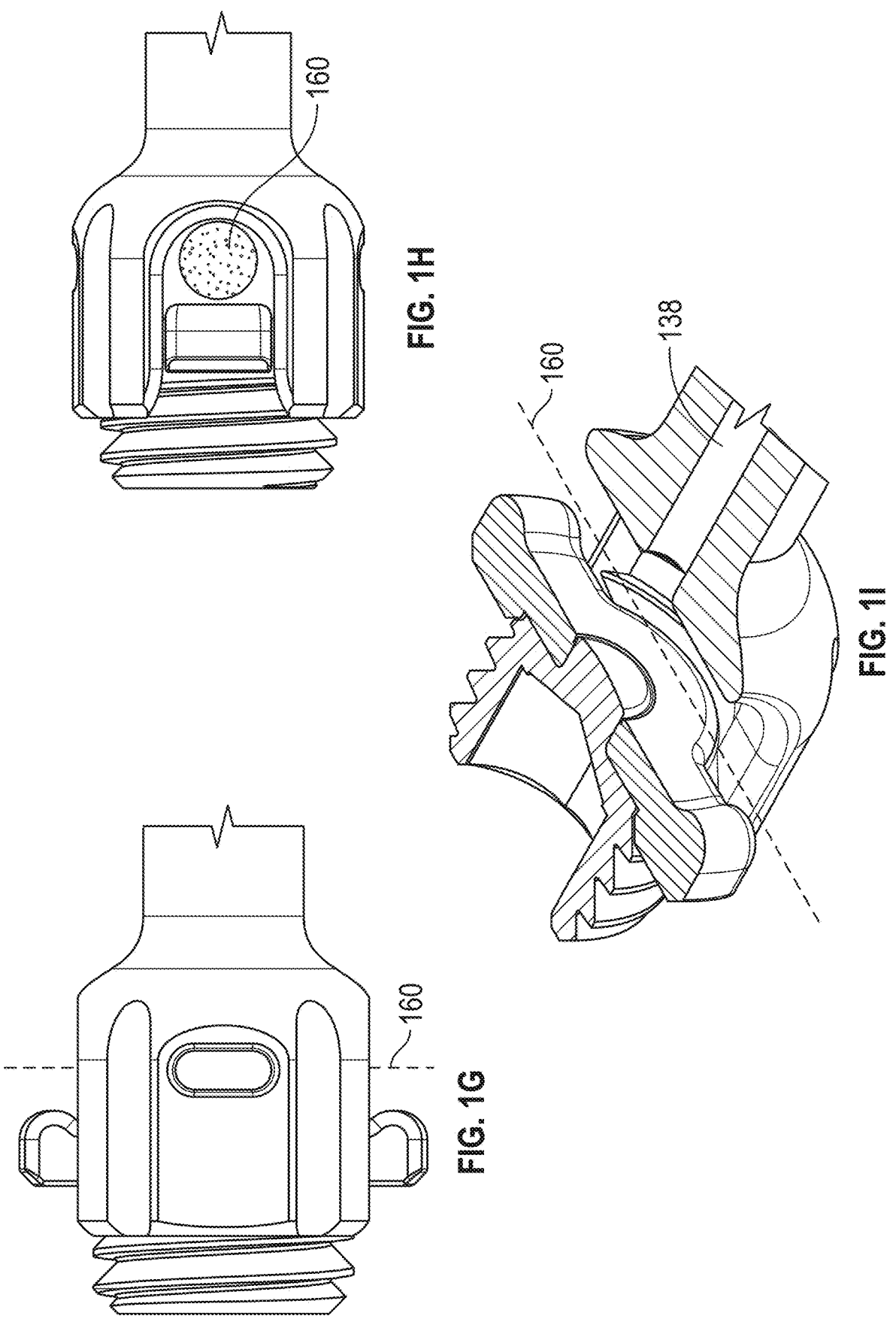

FIGS. 1D-1E are cross-sectional views of the implant 100 with each of the different cord washers. FIG. 1D is a cross-sectional view of the implant 100 with the large cord washer 120. The cross-sectional views include an illustration of the cord axis 160, which is representative of the path the tether or cord will take through the implant 100. FIG. 1D illustrates the set screw 110 fully engaged with the cord washer 120, while FIGS. 1E and 1F illustrate the set screw 110 just prior to full engagement. FIG. 1E is a cross-sectional view of the implant 100 with a medium cord washer 140, and FIG. 1F is a cross-sectional view of the implant 100 with a small cord washer 150.

Figures 1J, 1K, 1L:
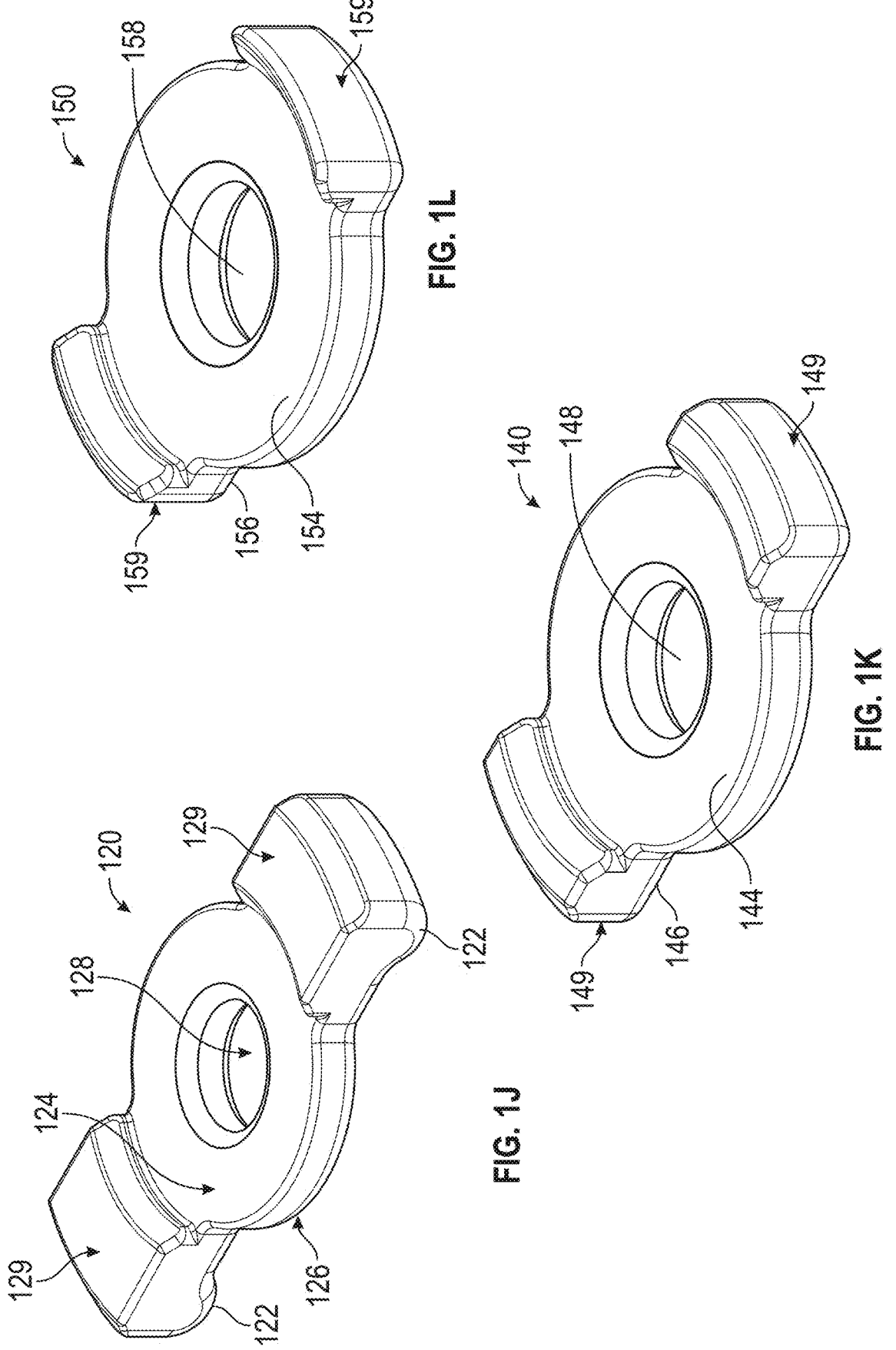
Figures 2A, 2B, 2C:
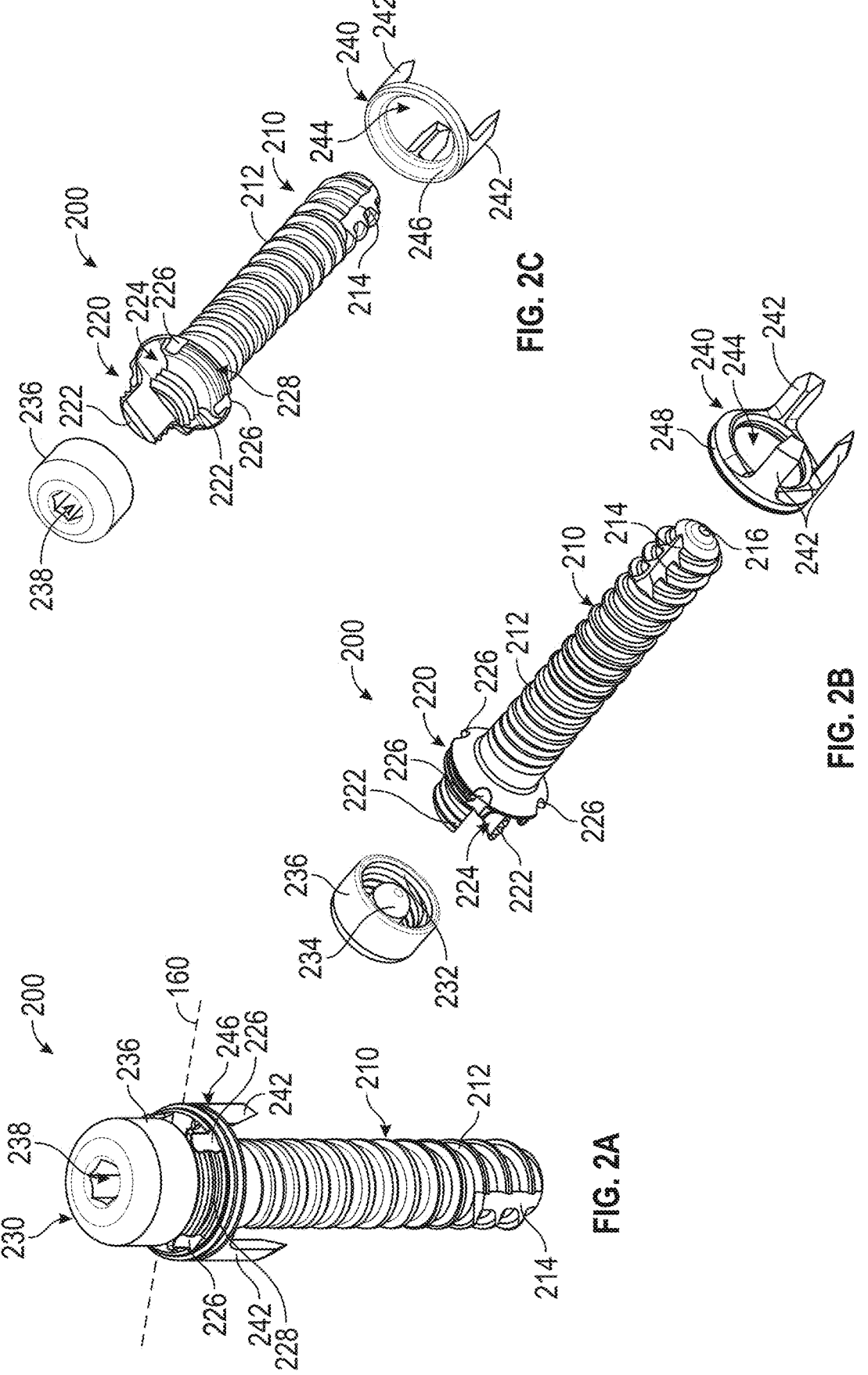
FIGS. 2A-2F are various views of a cap-style set screw and cord recess head bone screw in accordance with the present disclosure.
Figures 2D, 2E, 2F:
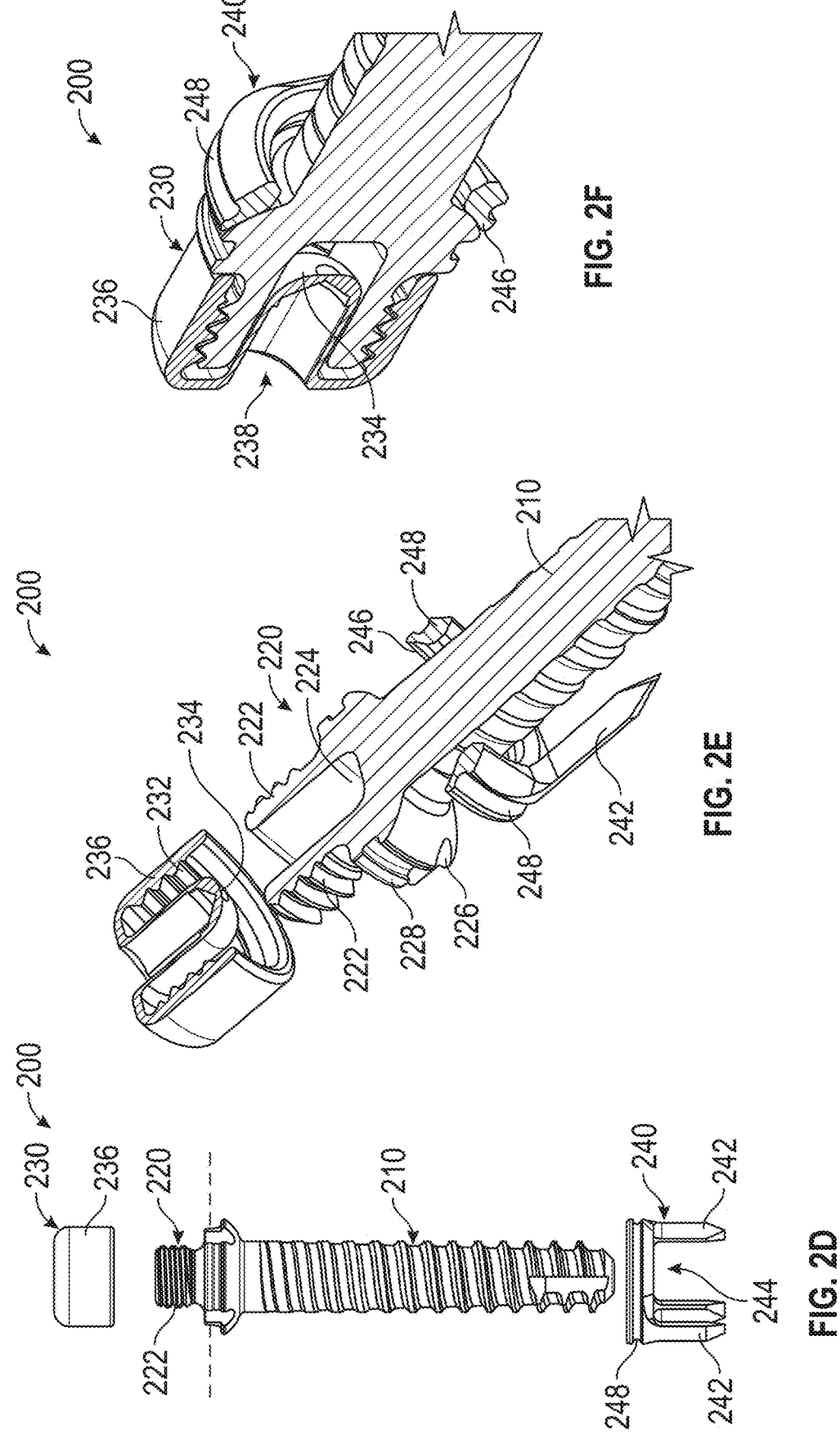

FIGS. 1J-1L are isometric views of the various sizes of cord washer in accordance with the present disclosure. FIG. 1J is an isometric view of the large cord washer 120. The large cord washer 120 includes cord grips 122 extending inferiorly from outer lower edges of the clamp extensions 129. The large cord washer 120 also includes a set screw recess 124 and a set screw bore 128 to receive the set screw 110. The large cord washer 120 includes an inferior surface designed to engage the cord when assembled into the implant 100. In this example, the cord grips 122 extend more inferiorly than the majority of the inferior surface 126, which creates additional friction on the cord to increase the level of tension prior to cord slip. FIG. 1K is an isometric view of the medium cord washer 140 that includes a similar structure as the other cord washers but does not include cord grips 122. The other difference with the medium cord washer 140 is mid-sized clamp extensions 149. The clamp extensions 149 increase the friction on the cord but create a lower cord slip tension as compared to the large cord washer 120. FIG. 1L is an isometric view of the small cord washer 150, which also has a similar structure to the other cord washers. The small cord washer 150 includes even smaller clamp extensions 159, which generate yet lower level of slip tension. In practice, each of the cord washers will generate a pre-defined level of slip tension on the cord when the set screw is torqued to a pre-defined level during implantation.

FIGS. 2A-2F are various views of an implant 200 including a cap-style set screw 230 and a cord recess within the head bone screw 210. The cap-style set screw 230 provide additional cord interface or gripping locations in comparison to a standard set screw. For example, the cap-style screw illustrated includes a central cord engagement member 234 and an outer cylindrical body that both operate to engage (e.g., compress) the cord within the cord recess 224 of the screw head 220. The implant 200 also includes features to enhance the strength of the implant, such as anchor 240 that can be implanted prior to implantation of bone screw 210.

In this example, the bone screw 210 includes a saddle or tulip style screw head 220 with integrated threaded arms 222 designed to receive the cap screw 230. The bone screw 210 includes screw threads 212 along the screw shaft. The screw threads 212 include cutting flutes 214 at the distal end of the screw shaft. The bone screw 210 can also include a fenestration 216 to enable implantation using K-wire guides. The screw head 220 includes threaded arms 222 separated by a cord recess 224. On the exterior of the screw head 220 there are features to assist with implantation including instrument interface grooves 226 and instrument interface threads 228.

The illustrated example implant 200 includes a cap screw 230 to secure a cord within the cord recess 224 of the bone screw 210. The cap screw 230 includes cap threads 232 on the internal sidewalls of a cylindrical body 236. The cap screw 230 also includes a central cord engagement member 234 extending inferiorly from the center inside the cylindrical body 236. Opposite the central cord engagement member 234 is a driver interface 238 recessed into the superior side of the cap screw 230. In this example, the central engagement member 234 includes a spherical tip, in other examples the tip could be a flat cylindrical surface or a spherical tip with a larger radius, among other shapes. The only limitation on the surface shape for the end of the central cord engagement member 234 is that it be symmetrical and allow for rotation of the cap screw 230 during tightening without adverse engagement with the cord.

Finally, implant 200 can include an anchor 240 to assist in preventing screw plow (migration) and strengthen the overall construct. In this example, the anchor 240 can include anchor spikes 242, a screw passage 244, a screw interface 246, and an instrument groove 248. The anchor 230 is illustrated with three anchor spikes 242 that each include a triangular shape body with a chisel tip. Other anchor spike configurations are envisioned, including two or four anchor spikes 242 as well as different body shapes. Different compatible anchor concepts are discussed below in reference to FIGS. 8A-8J and 9A-9F. In this example, the anchor 240 includes a chaffered internal screw interface 246 that is designed to mate with an external lower surface of the screw head 220 as illustrated in cross-section in FIG. 2F. In some examples, the screw interface 246 can be a concave radiused cylindrical ring that mates with a similar convex radiused surface on the inferior side of screw head 220 that allows for axial angulation of the bone screw 210 in reference to anchor 240 upon implantation. The instrument groove 248 provides a gripping location for an implantation instrument.

FIGS. 3A-D are various views of a spherical bottom set screw 300. The spherical bottom set screw 300 is designed distribute cord contact over a larger surface area and prevent points of failure while securing a cord within a bone screw housing. The spherical bottom can also allow for dynamic cord slip at tensions above a pre-defined value. The set screw 300 includes a driver interface 310, threads 320, and the spherical engagement surface 330. The set screw 300 is designed for use within any saddle or tulip style screw head.

FIGS. 4A-4D are various views of cap-style set screw and bone screw combinations that are alternatives to the design discussed above in reference to FIGS. 2A-2F. These examples include two different bone screws, implant 400A includes bone screw 410A that has threaded arms 422 integrated into the bone screw head 420A, while implant 400B includes bone screw 410B that utilizes an anchor 440B that includes threaded anchor arms 441 to receive cap screw 450.

In this example, implant 400A includes a bone screw 410A that is structured similarly to the bone screw 210 discussed above. The bone screw 410A includes screw head 420A that includes integrated threaded arms 422 with a cord recess 424 in between. The cord recess 424 is a smooth U-shaped space between the threaded arms 422. In this example, the cord recess 424 includes a bottom portion that aligns with a cord recess 435 cut out of a body of anchor 430. The screw head 420A also includes a driver interface 426 recessed into the center distal of the cord recess 424. The bone screw 410A also can include a fenestration 428.

Implant 400A also includes anchor 430 designed to encircle a distal portion of screw head 420A at the screw interface surface 446. In this example, the anchor 430 is designed to be implanted after the bone screw 410A, as the screw interface surface 446 includes a proximal angled surface that abuts a corresponding angled surface along the outer periphery of the base of the screw head 420A where threaded arms 422 adjoin. In these examples, the anchor 430 includes a series of anchor teeth 442 distributed around the circumference of the inferior side of the anchor 430. The anchor 430 also includes an instrument groove to assist in securing the anchor 430 in an implant instrument while the screw head 420A is inserted through the screw passage 434 of the anchor 430. The anchor 430 could be modified in accordance with other anchors discussed herein to include different anchor spikes or even accommodate dual bone screws.

Figures 4A, 4B, 4C, 4D:
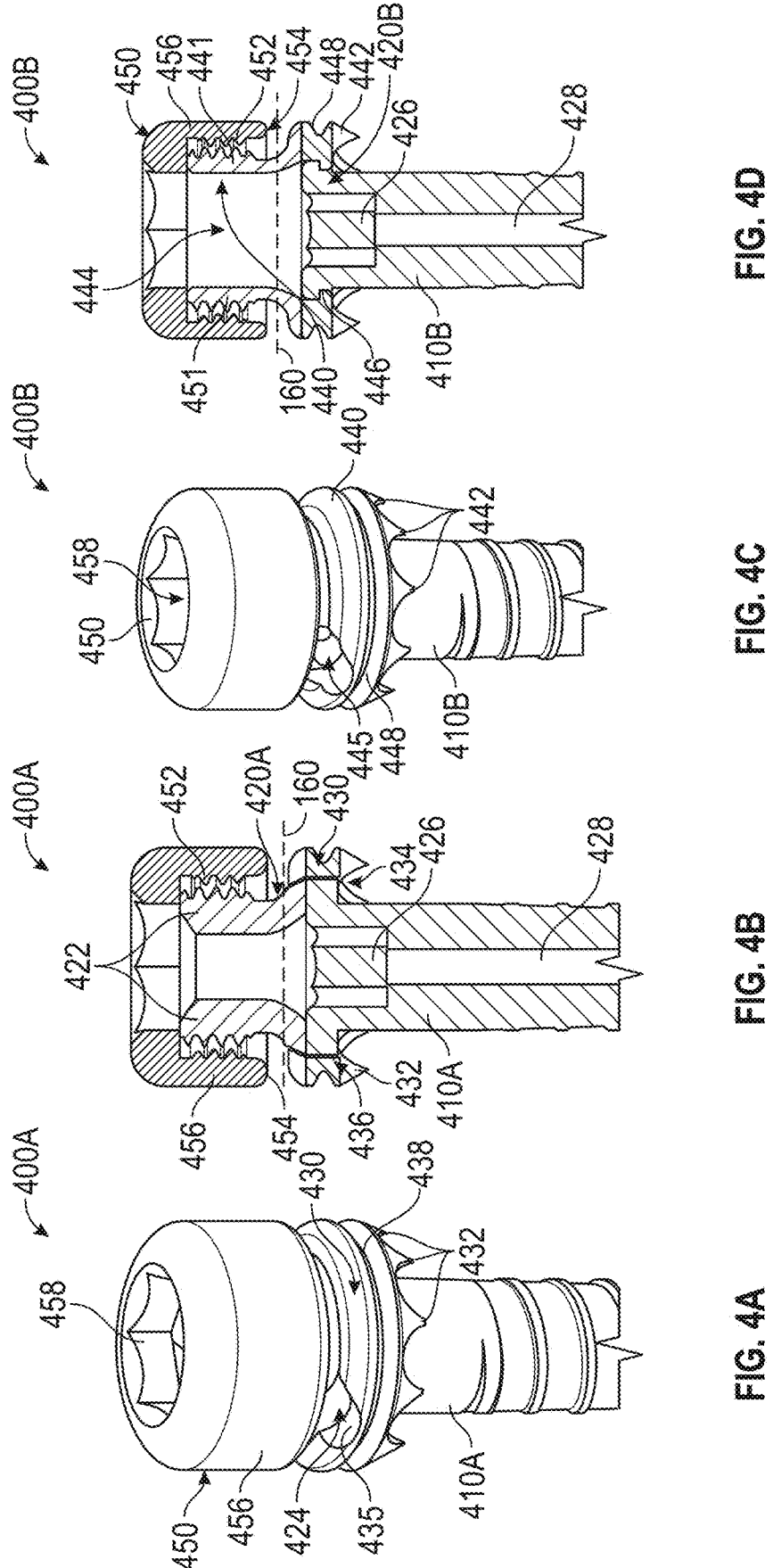
FIGS. 4A-4D are various views of cap-style set screw and bone screw combinations in accordance with the present disclosure.
Figures 5A, 5B, 5C:
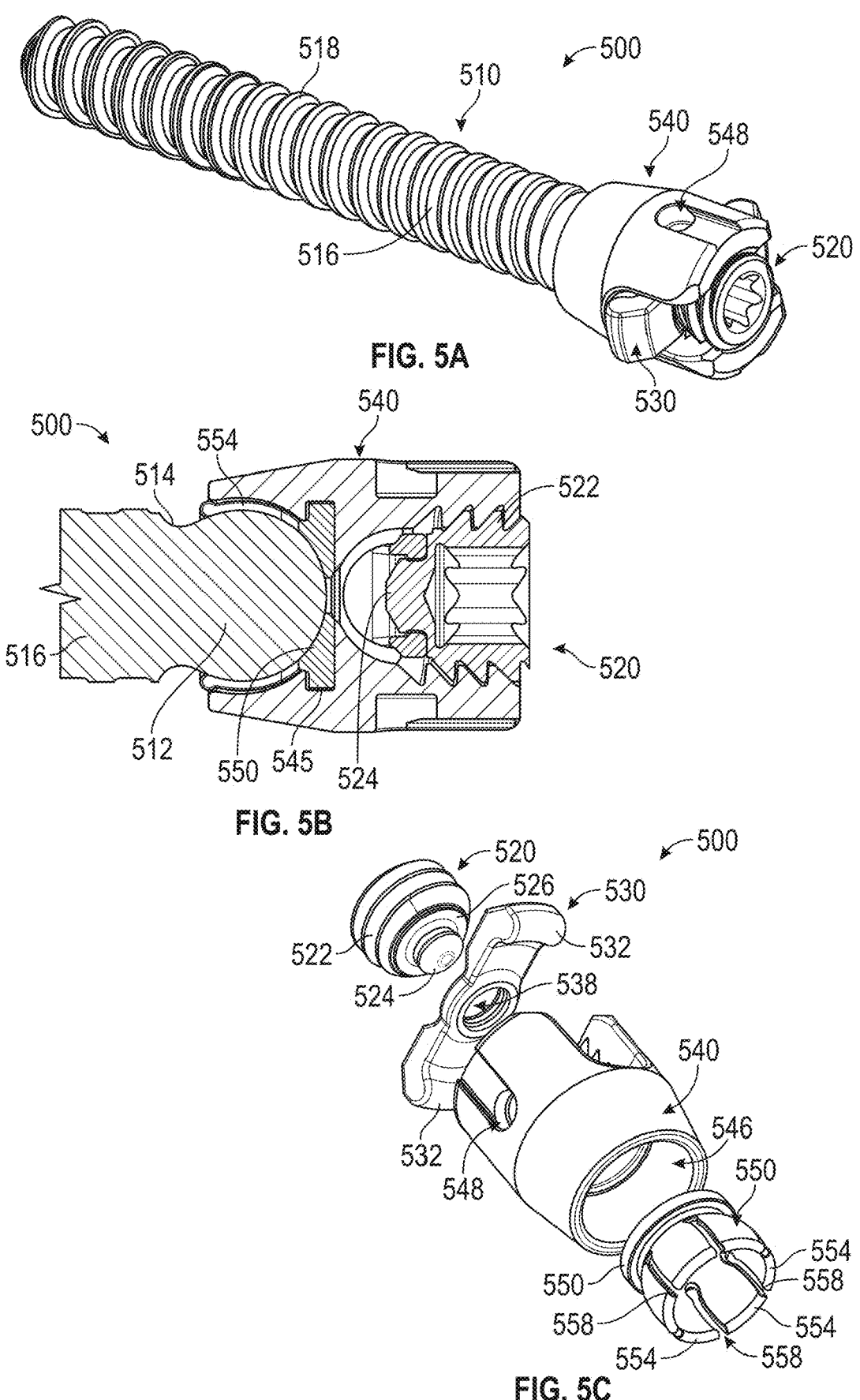
FIGS. 5A-5F are various views of a dynamic poly-axial head bone screw in accordance with the present disclosure.
Figure 5F:
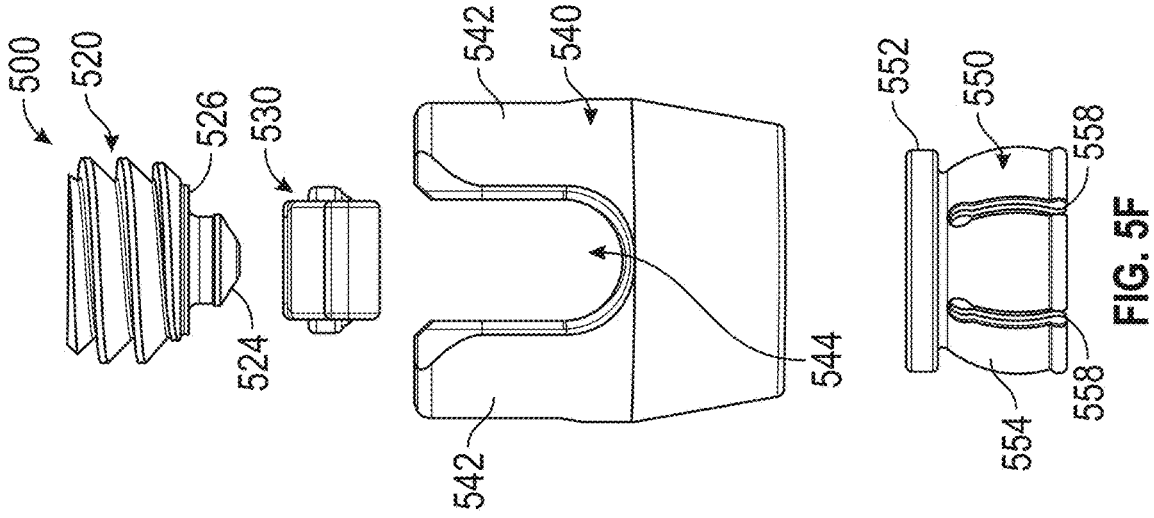
Figure 5E:
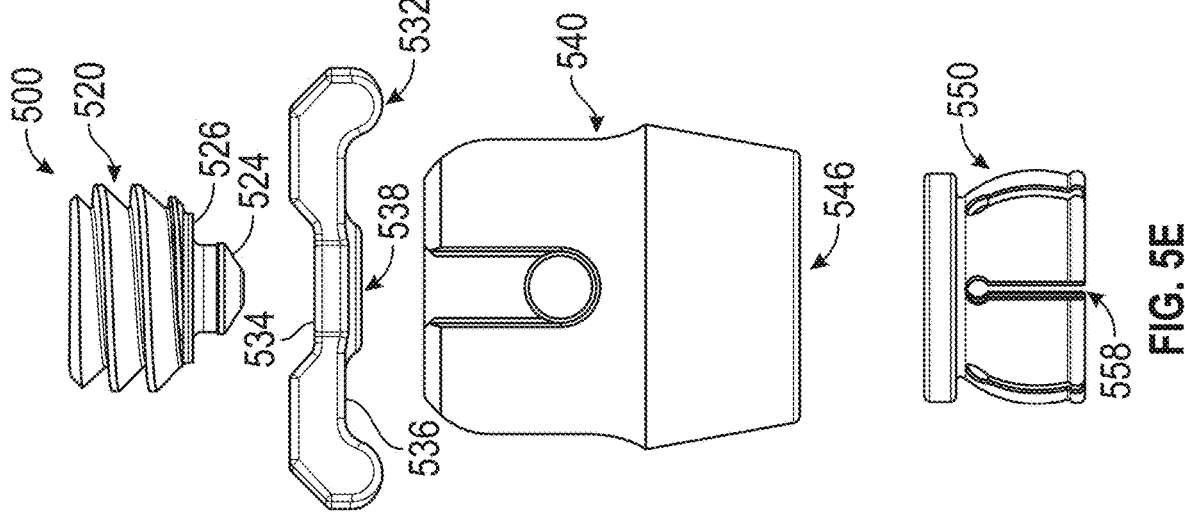
Figure 5D:
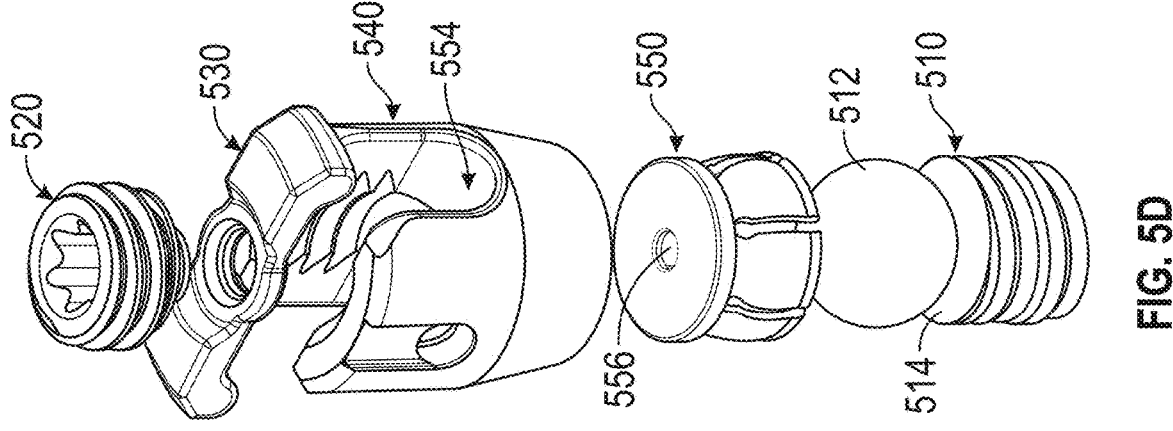

FIGS. 4C and 4D illustrate implant 400B that includes an anchor 440 with threaded anchor arms 441 integrated into the anchor (instead of the screw head, as in implant 400A). The screw head 420B includes a cylindrical disc shaped head that mates with a screw interface surface 446 within the screw passage 444 of anchor 440. In this example, the screw interface surface 446 is a circumferential lip extending from the inner sidewall of anchor 440 to capture screw head 420B. The anchor 440 includes anchor teeth 442 that are similar to those described above in reference to anchor 430. Also similar to anchor 430, anchor 440 includes a cord recess 445, but the cord recess 445 is formed in the space between threaded anchor arms 441 and includes a U-shaped notch in the cylindrical body of anchor 440. Anchor 440 also includes an instrument groove 448 for use in gripping the anchor with an implant instrument. Anchor 440 is designed to be implanted ahead of bone screw 410B or in conjunction with the bone screw 410B.

Both implants 400A and 400B utilize a cap-style set screw, such as cap screw 450. In these examples, the cap screw 450 includes a cylindrical body 456 with internal cap threads 452 designed to engage threaded arms 422 or threaded anchor arms 441. The cap screw 450 grips a cord (or tether) via cylindrical engagement surface 454. The cylindrical engagement surface 454 create two engagement points on a cord running through the implant. Implants 400A and 400B can also utilize a cap-style set screw similar to the one discussed above in reference to FIGS. 2A-2E that includes a central cord engagement member 234 in addition to the cylindrical surface 454.

FIGS. 5A-5F are various views of an implant 500 in the form of a dynamic poly-axial headed bone screw 510. In this example, the implant includes a bone screw 510 includes a set screw 520, a cord washer 530, a saddle body 540 and a friction insert 550. The bone screw 510 includes a spherical screw head 512 connected to a screw shaft 516 via a neck 514. The neck 514 has a reduced diameter in comparison to the spherical screw head 512, which allows for greater angulation of the screw shaft 516 in relationship to the saddle body 540. The bone screw 510 is coupled to the saddle body 540 via a friction insert 550. The friction insert 550 includes a body interface disc 552 that sits in an insert groove 545 recessed into an internal cylindrical sidewall of the saddle body 540. The friction insert 550 includes a series of head interface fingers 554 separated by compression gaps 558. The head interface fingers 554 and compression gaps 558 work in conjunction with the internal surface of the saddle body 540 to generate a predictable friction fit on the spherical screw head 512 that enables dynamic cord tension sharing (as discussed further below in reference to FIGS. 6A-7C).

Implant 500 includes a set screw 520 with external threads 522, and engagement extension 524 and a cylindrical mating surface 526. The engagement extension 524 is designed to mate with the set screw bore 538 of the cord washer 530. The cord washer 530 also includes a set screw recess 534 designed to receive the cylindrical mating surface 526 of the set screw 520. Similar to other cord washers discussed herein, the cord washer 530 includes cord grips 532 on either outbound end to extend the surface area (e.g., inferior surface 536) of the cord washer 530 that interfaces with a cord running in the cord recess 544 between the threaded saddle arms 542 of the saddle body 540. The set screw 520 with cord washer 530 attached is threaded into the saddle body 540 via the threaded saddle arms 542 after the friction insert 550 and bone screw 510 are assembled into the screw passage 546 of the saddle body 540. The entire implant 500 can be implanted using the instrument interfaces 548. In this example, the instrument interface 548 includes a vertical groove running from a superior surface of the threaded saddle arms 542 inferiorly to a circular recess.

When set screw 520 compresses cord washer 530 into saddle body 540, the entire implant 500 becomes a portion of a dynamic construct. The fiction insert 550 and spherical screw head 512 generate an interface that moves upon application of sufficient tension on the cord captured by the cord washer 530. The spherical screw head 512 will pivot upon application of a tension on the cord that exceeds the tension applicable by a tensioning instrument, but beyond the yield strength of the cord.

Figures 6A, 6B, 6C:
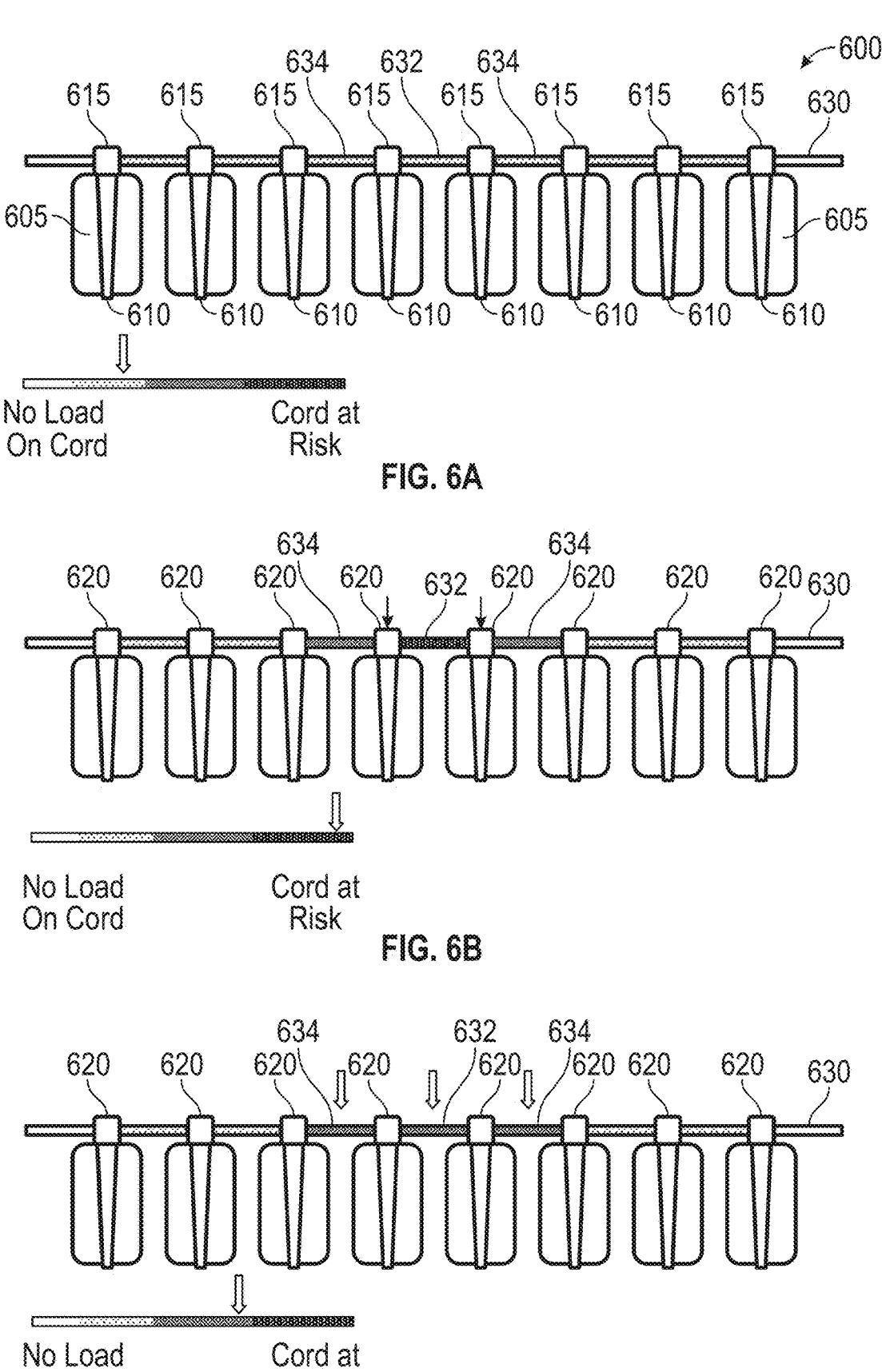
FIGS. 6A-6C are illustrations of a dynamic construct using cord slip tension sharing in accordance with the present disclosure.

FIGS. 6A-6C are illustrations of a dynamic construct 600 using cord slip tension sharing provided by implants, such as implant 200 discussed above. A concern with tether constructs used to correct adolescent scoliosis involves cord failure at the apex of the construct (or another stress point caused by growth or physical activity). It has been determined that tether constructs can develop stress points, typically at the apex of the construct as growth occurs. The present inventors determined that creating implants, such as implant 200, that can allow for cord slippage at pre-determined tension levels can alleviate some forms of cord stress and avoid potential failures in a tether construct.

In an example, the dynamic sharing implants are designed to share tension loading at tension levels above the level attainable with a tensioning instrument and below the cord yield strength. Dynamic tension sharing systems will also take into consideration the tension level where screw plow is known to occur for a given implant design. Screw plow involves the bone screw portion of an implant migrating within a vertebral body in response to tension generated by the tether (cord). In an example tethering system, a tensioning instrument can generate approximately 500 Newtons (N) of tension between implants (e.g., between each vertebral body). In this example, screw plow may occur around 800N of tension and the cord yield strength may be as high as 3000N of tension. Implants within a tethering construction will also often induce stresses onto the cord that reduces the cord yield strength to as little as ⅓ the actual yield strength. In other words, the effective construct strength may be as little as 1000N of tension before cord failure is likely. Many of the implant designs outlined within this disclosure are designed to increase the overall construct strength by increasing the effective strength of the construct, in part by reducing stress levels induced on the cord. Designs such as the cord washers shown in FIGS. 1A-1K and 5A-5F are examples of implant designs that seek to reduce stresses induced on the cord. An ideal implant design would enable the construct to utilize the full yield strength of the cord (e.g., 3000N). Realistically, the designs discussed herein may reach levels approaching 2000N between improvements in cord clamping and holding strength within the vertebral body.

In this example, the dynamic tension sharing construct implants are designed to load share at a tension below the 800N screw plow level of standard pedicle-style bone screws and above the 500N tensioning instrument level. In another example, the implant may be designed with a screw plow tension level of 1000N, and the dynamic tension sharing target may be in a range of 600N to 900N, which is well above initial tensioning level of 500N and below the screw plow tension level of this implant of 1000N. Most of the implant designs discussed herein that allow for dynamic tension sharing can have the tension level target for sharing adjusted by set screw torque or other similar implant parameters.

FIG. 6A illustrates a standard tether construct 600 with implants 610 in each vertebra 605 connected by cord 630. In FIG. 6A, the implants 610 include static heads 615 that are not designed for dynamic cord slip behavior. As shown in FIG. 6A, the cord 630 can include areas with higher stress, such as the cord at the apex 632 and cord sections 634 adjacent to the apex 632. In FIG. 6B, the tether construct 600 is illustrated with the cord 630 experiencing critical tension at the apex 632. Replacing static heads 615 with dynamic heads 620 that will allow for cord slippage above a pre-defined tension level can result in the critical cord stress at the apex 632 being distributed across adjacent cord sections 634, as shown in FIG. 6C. Allowing the cord to slip through certain screw heads, can result in distributing the cord stresses across multiple levels and reducing the opportunity for cord failure at any one level.

In these examples, the implants 600 are configured with dynamic heads 620 that allow for cord slip once the cord has reached a load that is above the tensioning load but below the screw plow and cord failure loads. When the cord 630 reaches a critical level between any two screws, the dynamic heads 620 release to distribute the tension across the two adjacent levels. If the tension is high enough, the dynamic heads 620 for these additional adjacent levels may also release to further distribute the higher tension load across more of the tether construct 600.

Figure 7A:
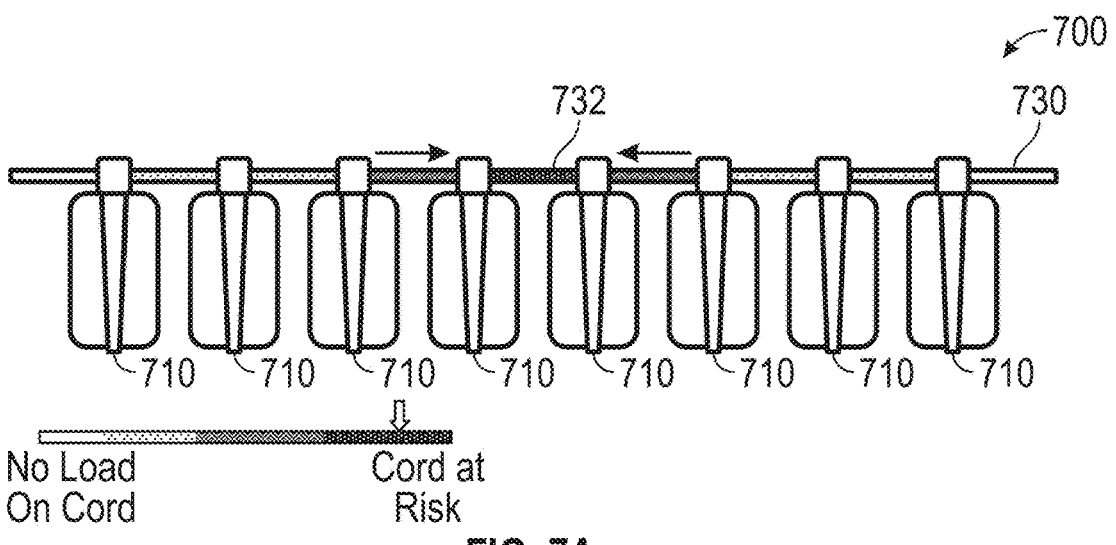
FIGS. 7A-7C are illustrations of a dynamic construct using head tilt tension sharing in accordance with the present disclosure.
Figure 7B:
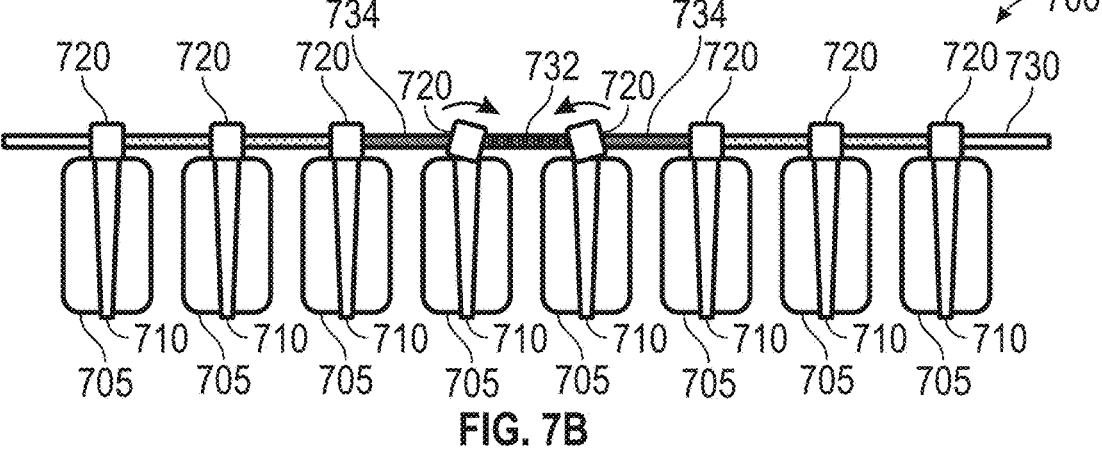
Figure 7C:
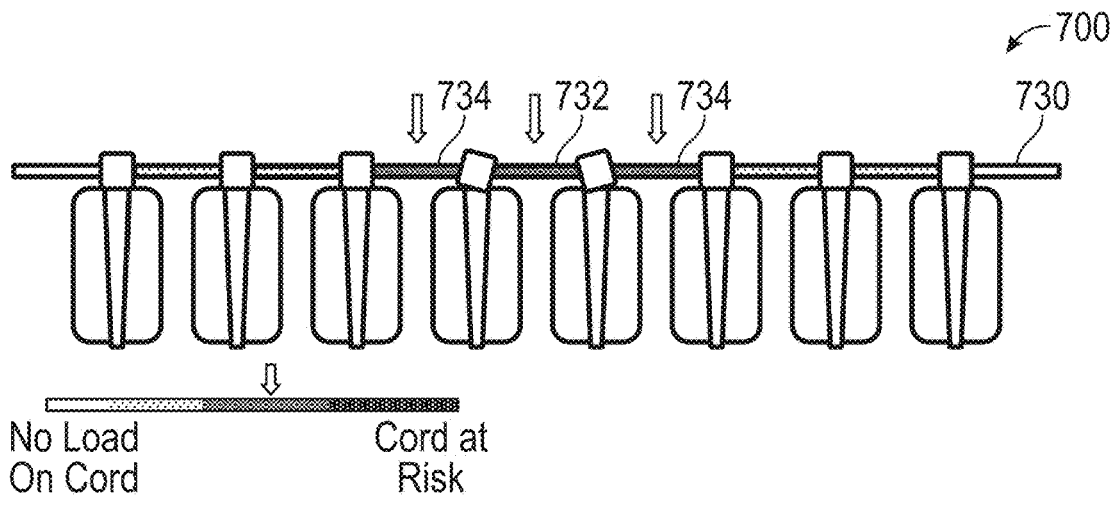

FIGS. 7A-7C are illustrations of a dynamic construct 700 using head tilt tension sharing implants, such implant 500 discussed above. Dynamic construct 700 operates in a manner similar to dynamic construct 600 discussed above, but with dynamic heads 720 that tilt in response to tension loads above a pre-defined level (e.g., above initial tension level but below screw plow or cord failure strength). FIG. 7A illustrates dynamic construct 700 with implants 710 coupling cord 730 across seven spinal levels (e.g., connecting eight vertebral bodies). FIG. 7A illustrates the cord at the apex 732 at risk of failure. FIG. 7B illustrates the two implants 710 responding to the cord at risk (apex 732) by tilting inward towards each other, which operates to shorten the cord segment at the apex 732 and lengthen the adjacent segments 734. The head tilt operation effectively shares the tension load across two additional levels as shown in FIG. 7C, with the critical tension load spread across the apex 732 and two adjacent segments 734. In certain examples, the dynamic heads 720 can utilize a uniaxial design that only allows for tilting within a single plane, and that plane of tilt would be aligned with the cord in these examples. Uniaxial bone screw designs known in the industry could be adapted for use in such a dynamic construct.

FIGS. 8A-8J are various views of bone anchors 800 used to strengthen bone screw connection to a vertebral body for spinal tethering techniques. In this example, the bone anchor 800 is designed to be implanted ahead of a bone screw, which is then inserted through screw passage 840. In some examples, the bone anchor 800 is designed with anchor spikes 810 that expand radially outward as a bone screw 850 with a tapered neck 854 is implanted into the vertebral body. The bone anchor 840 can include a cylindrical anchor body 805 that forms screw passage 840. Around the outer circumference of cylindrical anchor body 805 is an instrument groove 820. Extending from an inferior rim of the cylindrical anchor body 805 are multiple anchor spikes 810. The superior surface of the cylindrical anchor body 805 forms a screw engagement surface 830, which can include a radiused surface slopping into the screw passage 840.

Figure 8A:
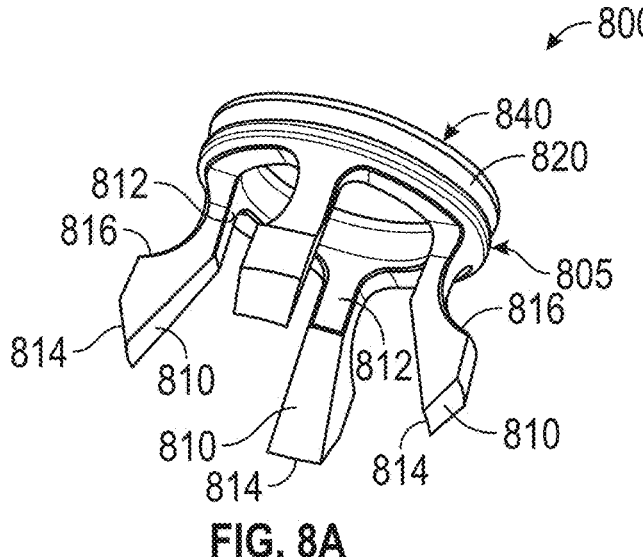
Figure 8B:
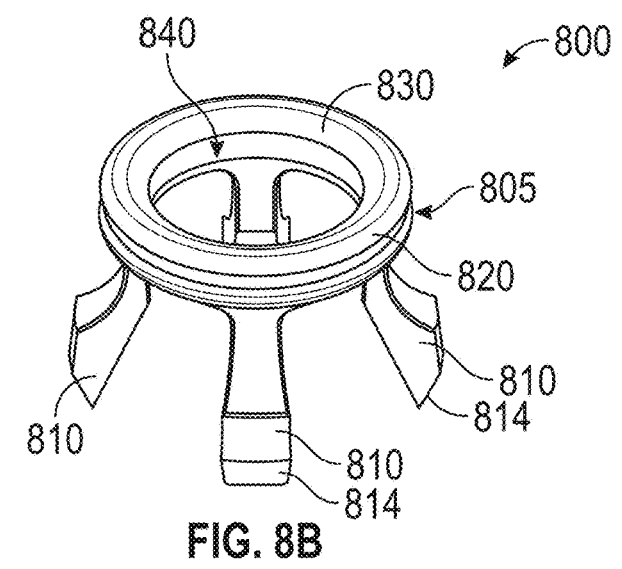
Figure 8C:
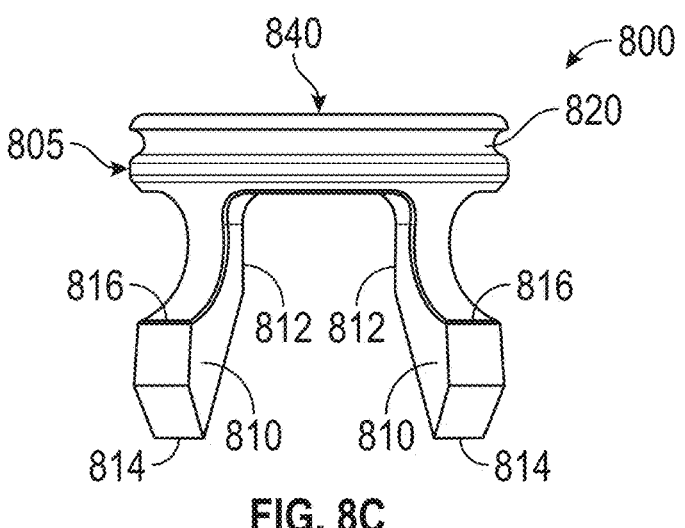
Figures 8D, 8E, 8F, 8G:
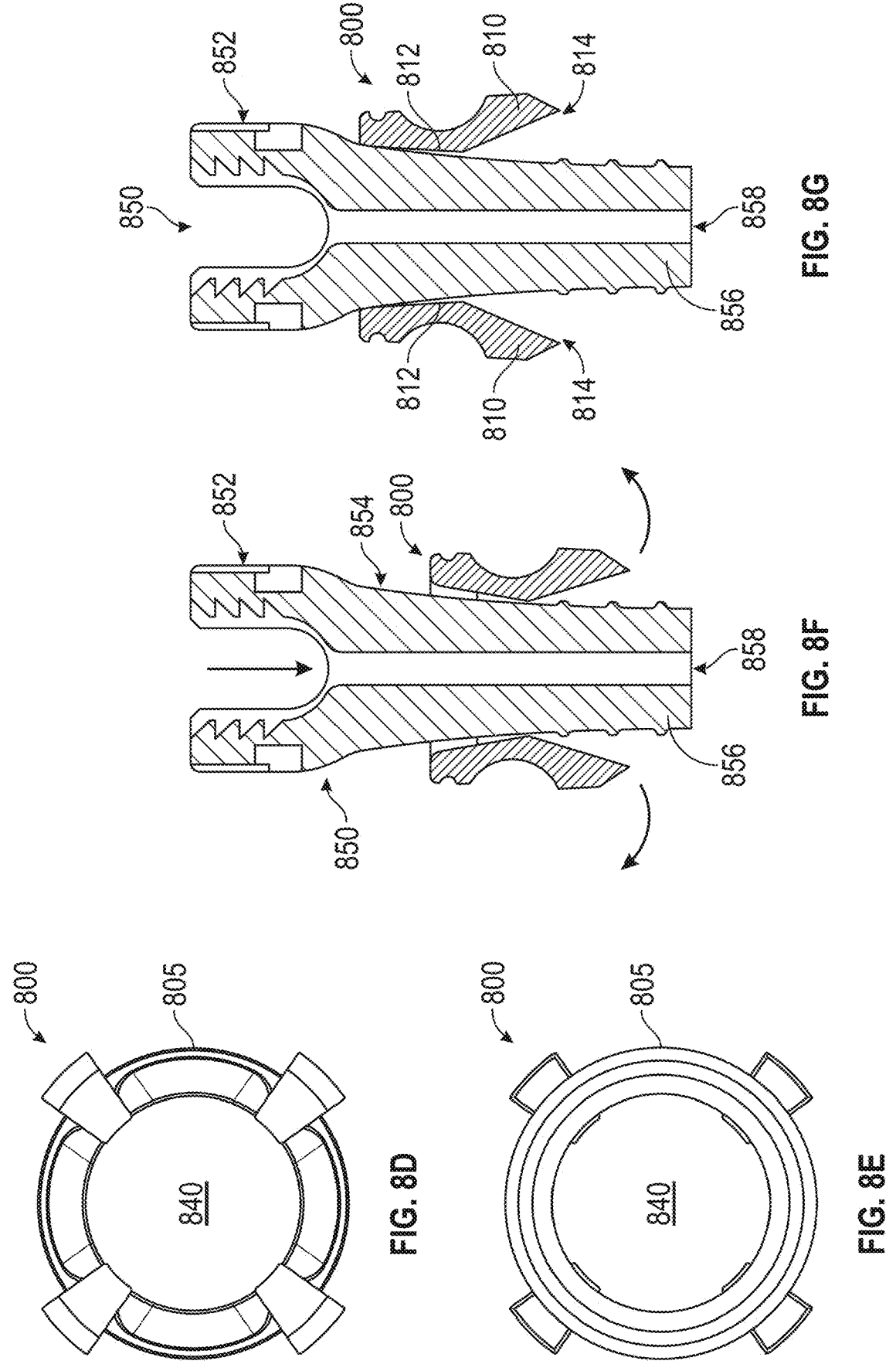

In an example, the anchor spikes 810 can include a screw neck interface 812, a chisel tip 814 and a retention feature 816. The retention feature 816 extends radially outward from the main body of the anchor spike 810 with a concave radius. The retention feature 816 is designed to grip cortical bone as the bone screw 850 expands the anchor spikes 810 through interaction with the screw engagement surface 830 (as illustrated in FIGS. 8F-8G). Bone screw 850 is designed for use with bone anchor 800. The tapered neck 854 is designed to cause the anchor spikes 810 to expand radially outward as the bone screw 850 is implanted through the bone anchor 800. Bone screw 850 includes a tulip head 852 attached to a tapered neck 854 that extends into threaded shafter 856. The bone screw 850 can also include a fenes-tration 858 to enable implantation with K-wire guides. The tulip head 852 is fixed to the tapered neck 854 and designed to receive a cord for use in a tethering construct. The bone screw 850 can be combined with cord washers and various set screw designs discussed above to enhance cord/tether gripping interface, among other things.

Figure 8J:
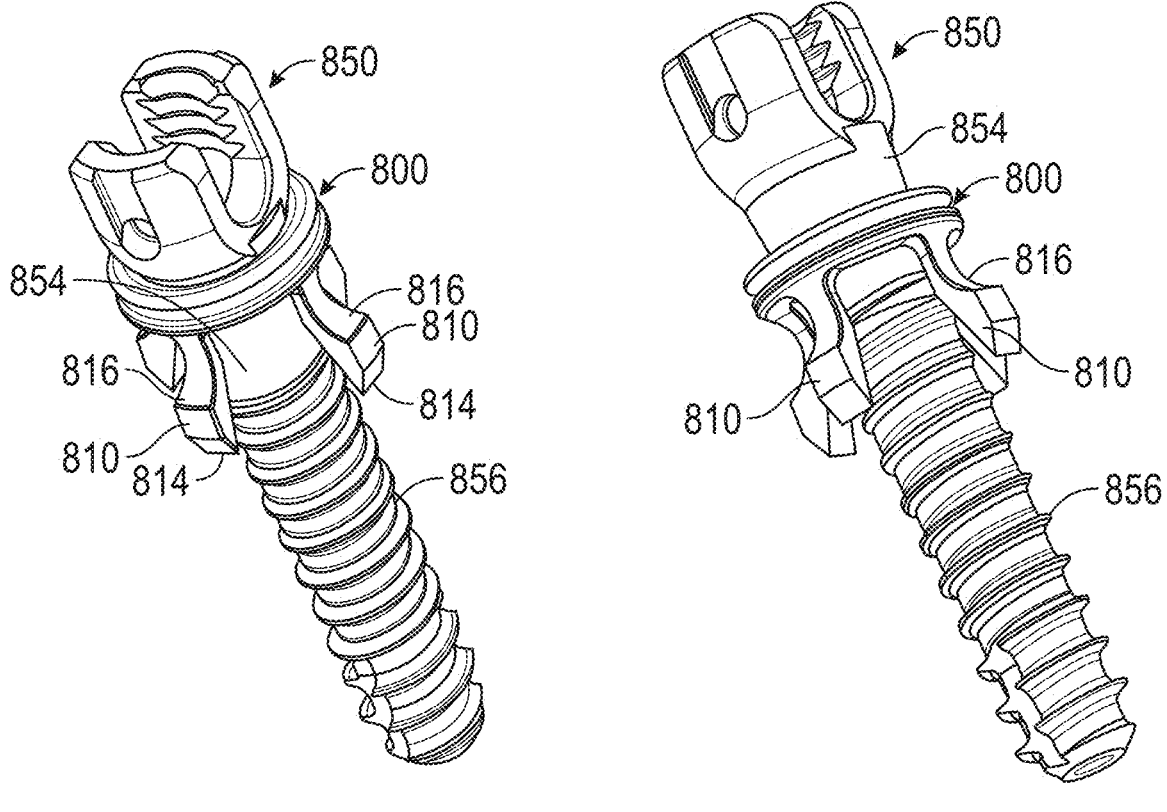
Figure 8J:
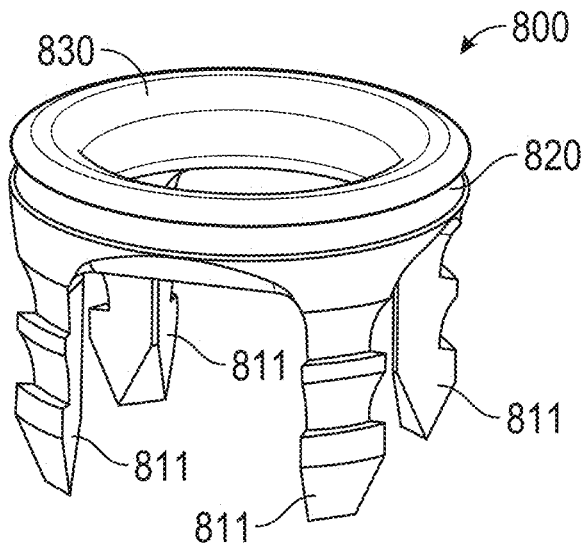
Figures 9A, 9B, 9C, 9D, 9E, 9F:
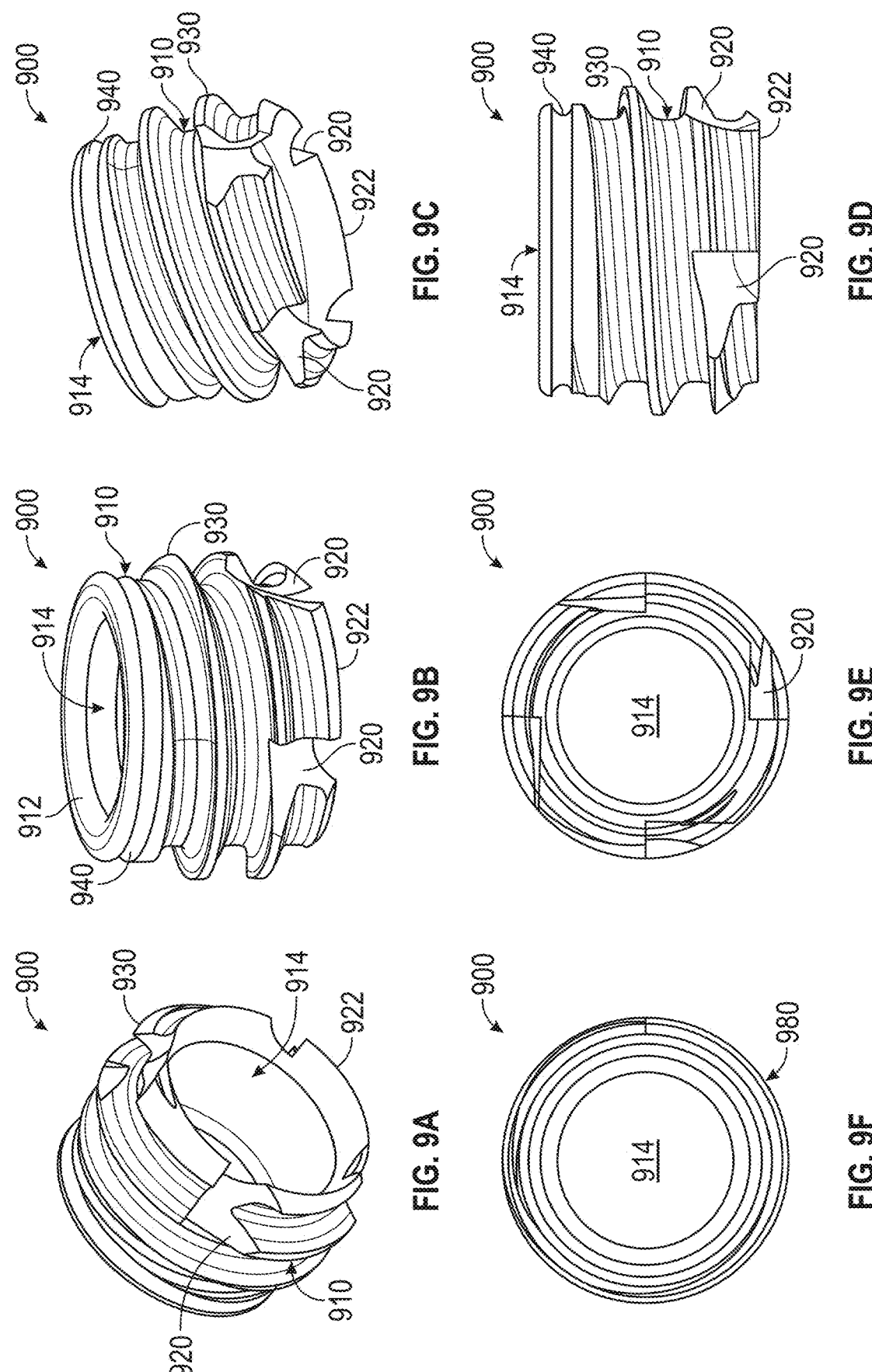
FIGS. 9A-9F are various views of a threaded bone anchor in accordance with the present disclosure.
Figures 10A, 10B, 10C:
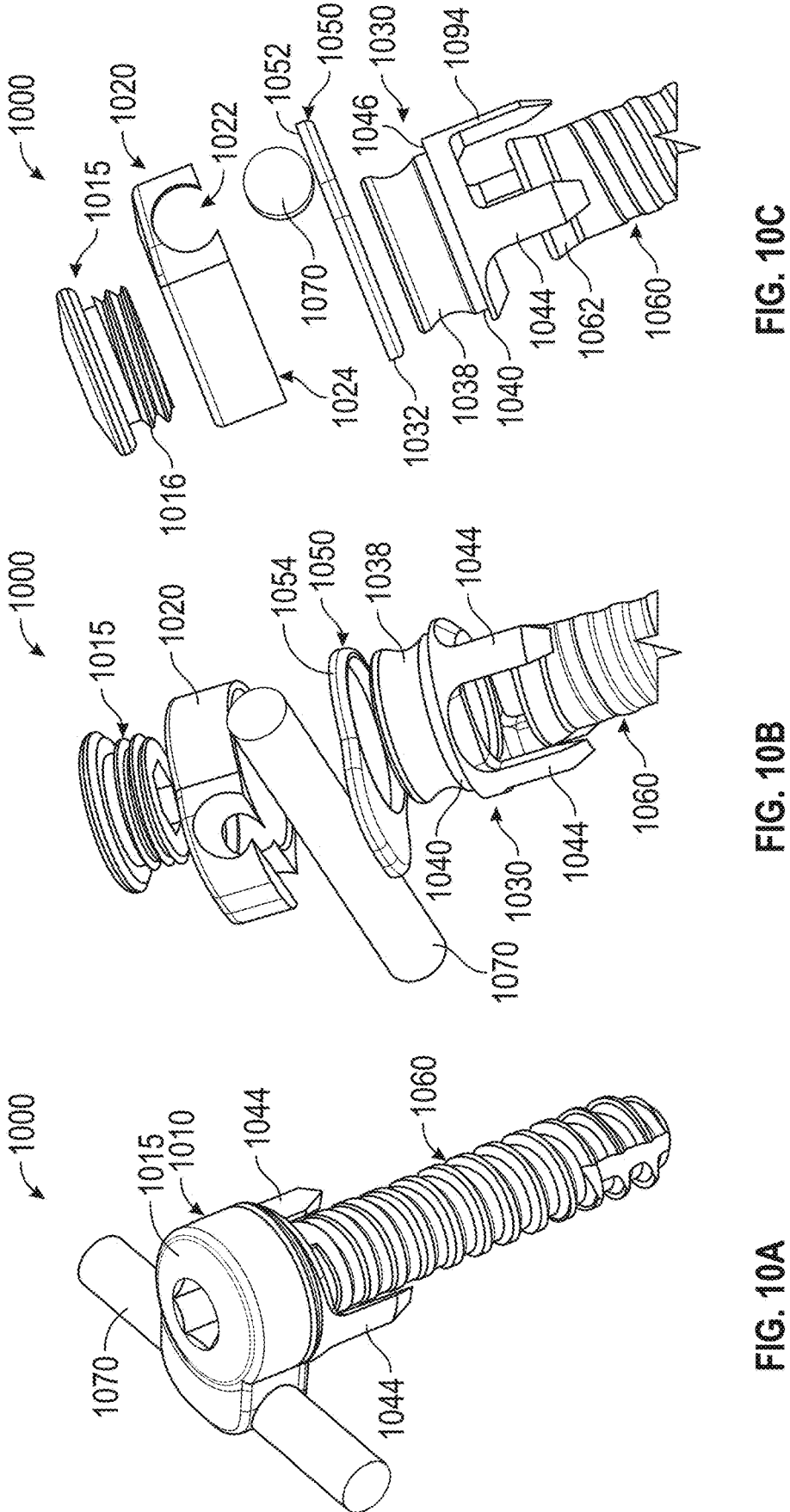
FIGS. 10A-10H are various views of an offset single cord clamp in accordance with the present disclosure.
Figures 10D, 10E, 10F:
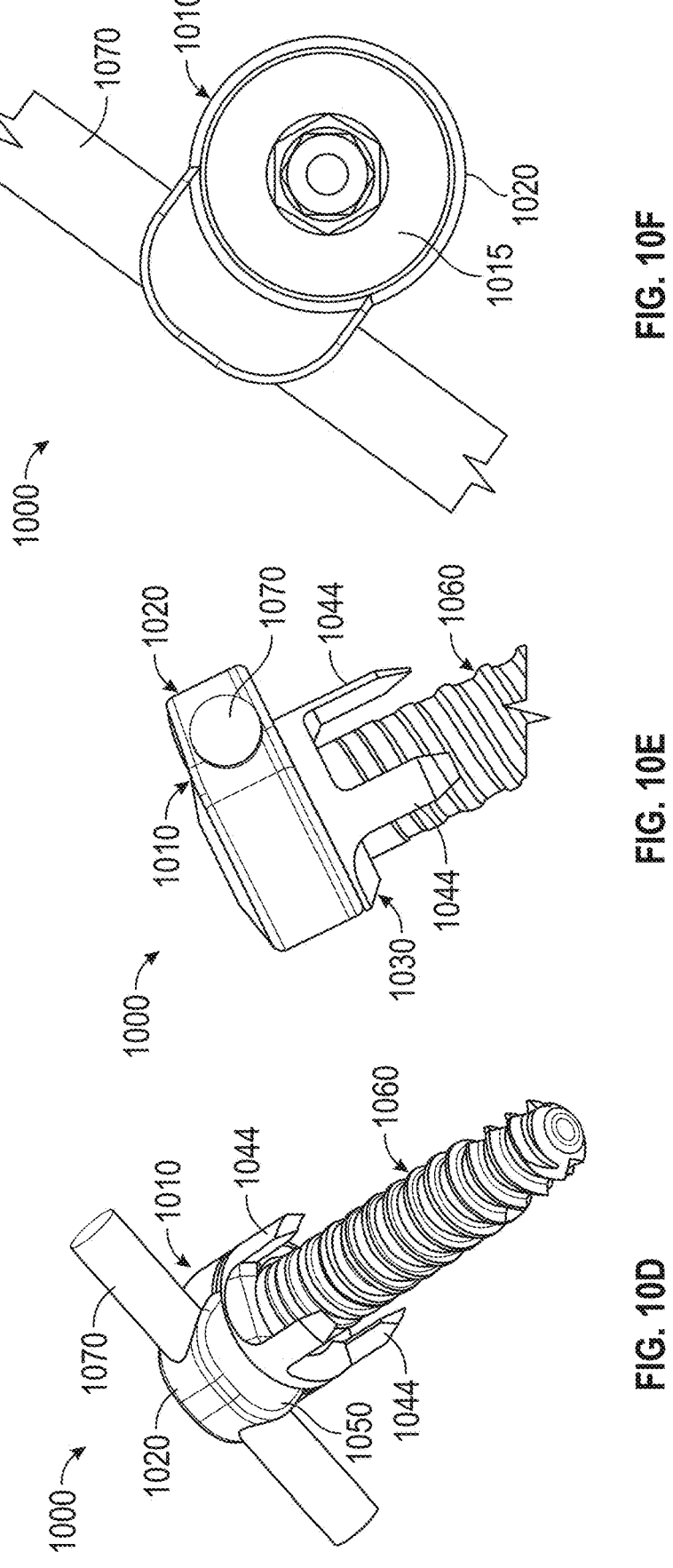
Figures 10G, 10H:
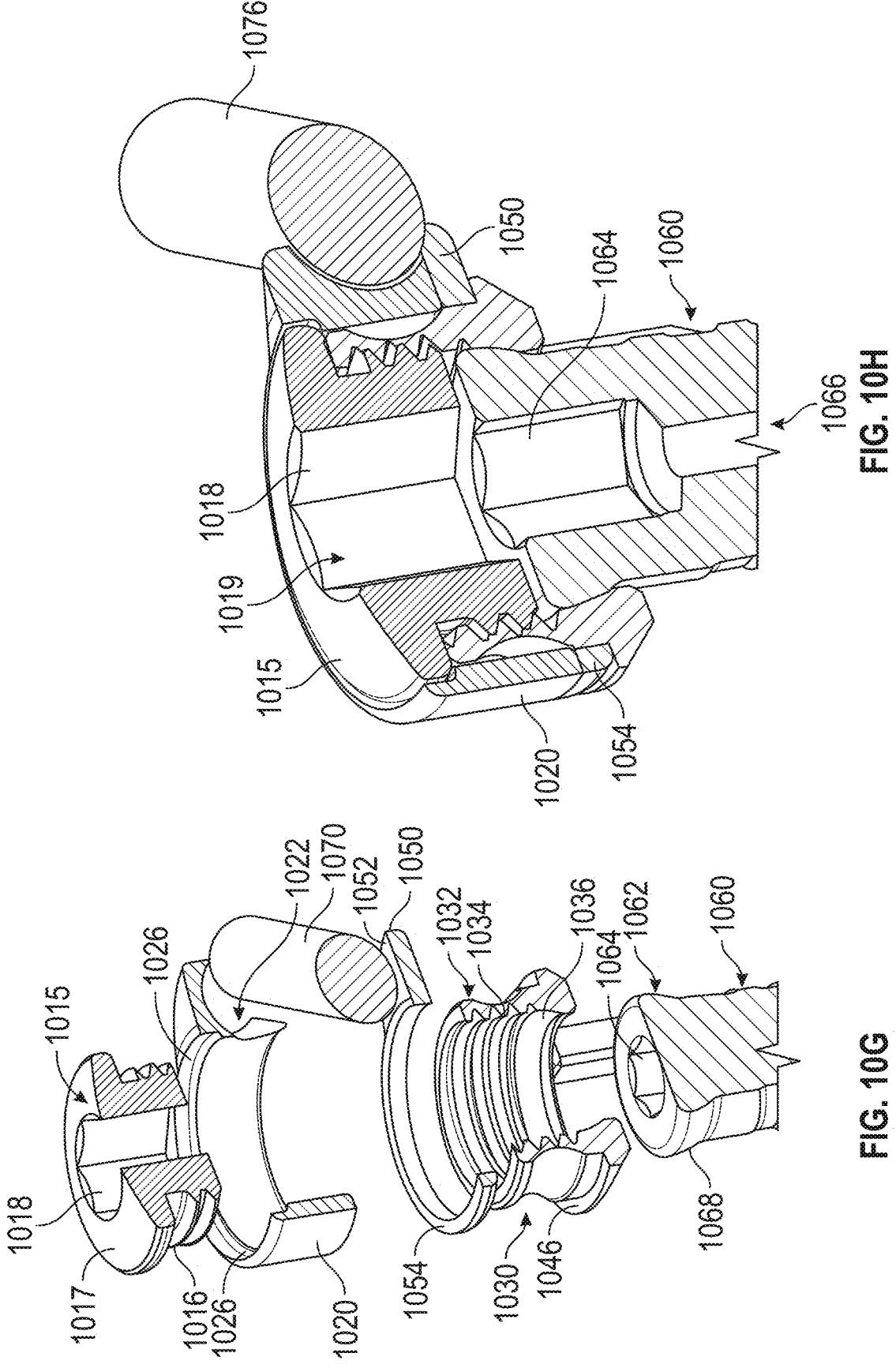
Figure 11B:
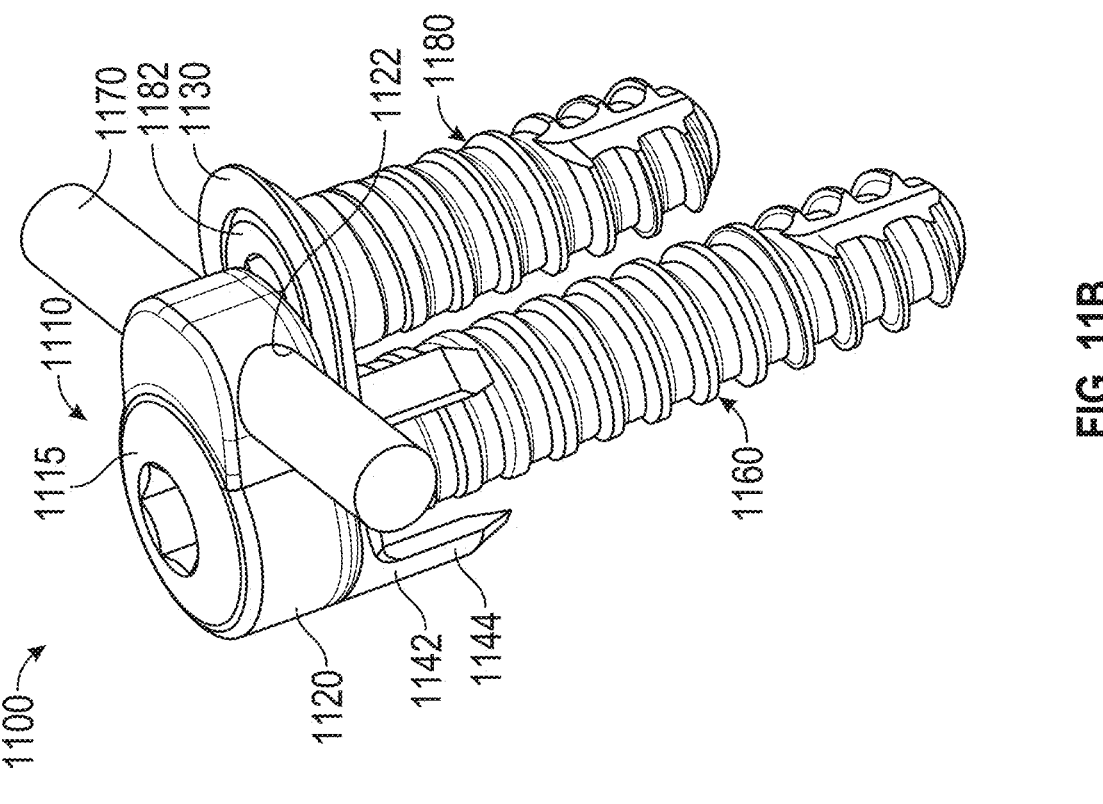
FIGS. 11A-11G are various views of an offset single cord clamp with dual bone screws in accordance with the present disclosure.
Figure 11A:
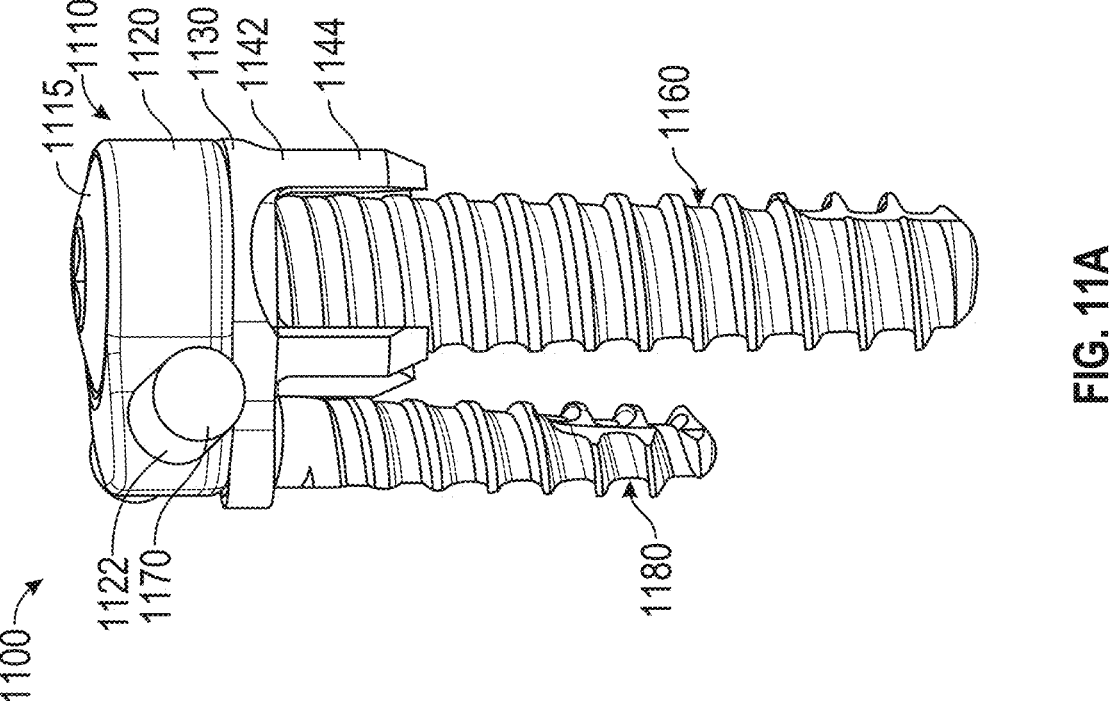
Figures 11C, 11D, 11E:
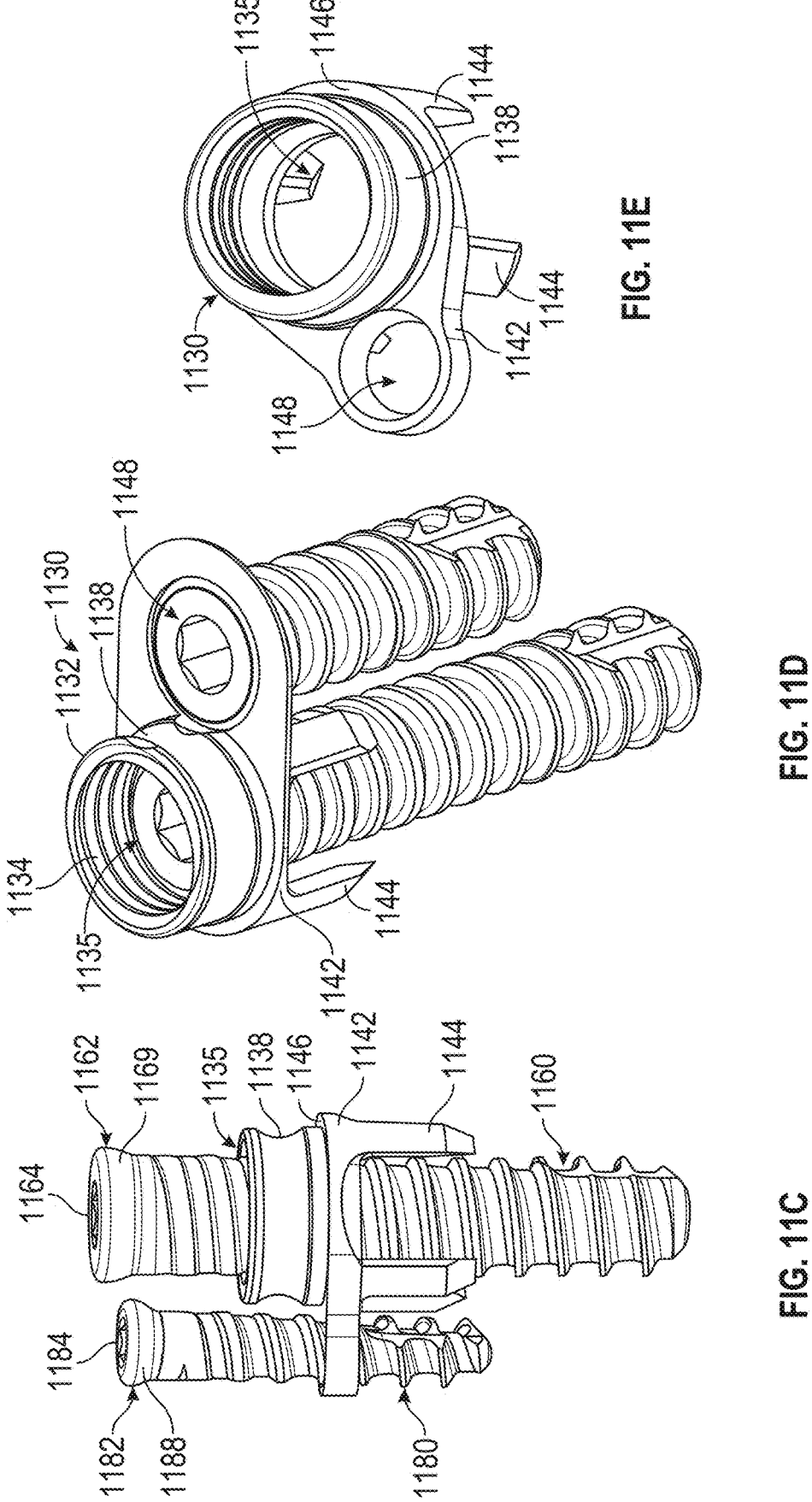
Figures 11F, 11G:
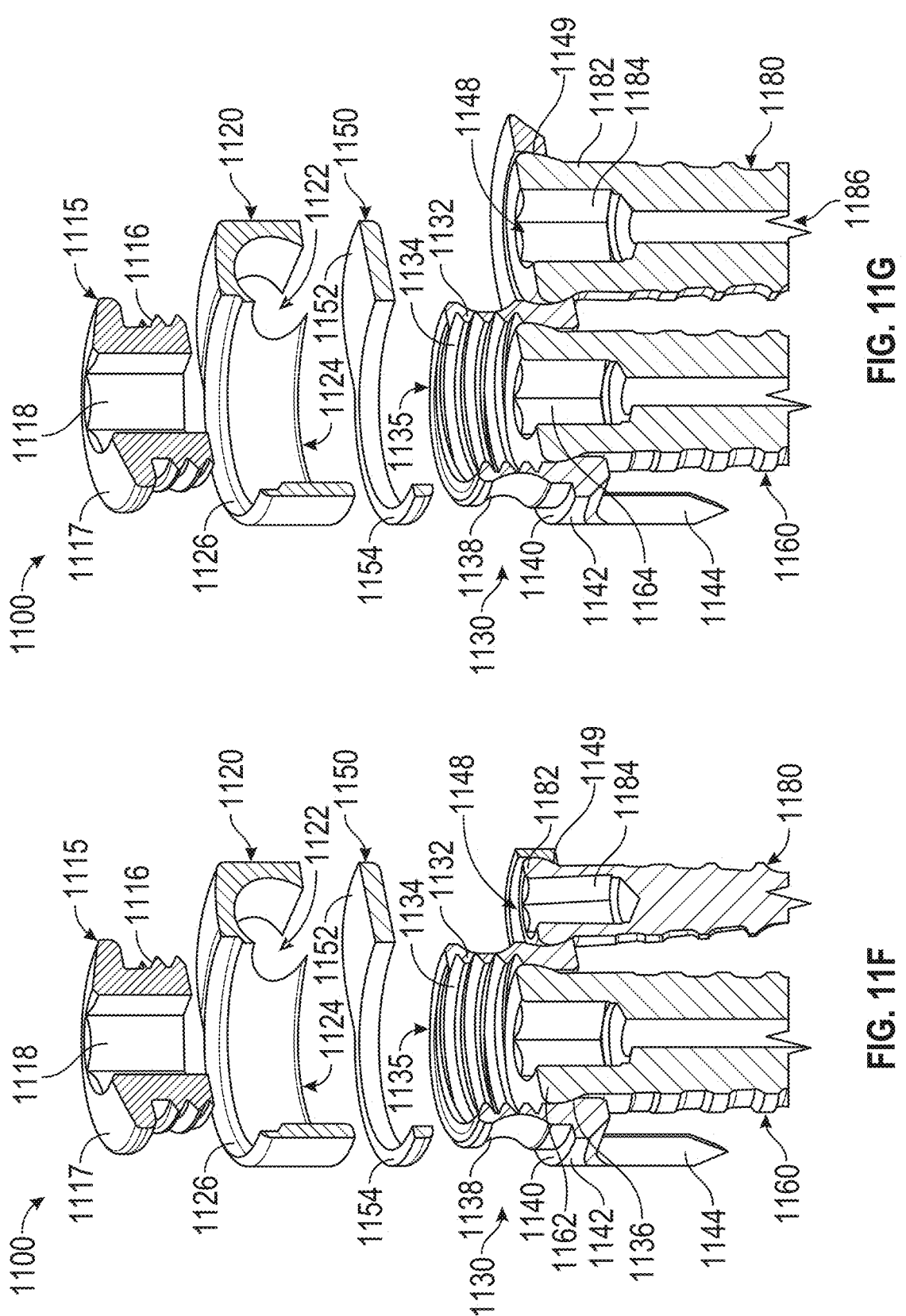
Figure 12B:
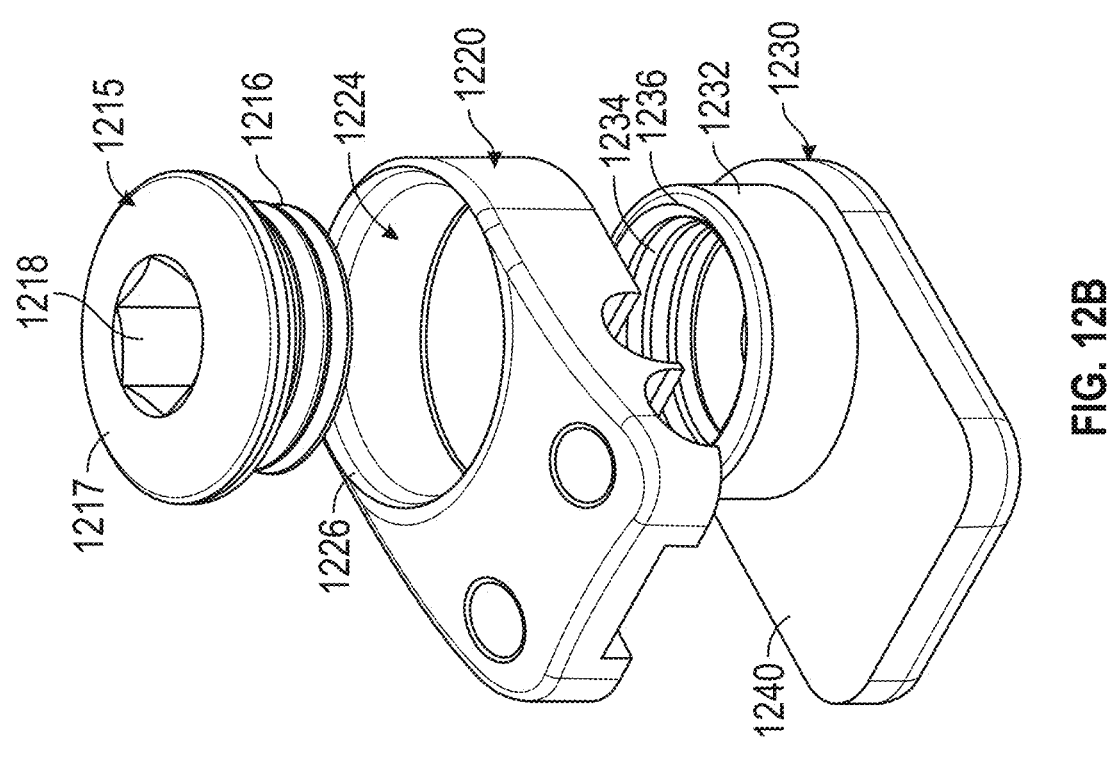
FIGS. 12A-12D are various views of an offset dual cord clamp in accordance with the present disclosure.
Figure 12A:
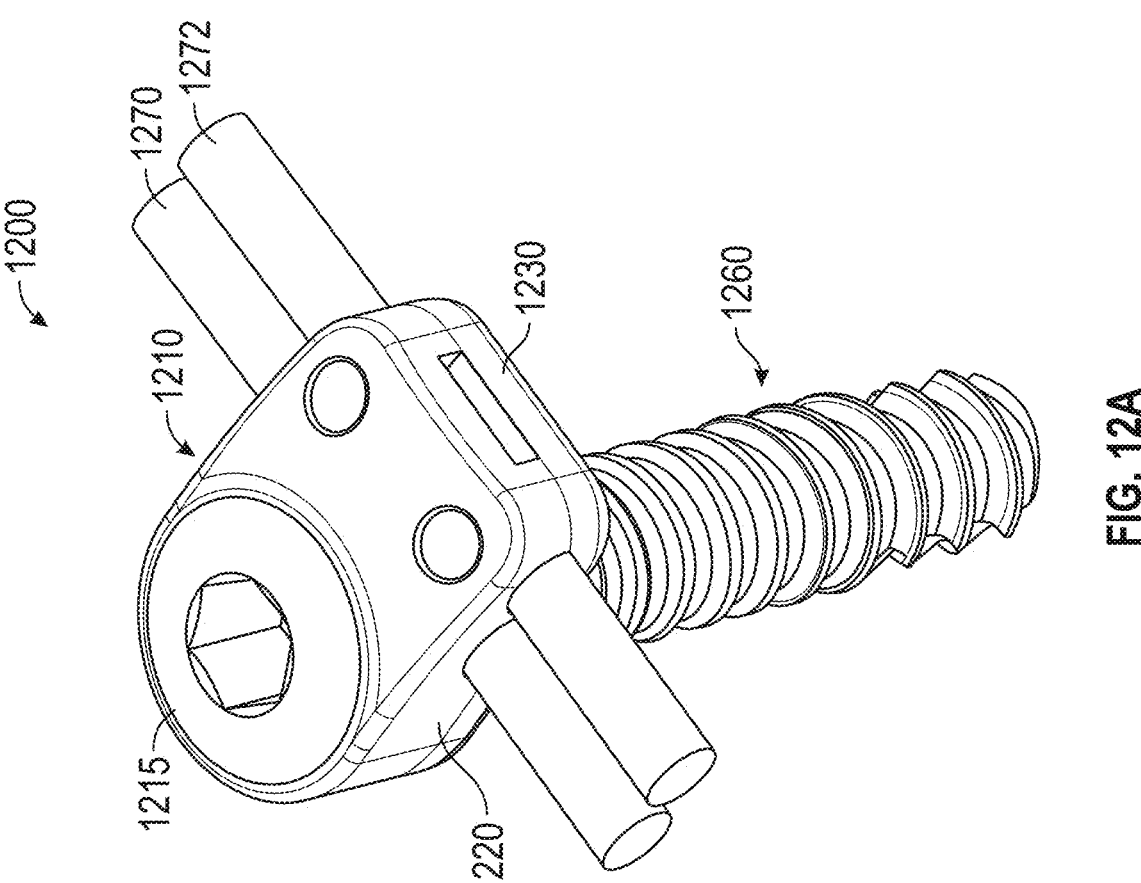
Figure 12D:
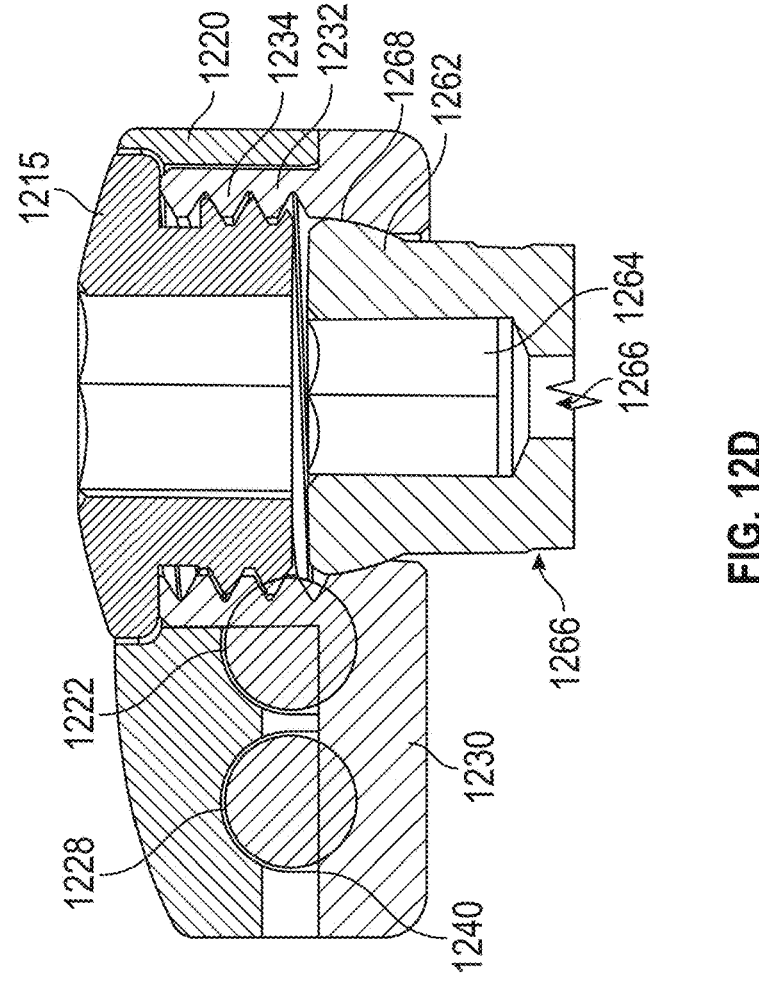
Figure 12C:
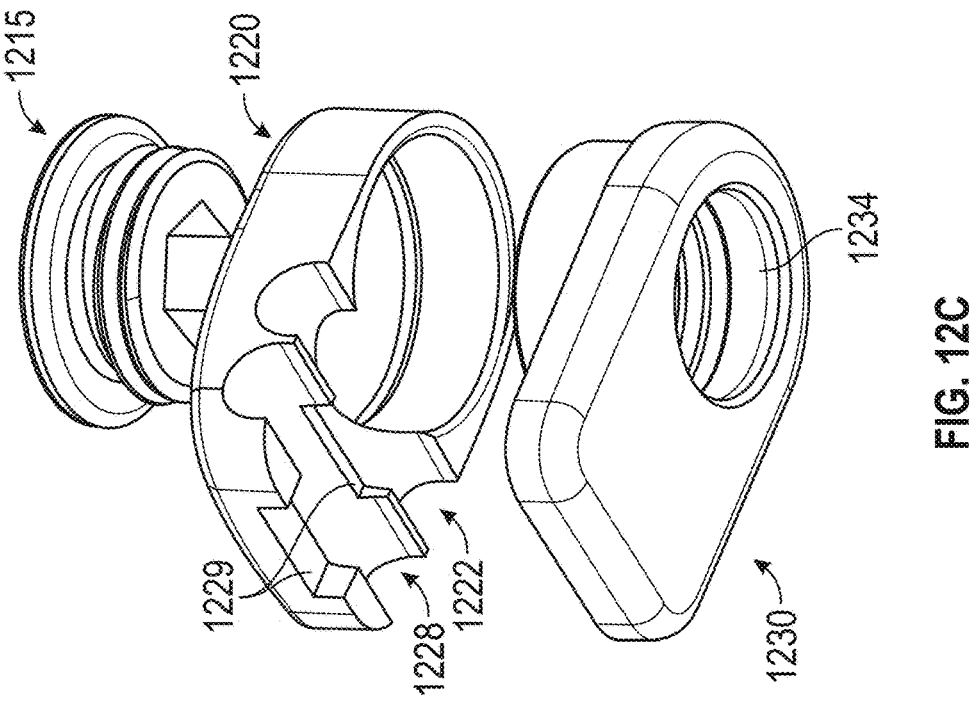
Figures 13A, 13B:
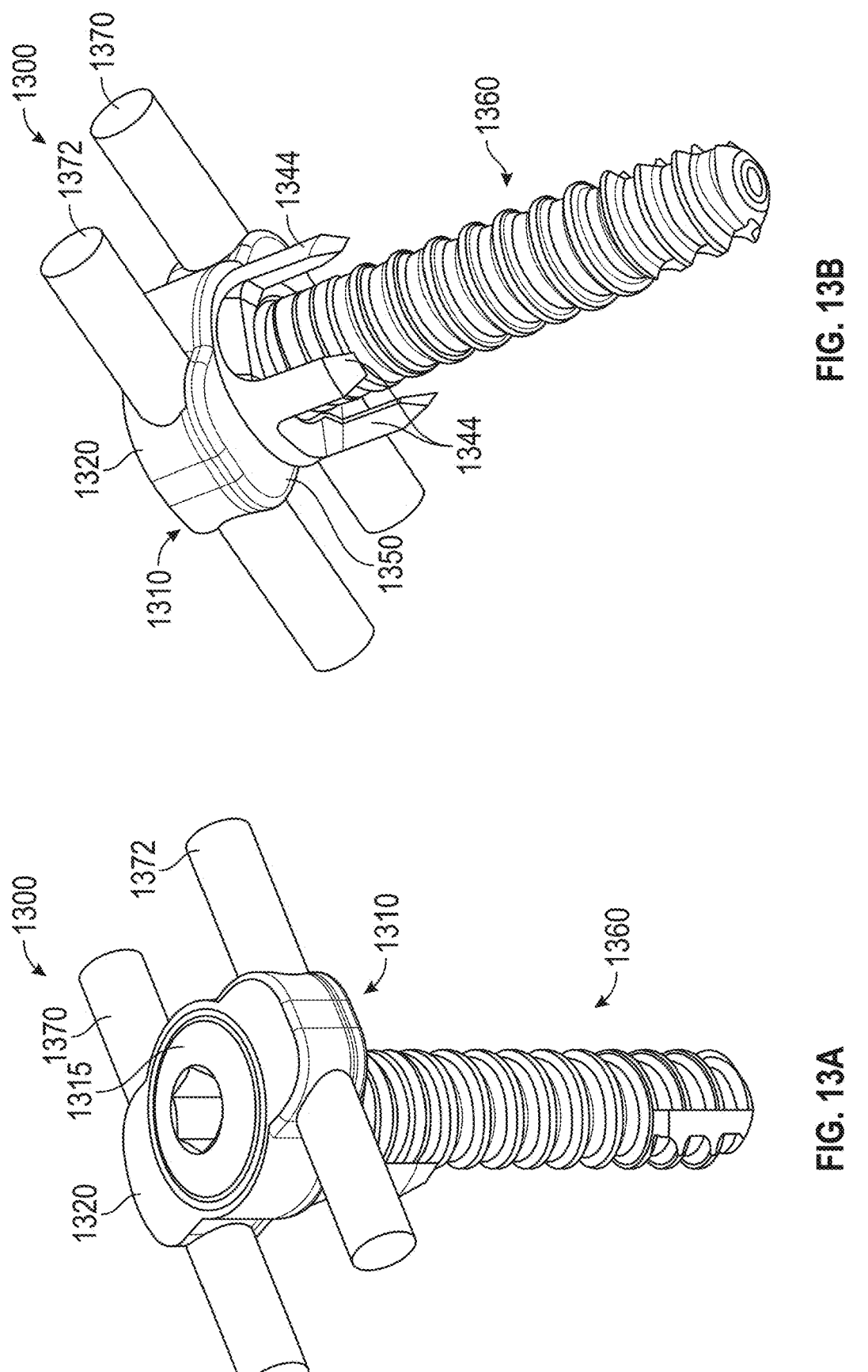
FIGS. 13A-13F are various views of a symmetric offset dual cord clamp in accordance with the present disclosure.
Figure 13D:
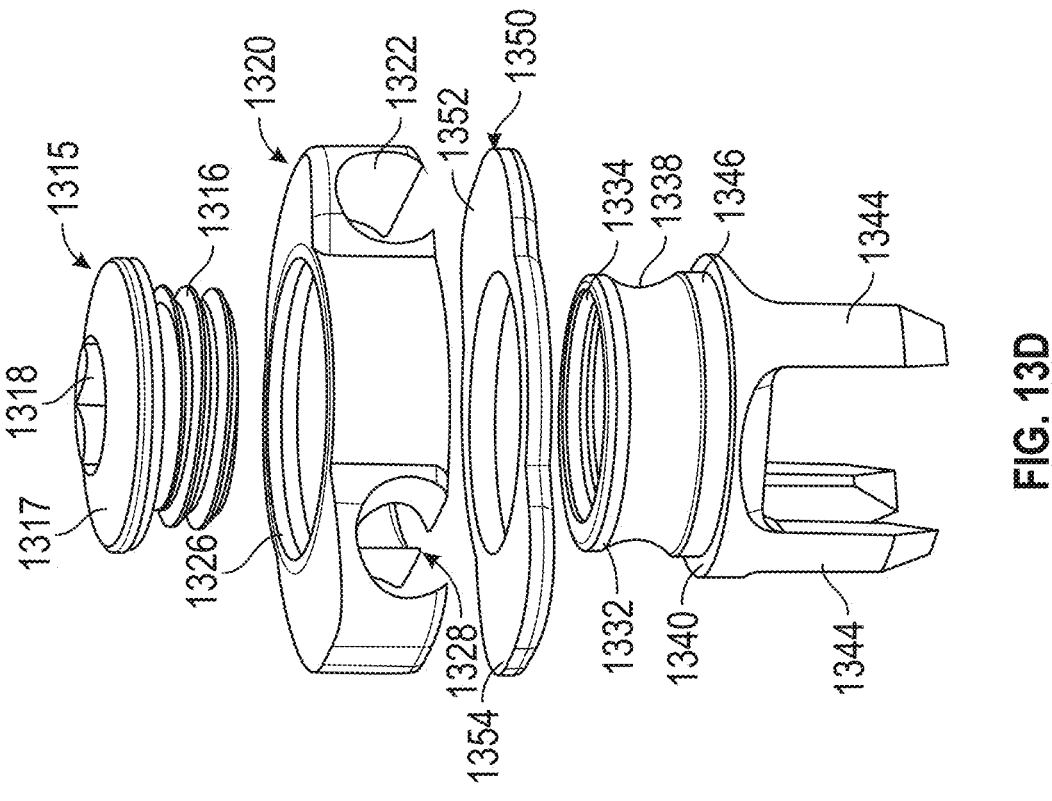
Figure 13C:
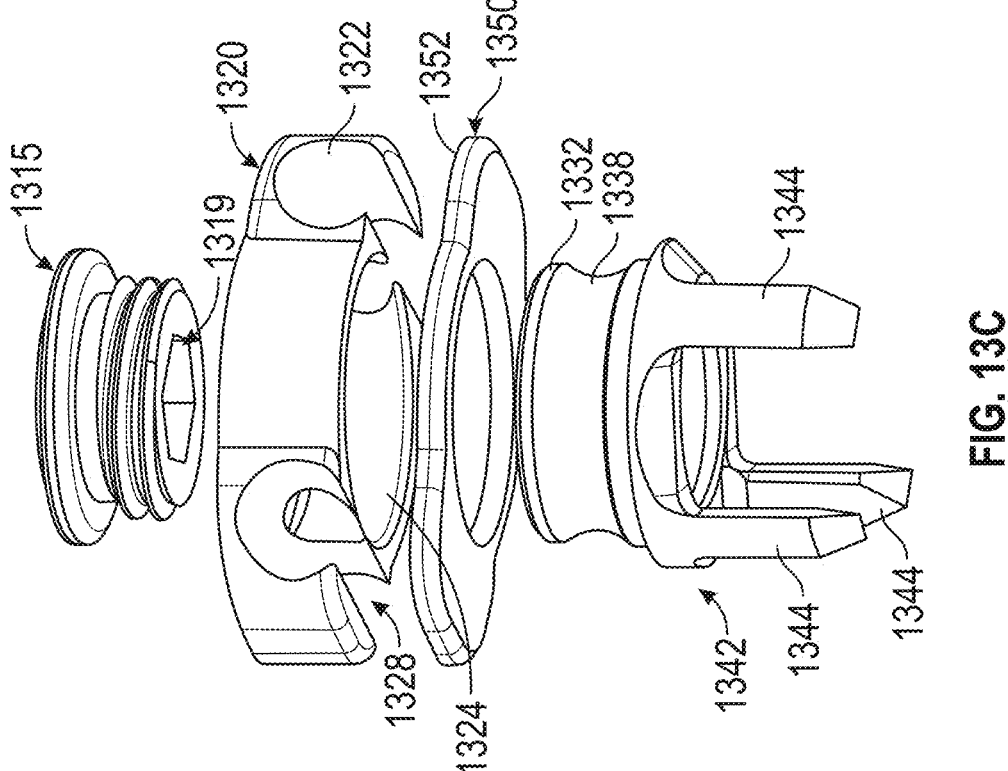
Figure 13E:
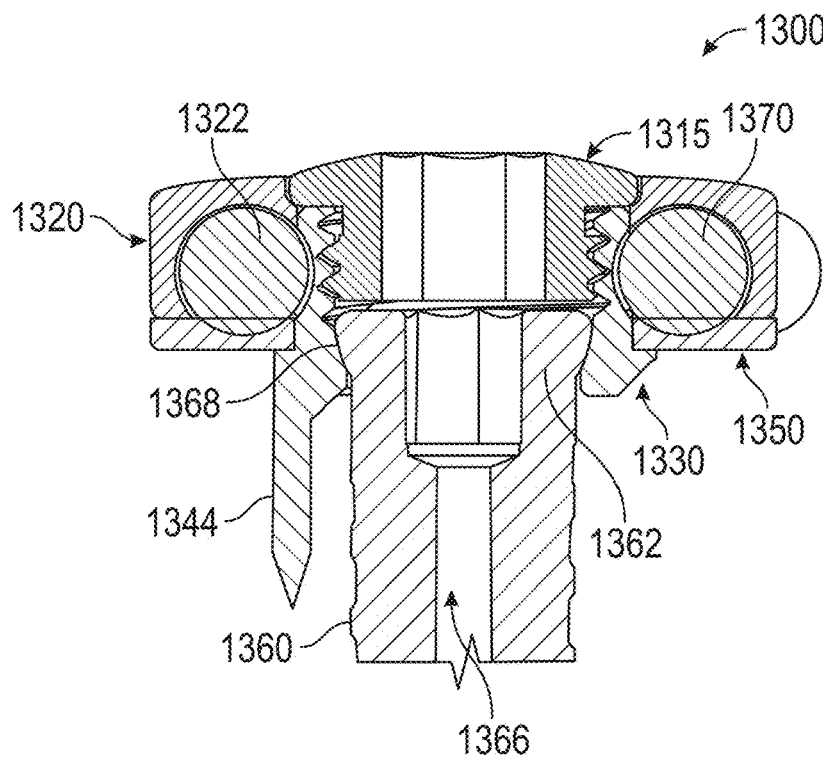
Figure 13F:
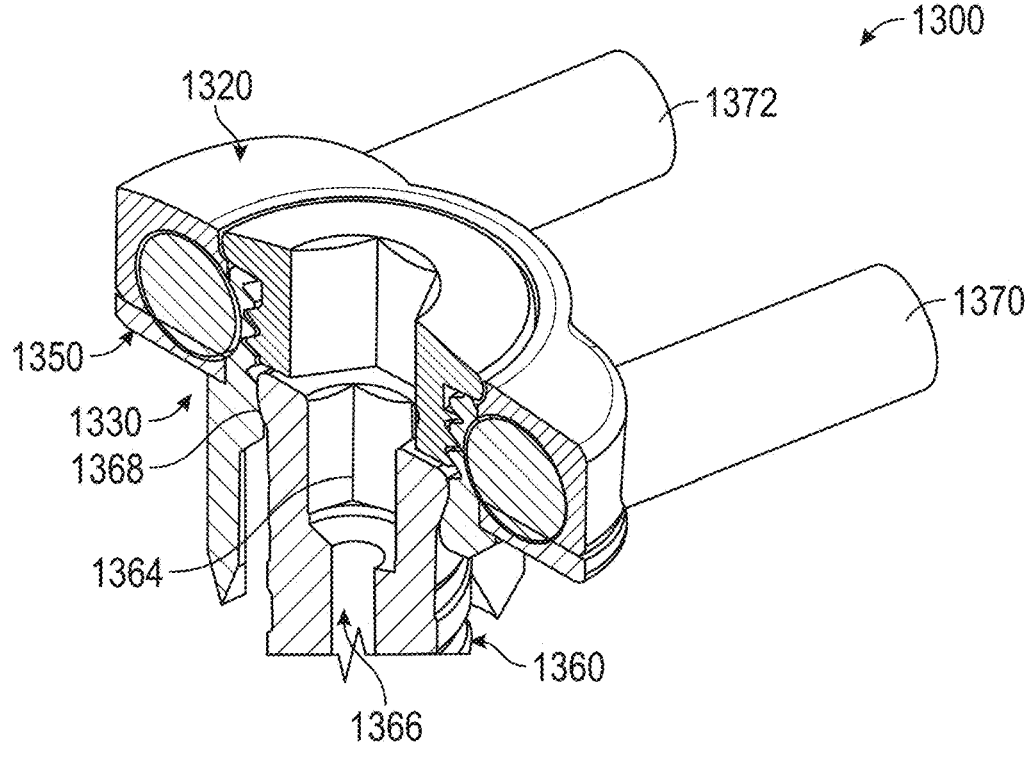

FIG. 8J illustrates a variation of bone anchor 800 that includes barbed anchor spikes 811. In this example, the barded anchor spikes 811 form a triangular spike with bards on the outer radiused surface. In this example, the outer radiused anchor spike surface match the overall radius of the cylindrical body 820. The bone anchor 800 illustrated in FIG. 8J can include all of the other features discussed in reference to FIGS. 8A-8I FIGS. 9A-9F are various views of a threaded bone anchor 900 for use with various bone screws discussed herein. The threaded bone anchor 900 is another bone anchor design to enhance the overall strength of an implant used for spinal tethering. The threaded bone anchor 900 can reduce screw plow and is designed to be implanted ahead of a corresponding bone screw. In this example, the threaded bone anchor 900 includes a cylindrical body 910 forming a screw passage 914. The cylindrical anchor body 910 includes anchor threads 930 disposed on an outer sidewall surface. The anchor threads 930 can include cutting flutes 920 and terminate along a chisel edge 922. The anchor threads 930 extend distally from an upper rim of the cylindrical anchor body 910 that includes an instrument groove 940 around the outer circumference and a screw engagement surface 912 around an inner circumference. The screw engagement surface 912 can be a chaffered or radiused surface designed to receive an outer surface of a distal portion of a bone screw head. In some examples (not illustrate), the instrument groove 940 can include vertical grooves or interruptions to assist with rotational grip for an implant instrument.

FIGS. 10A-10H are various views of an implant 1000 that includes an offset single cord clamp 1010 for use in creating a spinal tether construct. The offset cord clamp 1010 enables full or partial assembly of the implant 1000 outside the body prior to implantation. In certain examples, the offset cord clamp 1010 is assembled onto the cord outside the body as discussed in greater detail below in reference to FIGS. 19 and 20. All of the implants discussed in reference to FIGS. 10A-18H are designed for use in either a partially assembly implant procedure or a fully assembled implant procedure discussed below. The implants assist in eliminating the challenges of threading a spinal cord into implants already placed in the vertebral bodies.

In this example, the implant 1000 includes an offset cord clamp 1010 and bone screw 1060. The offset cord clamp 1010 includes a set screw 1015, an upper clamp body 1020, a lower clamp body 1030 and a cord clamp washer 1050. The set screw 1015 is received into the screw passage 1024 in the upper clamp body 1020, passes through the body ring 1054 of the cord clamp washer 1050 and engages the internal threads 1034 of the receiver cylinder 1032 in the lower clamp body 1030. The cord 1070 is received within cord passage 1022 of the upper clamp body and held in place by the lower cord interface 1052 of the cord clamp washer 1050. The upper clamp body 1020 includes a set screw lip 1026 extending around an inner circumference of the screw passage 1024 that interfaces with the inferior circumferential edge of the set screw head 1017. The interface between the set screw lip 1026 and the set screw head 1017 generates a compressive force on the offset cord clamp 1010. In this example, the lower clamp body 1030 includes a washer interface 1040 to receive the body ring 1054 of the cord clamp washer 1050, so that when the set screw 1015 is tightened into the lower clamp body 1030, the cord 1070 is compressed between the cord passage 1022 of the upper clamp body 1020 and the lower cord interface 1052 of the cord clamp washer. The set screw 1015 can include a driver interface 1018 and an instrument bore 1019 within the driver interface 1018. The driver interface 1018 enables engagement of a driver instrument to tighten the set screw 1015, while the instrument bore 1019 allows passage of a second driver instrument to engage a driver interface 1064 on the bone screw 1060. The through bore design on the set screw 1015 is one of the features that enables the implant 1000 to be fully assembled outside the patient's body (ex situ).

In this example, the lower clamp body 1030 includes an integrated anchor 1042. The integrated anchor 1042 includes anchor spikes 1044 extending distally for implantation into a vertebral body. The lower clamp body 1030 also includes the receiver cylinder 1032 that includes internal threads 1034, screw head seat 1036, and cord groove 1038. The internal threads 1034 extend helically downward from the upper lip of the receiver cylinder 1032 and terminate at the screw head seat 1036. The screw head seat 1036 is adapted to receive a portion of a screw head 1062 of the bone screw 1060. In this example, the bone screw 1060 includes a head flare 1068 that includes a radiused outer surface, and the screw head seat 1036 includes a corresponding concave radiused surface. The screw head seat 1036 is designed to allow for some poly-axial movement of the bone screw 1060 within the lower clamp body 1030. The outer sidewall of the receiver cylinder 1032 includes a cord groove 1038 that when assembled onto the cord 1070 engages a side of the cord 1070. In this example, the cord groove 1038 has a concave radius that approximates the diameter of the cord 1070.

Finally, implant 1000 includes a bone screw 1060 that is used to secure the implant 1000 to a vertebral body. The bone screw 1060 includes a screw head 1062, a driver interface 1064 and a fenestration 1066. The fenestration 1066 allows for use of K-wire guides during implantation. As noted above, the screw head 1062 includes a head flare 1068 portion that engages with the lower clamp body 1030.

FIGS. 11A-11G are various views of an implant 1100 that includes an offset single cord clamp 1110 with dual bone screws. In this example, an offset cord clamp 1100 with characteristics similar to offset cord clamp 1000 discussed above but including dual bone screws to further enhance the strength of a spinal tether construct. The implant 1100 is illustrated with a standard and a small screw (e.g., FIG. 11A) as well as with two standard diameter screws (e.g., FIG. 11B). As the overall design of implant 1100 is not dramatically affected by different screw sizes, the description applies equally to the different screw sizes.

In these examples, the implant 1100 includes the offset cord clamp 1110, a first bone screw 1160 and a second bone screw 1180. The first bone screw 1160 is structured similar to bone screw 1060 discussed above and also engages the offset cord clamp 1110 in a manner similar to that discussed above. The first bone screw 1160 includes a screw head 1162, a driver interface 1164, and a fenestration 1166. The screw head 1162 includes a head flare 1169 that engages with a first screw head seat 1136 in a lower clamp body 1130. The second bone screw 1180 also includes a screw head 1182, a driver interface 1184, and a fenestration 1186 (but only in the larger diameter versions). The screw head 1182 also includes a head flare 1188 that engages a second screw seat 1149 in the lower clamp body 1130.

In this example, the offset cord clamp 1110 can include a set screw 1115, an upper clamp body 1120, a lower clamp body 1130, and a cord clamp washer 1150. The set screw 1115 includes set screw threads 1116, a set screw head 1117, a driver interface 1118, and an instrument bore 1119 (structure is similar to set screw 1015 discussed above). The upper clamp body 1120 is also similar to upper clamp body 1020 discussed above. The upper clamp body 1120 includes a cord passage 1122 to receive cord 1170. The upper clamp body 1120 also includes a screw passage 1124 to receive the first bone screw 1160. The upper clamp body 1120 further includes a set screw lip 1126 extending from an inner circumference of the screw passage 1124, which is formed in a cylindrical portion of the upper clamp body 1120.

The lower clamp body 1130 includes a receiver cylinder 1132 forming a first screw passage 1135 with internal threads 1134 along the inner sidewall. The receiver cylinder 1132 also includes a first screw head seat 1136 formed along an internal distal circumference of the receiver cylinder 1132. The receiver cylinder 1132 also includes a cord groove 1138 disposed on an external sidewall. The base of the lower clamp body 1130 includes a washer seat 1140 to receive the cord clamp washer 1150. The lower clamp body 1130 further includes an integrated anchor 1142 with anchor spies 1144. In this example, the lower clamp body 1130 extends laterally to include a second screw passage 1148 with a second screw seat 1149 formed around an inner circumference of the screw passage 1148. The cord clamp washer 1150 includes a lower cord interface 1152 and a body ring 1154. The cord clamp washer 1150 is assembled over the receiver cylinder 1132 and down onto the washer seat 1140.

FIGS. 12A-12D are various views of implant 1200 including an offset dual cord clamp 1210. The implant 1200 is another variation on implant 1000, this variation adds the ability to incorporate a second cord to a spinal tether construct. Various structures discussed in reference to implant 1200 are similar to corresponding structures in implant 1000, and much of the descriptions are interchangeable. For example, the implant 1200 includes a lower clamp body 1230 that integrates the cord washer 1050 discussed above but is otherwise a very similar structure. The implant 1200 is designed for both partial and fully assembled implantation as described below.

In this example, the implant 1200 includes an offset cord clamp 1210, a bone screw 1260, an inner cord 1270 and an outer cord 1272. The offset cord clamp 1210 includes an upper clamp body 1220 and a lower clamp body 1230 held together with a set screw 1215. The upper clamp body 1220 includes an inner cord passage 1222, a screw passage 1224, and an outer cord passage 1228. In certain examples, the upper clamp body 1220 and the lower clamp body 1230 can include engagement features that allow these structures to snap together allowing the set screw to be inserted later in the procedure. The inner cord passage 1222 and outer cord passage 1228 are designed to receive a particular diameter cord and include large clamping surface areas to enhance the ability of the implant 1200 to grip the inner cord 1270 and the outer cord 1272. In an example, the inner cord passage 1222 and the outer cord passage 1228 can include cord relief cutouts 1229. The screw passage 1224 forms a large cylinder that includes a set screw lip 1226 around an upper circumference. The set screw lip 1226 engages the set screw head 1217 to secure the upper clamp body 1220 to the lower clamp body 1230 and capture the inner cord 1270 and the outer cord 1272 within the respective cord passages.

The lower clamp body 1230 includes receiver cylinder 1232 that receives the upper clamp body 1220 on an outer surface and includes internal threads 1234 to receive the set screw 1215 on an inner surface. The receiver cylinder 1232 also includes a screw head seat 1236 around a lower inner circumference to receive a screw head 1262 of bone screw 1260. The receiver cylinder 1232 can also include a cord groove 1238 around the outer circumference, the cord groove 1238 can include a concave radius similar to the outer diameter of the inner cord 1270. In certain examples, the outer surface of the receiver cylinder 1232 is designed to generate a friction fit with the inner surface of the screw passage 1224 of the upper clamp body 1220, which allows for temporary assembly without the set screw 1215. Finally, the lower clamp body 1230 includes a cord interface surface 1240 that extends laterally from the receiver cylinder 1232 to function in conjunction with the inner cord passage 1222 and the outer cord passage 1228 to capture the inner cord 1270 and the outer cord 1272. In this example, the lower clamp body 1230 is illustrated without an integrated anchor, but the lower clamp body 1230 can include an integrated anchor or the implant 1200 can be used with any of the standalone anchors discussed herein. An integrated anchor version of implant 1200 would resemble implant 1000 discussed above.

FIGS. 13A-13F are various views of an implant 1300 including a symmetric offset dual cord clamp 1310 designed to secure an anterior cord 1370 and a posterior cord 1372. The implant 1300 is similar in concept and construction as compared to implants 1000, 1100, and 1200 discussed above. Like implant 1200, implant 1300 is designed to secure dual cords. Implant 1200 secures dual cords in an offset configuration, while implant 1300 is symmetric around the bone screw 1360. Both implants 1200 and implants 1300 could be used together in a single spinal tether construct at different levels. For example, an offset implant 1200 might be used at a level where some alternative loading is desirable on a particular vertebral body. Similar to implant 1000, implant 1300 includes a lower clamp body 1330 within an integrated anchor 1342.

In this example, the symmetric offset cord clamp 1310 can include a set screw securing an upper clamp body 1320 onto a lower clamp body 1330 with a cord clamp washer 1350 in between. In another example, the cord clamp washer 1350 may be integrated into the lower clamp body 1330 similar to implant 1200 discussed above. In this example, the set screw 1315 includes set screw threads 1316, a set screw head 1317, a driver interface 1318, and an instrument bore 1319 through the driver interface 1318. The upper clamp body 1330 can include an anterior cord passage 1322, a lower body passage 1324, and a posterior cord passage 1328 on the opposite side of the lower body passage 1324. In this example, the lower body passage 1324 forms a cylindrical bore that includes a set screw lip 1326 around an upper periphery to receive an outer edge of the set screw head 1317 once assembled.

In an example, the lower clamp body 1330 includes a receiver cylinder 1332 that receives cord clamp washer 1350 and the upper clamp body 1320 via the lower body passage 1324. The receiver cylinder 1332 includes internal threads 1334 extending from a superior edge down to a screw seat similar to screw head seat 1236 or screw head seat 1036 discussed above. The receiver cylinder 1332 also includes an outer sidewall with a cord groove 1338 designed to receive the anterior cord 1370 and the posterior cord 1372 once the implant 1300 is assembled onto both cords. The lower clamp body 1330 also includes a washer seat 1340 extending from a lower periphery of a washer interface 1346 formed in distal end of the receiver cylinder 1332. The washer interface 1346 is designed to receive a ring body of the cord clamp washer 1350. Below the washer seat 1340 extends an integrated anchor 1342 including a plurality of anchor spikes 1344. The offset cord clamp 1310 is completed by the cord clamp washer 1350 that includes an anterior cord extension 1352 and a posterior cord extension 1354 which form the base of the anterior cord passage 1322 and the posterior cord passage 1328, respectively.

The offset cord clamp 1310 is secured to a vertebral body with bone screw 1360. The bone screw 1360 includes a screw head 1362, a driver interface 1364, and a fenestration 1366. Similar to bone screw 1060, the screw head 1362 includes a head flare 1368 that interfaces with the screw head set around the distal interior surface of the receiver cylinder 1332.

Similar to implant 1200 discussed above, portions of the lower clamp body 1330, such as the receiver cylinder 1332, can be designed to generate a friction fit with portions of the upper cord clamp 1320. For example, the inner surface of the lower body passage 1324 can generate a friction fit with a portion of the outer surface of the receiver cylinder 1332.

Figures 14A, 14B, 14C:
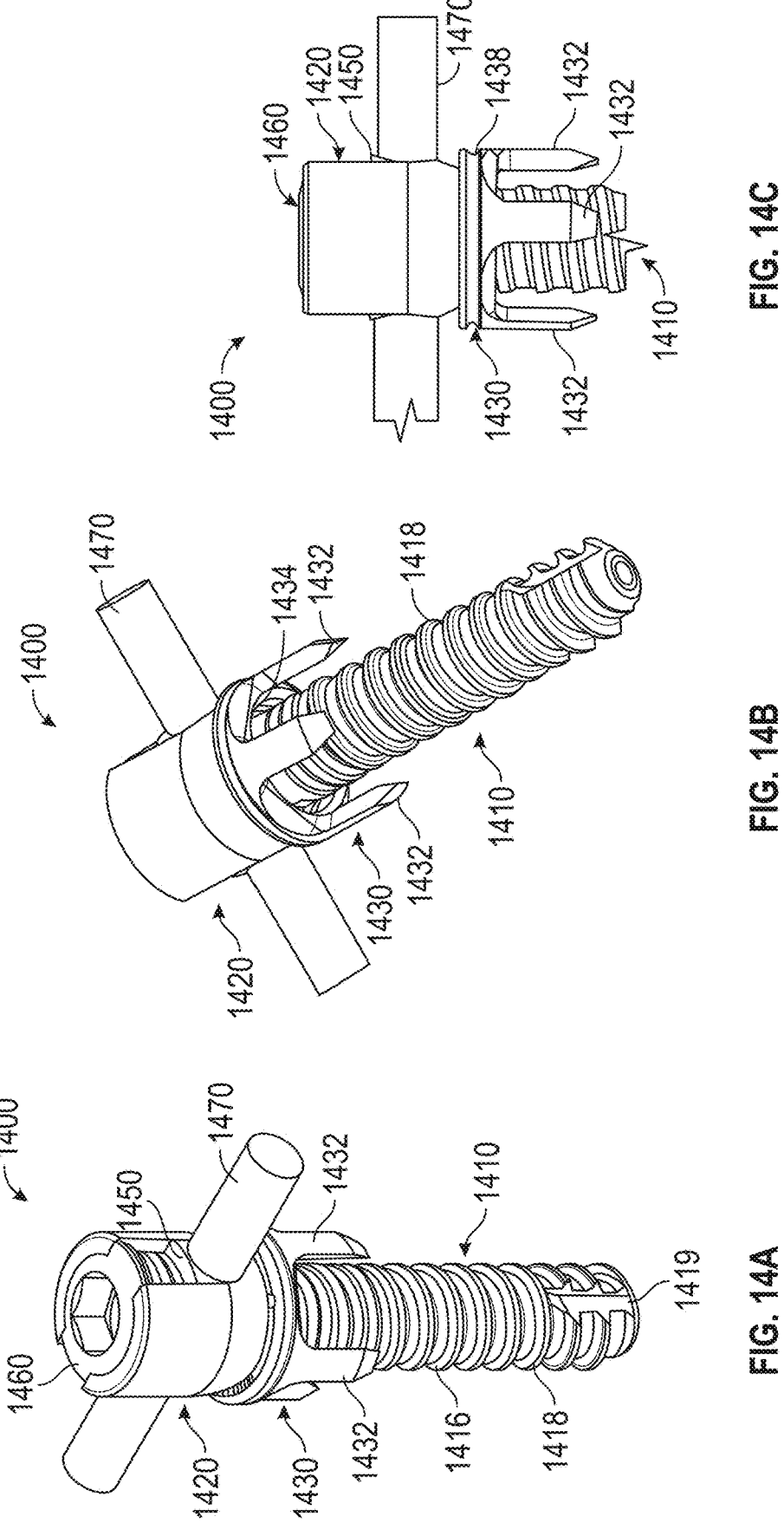
FIGS. 14A-14F are various views of a top loading modular cord clamp implant in accordance with the present disclosure.
Figures 14D, 14E, 14F:
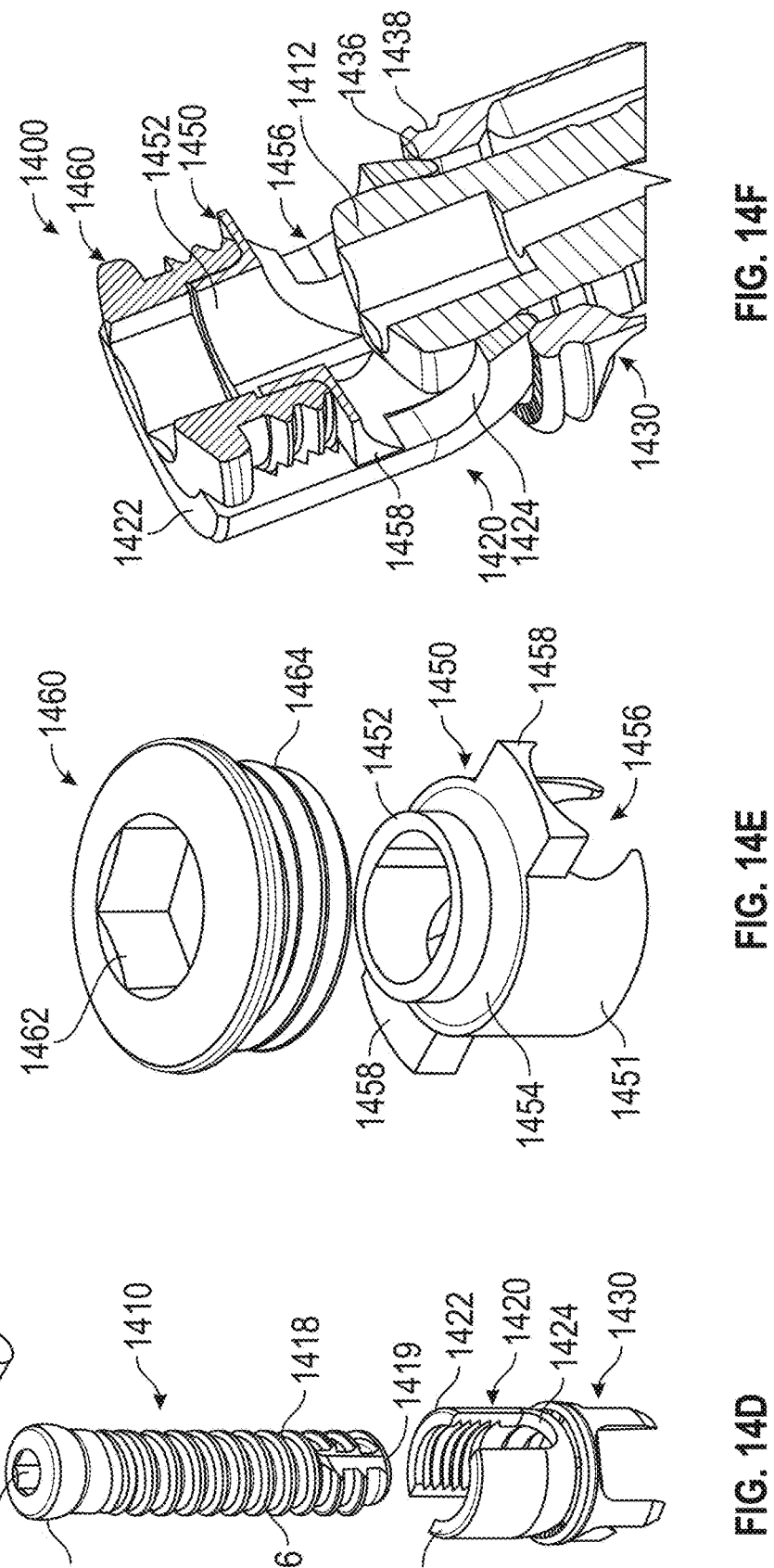

FIGS. 14A-14F are various views of an implant 1400 that includes a top loading modular cord clamp assembly 1450. The implant 1400 is another spinal tethering implant that can be partially for fully assembled ex situ to case overall implantation process. Ex site assembly of the implants can shorten procedure time and ease the overall process by avoiding manipulation of implants and the cord in situ. Partial or full ex situ assembly also enables distraction-based tensioning between the completed implants in each vertebra. In this example, the implant 1400 can include bone screw 1410, saddle body 1420, anchor 1430, cord assembly 1450 and set screw 1460. In some examples, the cord assembly 1450 and set screw 1460 can be provided as a pre-assembled component, such as is shown in FIG. 14D. Additionally, in some examples, the saddle body 1420 and the anchor 1430 can be integrated together or delivered as a pre-assembled component (also as illustrated in FIG. 14D).

FIG. 14D is an example of how implant 1400 may be used in a partially assembled procedure. In this example, the surgeon first implants the combined saddle body 1420 and anchor 1430. Next, the bone screw 1410 is implanted through screw passages 1426, 1434 in the saddle body 1420 and anchor 1430 respectively. Finally, the cord assembly 1450 with set screw 1460 attached is assembled onto cord 1470 ex situ and inserted into saddle body 1420 in situ. Each of the implant components discussed can be implanted via an all-through-one (ATO) port as discussed further below.

In this example, the bone screw 1410 includes a screw head 1412, a driver interface 1414, and a screw shaft 1416 with screw threads 1418. The screw threads can include cutting flutes 1419 on the distal end of the bone screw 1410. The saddle body 1420 can include threaded saddle arms 1422, a cord recess 1424, a screw passage 1426, and a screw seat 1428. The threaded saddle arms 142 and cord recess 1424 for a U-shaped structure with the screw passage 1426 extending through a longitudinal axis. The screw seat 1428 can be a concave surface around a circumference of the screw passage 1426 and is designed to receive a lower surface of the screw head 1412. The anchor 1430 includes anchor spikes 1432 extending inferiorly around the screw passage 1434. The anchor 1430 also includes a saddle interface surface 1436 that is a chaffered or radiused surface around an interior circumference of the anchor 1430. Around an exterior circumference of the anchor 1430 is an instrument groove 1438.

The cord assembly 1450 includes a clamp body 1451 to receive the cord 1470 with a cord passage 1456 and the set screw 1460. The clamp body 1451 can also include cord clamp extensions 1458 to extend the clamping surface of the clamp body 1451. The cord clamp body 1451 also include a set screw cylinder 1452 surrounded by a set screw interface surface 1454. The set screw cylinder 1452 operates to rotatably secure the set screw 1460 to the clamp body 1451 to case implantation of the cord assembly 1450. The set screw interface surface is a donut-shaped flat surface designed to receive the end of the set screw 1460 to distribute forces created by tightening the set screw 1460 into saddle body 1420 onto the cord 1470. The cord assembly 1450 is designed to be coupled to the cord ex situ and then inserted into the saddle body 1420 in situ after the saddle body 1420, anchor 1430, and bone screw 1410 are already implanted. The clamp body 1451 is designed to slide into the cord recess 1424 of the saddle body 1420 and be tightened down with the set screw 1460. The interaction between the clamp body 1451, the saddle body 1420 and the set screw 1460 operate to compress the cord 1470 from all sides and create a distributed cord grip that avoids inducing stresses on to the cord 1470 (as compared to a typical set screw directly on the cord, as an example).

Figure 15C:
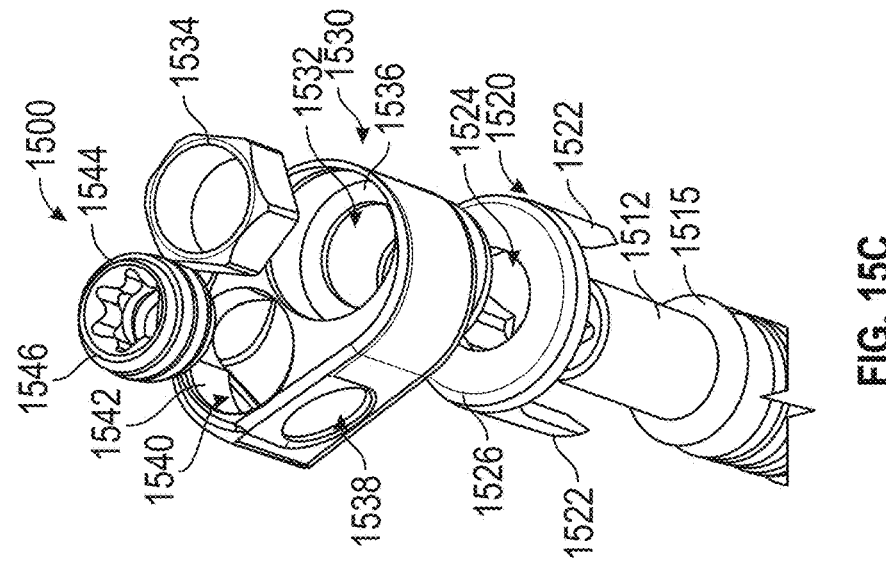
FIGS. 15A-15F are various views of a posted screw modular cord clamp implant in accordance with the present disclosure.
Figure 15B:
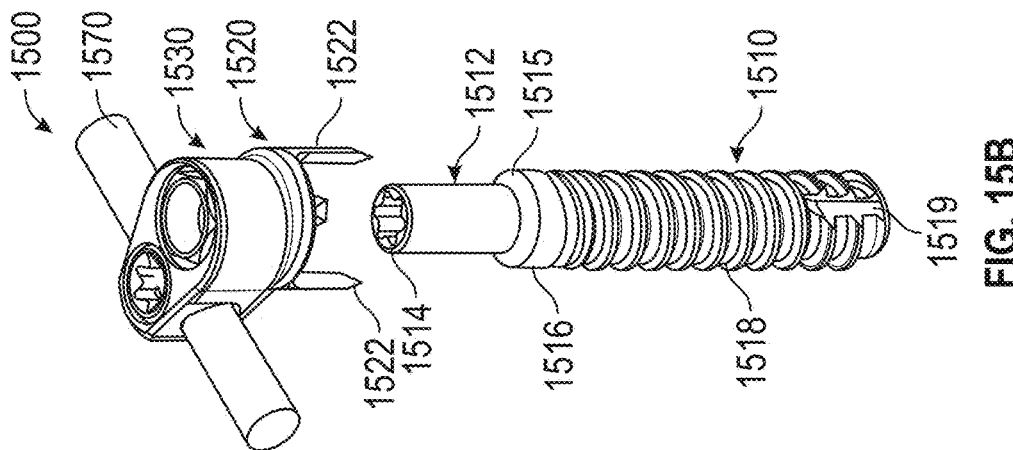
Figure 15A:
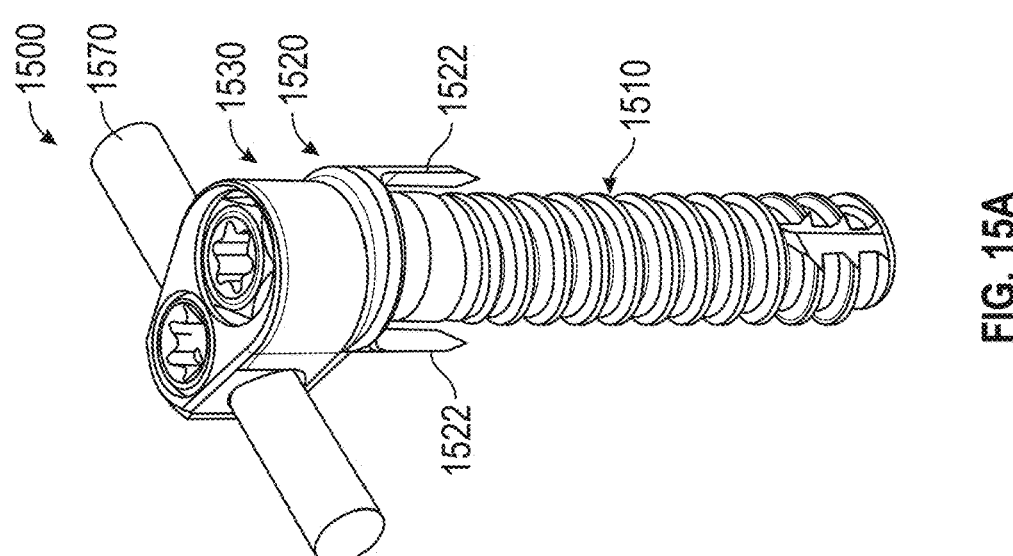
Figures 15D, 15E, 15F:
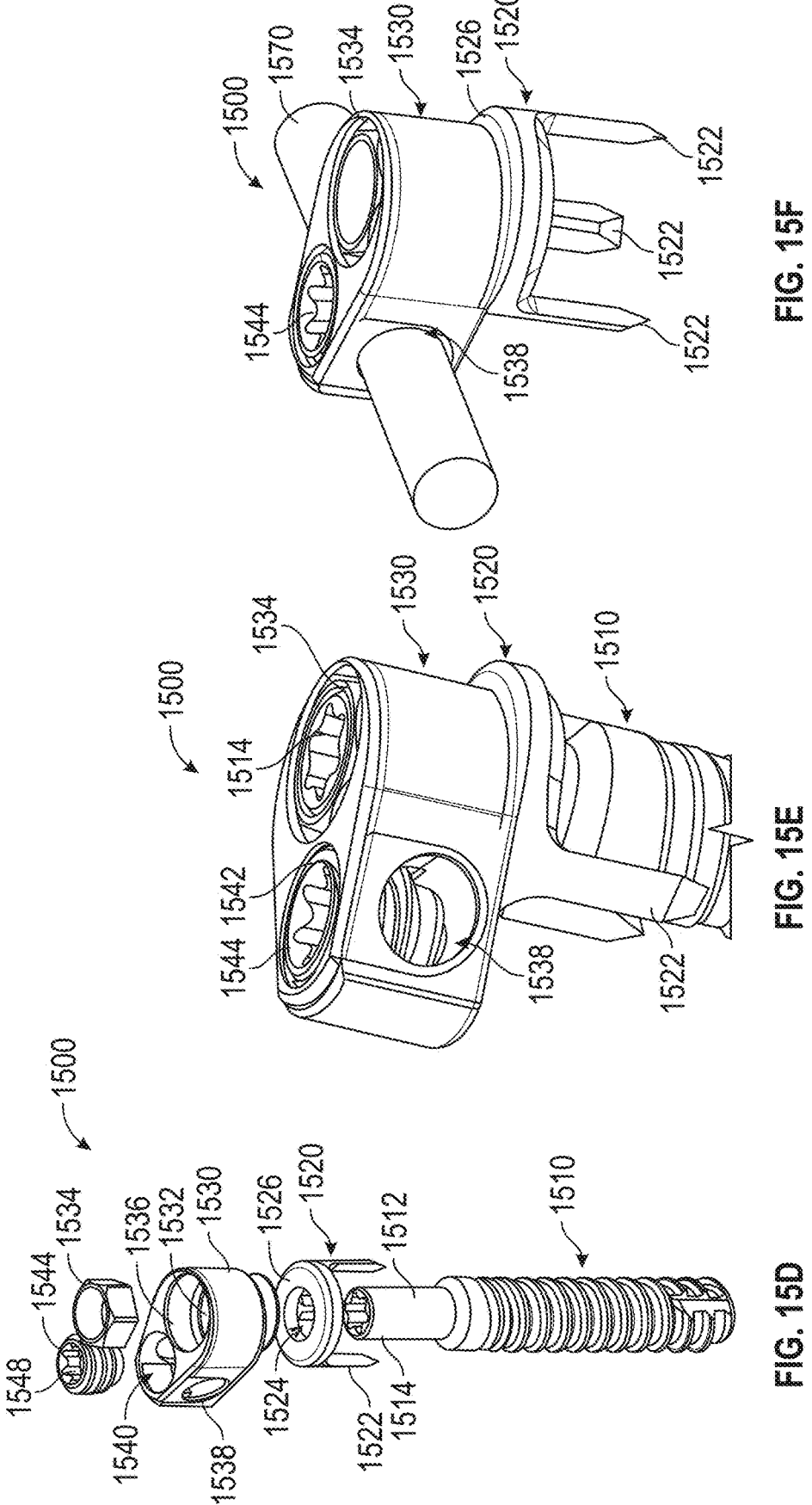

FIGS. 15A-15F are various views of an implant 1500 including a posted screw 1510 and a modular cord clamp (cord assembly 1530). The implant 1500 is design for partially assembled implantation procedure where the posted screw is implanted, and the cord assembly is assembled onto the cord ex situ and then inserted onto the implanted screw. FIG. 15B illustrates the two implantable components of implant 1500.

In this example, the implant 1500 includes a bone screw 1510, an anchor 1520, and a cord assembly 1530. As noted above, in some examples the anchor 1520 is integrated into the cord assembly, or at least implanted in the step of the implantation technique. In an example, the bone screw 1510 is a posted bone screw with a threaded screw head 1512, a driver interface 1514, a screw shoulder 1515, a screw shaft 1516, screw threads 1518, and cutting flutes 1519. The screw shoulder 1515 is designed to receive/engage an inferior surface around an inner circumference of the screw passage 1524 of the anchor 1520. The anchor 1520 can include anchor spikes 1522, the screw passage 1524, and a cord assembly interface surface 1526.

In this example, the cord assembly 1530 includes a screw head passage 1532, a head nut 1534, a nut seat 1536, a set screw passage 1540, an interior threaded sidewall 1542, and a set screw 1544. The screw head passage 1532 is designed to receive the threaded screw head 1512 through a distal bore created by the nut seat 1536 and the head nut 1534 through the proximal opening. The head nut 1534 is designed to lock the cord assembly 1530 onto the bone screw 1510 via the threaded screw head 1512. The cord passage 1538 is designed to receive a cord or tether for the spinal tether construct and includes a superior open formed by the set screw passage 1540. The cord passage 1538 includes a section of interior threaded sidewall on opposing sides of the set screw passage 1540 to engage the set screw threads 1546 as the set screw 1544 is threaded into the passage to compress the cord and lock it in place. The set screw 1544 is tightened via a set screwdriver interface 1548. In this example, the cord assembly 1530 includes a distal anchor engagement cylinder that fits into the screw passage

1524 of the anchor 1520. In some examples, the distal anchor engagement cylinder can create a fiction fit with the anchor 1520 to enable the anchor 1520 to function as an integral part of the cord assembly 1530.

As is the case with most of the implants discussed herein, implant 1500 includes numerous components that could be interchanged with similar components discussed in reference to other example implants. For example, anchor 1520 could be exchanged for any of the various anchors discussed herein.

FIGS. 16A-16H are various views of a top loading self-locking cord clamp implant 1600. The implant 1600 illustrated in these figures includes two basic components saddle body 1620 and cord assembly 1630. The saddle body 1620 represents any tulip style pedicle screw head and is shown in these figures without a bone screw for clarity. The saddle body 1620 in this example includes threaded saddle arms 1622 to receive a set screw, such as set screw 1640. The saddle body 1620 also includes a cord recess to receive the cord assembly 1630 and screw passage 1626 with a screw seat 1628 around the circumference of the opening forming the screw passage 1626. The cord assembly 1630 can be used with any tulip-style head bone screw.

The focus of implant 1600 is the cord assembly 1630 that is designed to enable partially assembled implant techniques where the cord assembly is put on the cord 1610 ex situ and then the cord 1610 and cord assembly are implanted into a bone screw with saddle body 1620 and optionally an anchor. The cord assembly 1630 in this example includes an outer cord clamp housing 1632 coupled to a set screw 1640. The outer cord clamp housing 1632 includes a set screw passage 1633, a cord passage 1634, cord clamp extensions 1636, an inner cord clamp 1638, and a bias member 1639. In an example, the inner cord clamp 1638 is spring biased (by bias member 1639) to automatically lock the cord assembly onto the cord 1610. In an example, the bias member 1639 is a coil spring or similar bias device positioned around the base of the inner cord clamp 1638. The set screw 1640 includes a clamp interface 1642 in the form of a cylindrical extension that couples into the set screw passage 1633 and allows for manual displacement of the inner cord clamp 1638 to release the cord 1610 (or facilitate inserting the cord assembly 1630 onto the cord 1610).

Figures 16A, 16B, 16C:
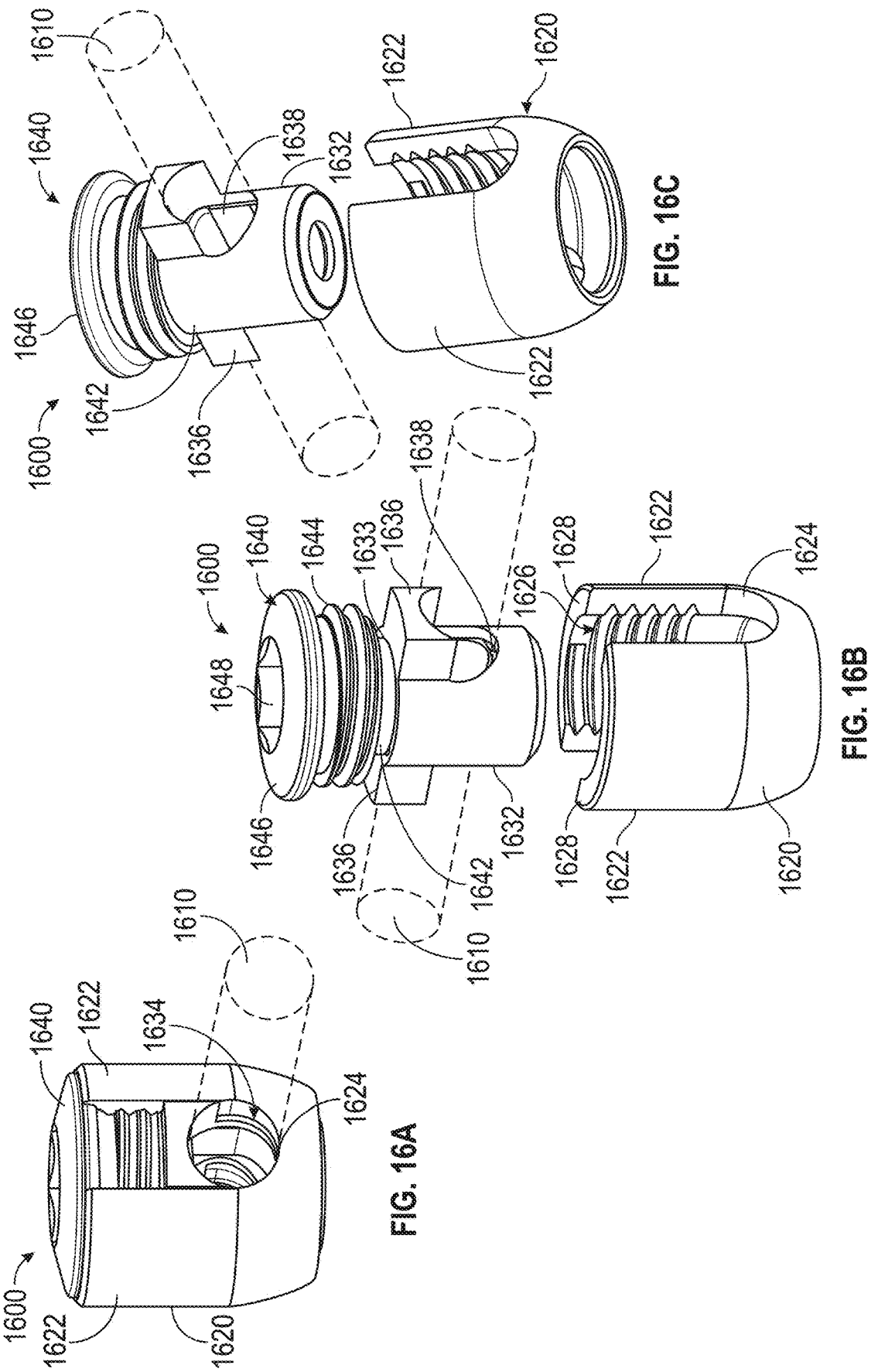
FIGS. 16A-16H are various views of a top loading self-locking cord clamp implant in accordance with the present disclosure.
Figures 16D, 16E, 16F, 16G, 16H:
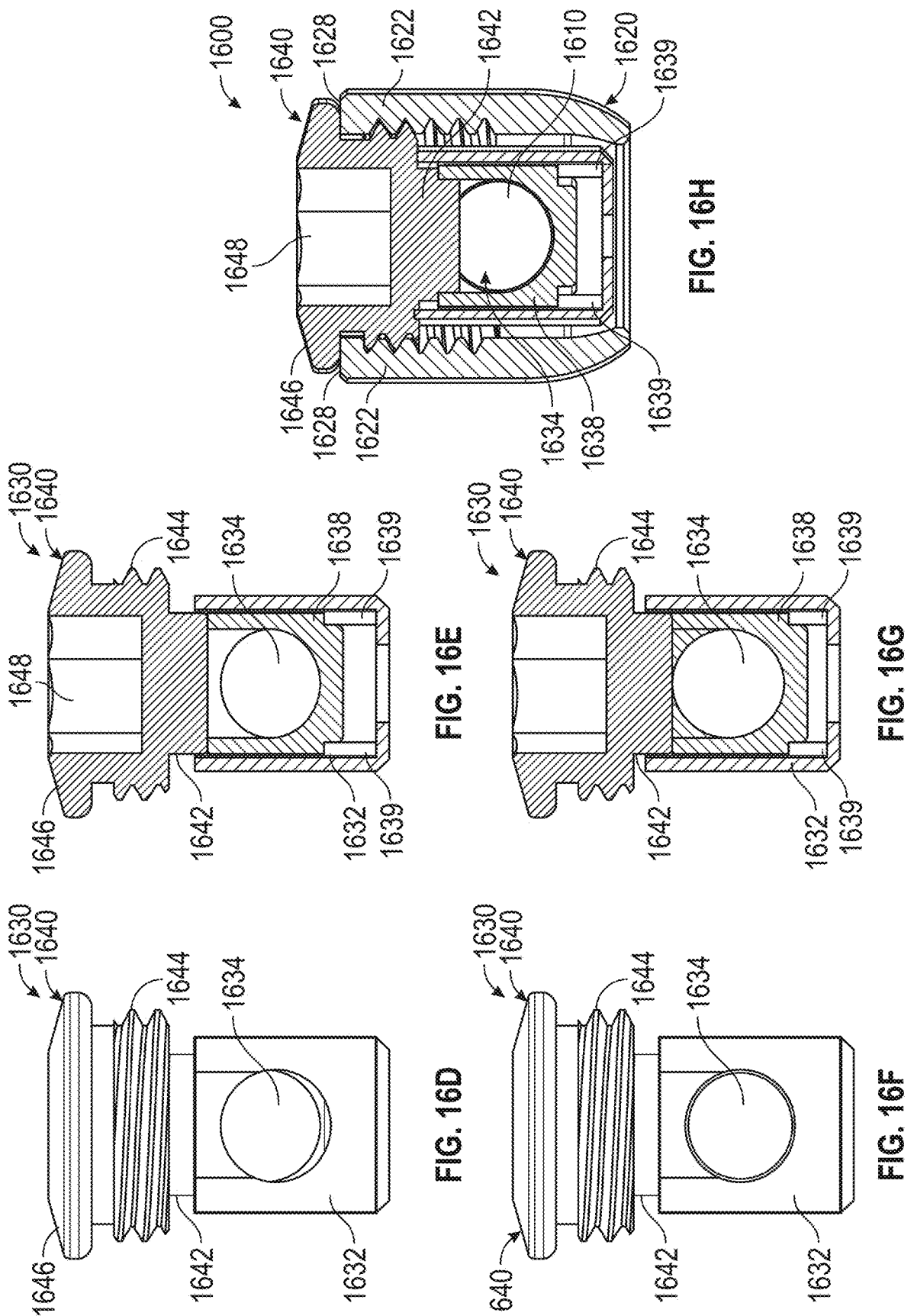
Figures 17A, 17B, 17C:
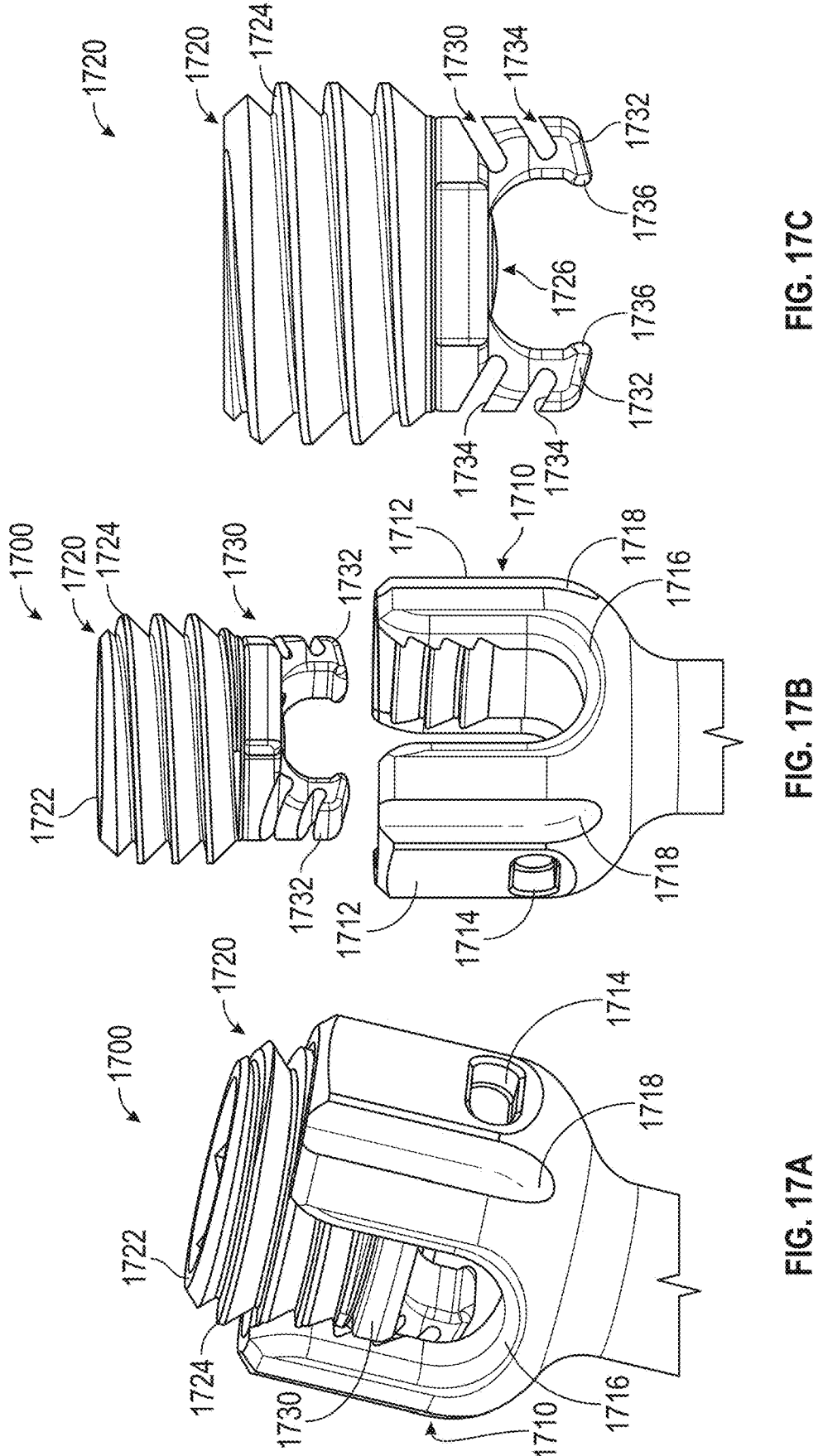
FIGS. 17A-17F are various views of a cord clamping set screw in accordance with the present disclosure.
Figures 17D, 17E, 17F:
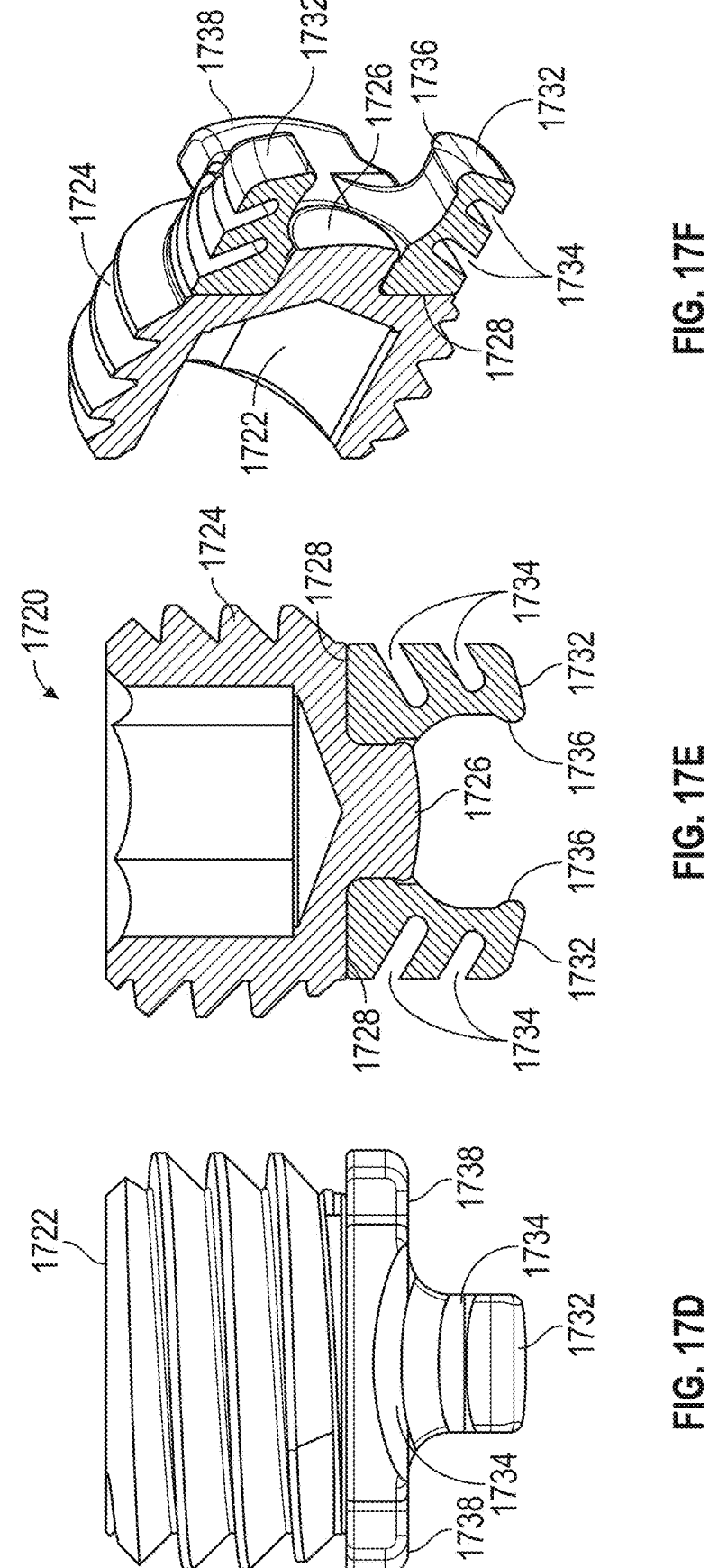

FIGS. 16D and 16E are illustrations of the cord assembly 1630 and set screw 1640 with the inner cord clamp 1638 biased in a close or locked position on the cord 1610. In FIG. 16E the bias member 1639 is illustrated as elongated boxes to indicate that the spring or similar structure is pushing the inner cord clamp 1638 against the cord 1610. FIGS. 16F and 16G illustrate the cord assembly and set screw 1640 with the inner cord clamp 1638 in an open or unlock position to allow for free movement of the cord 1610 through the cord assembly 1630. FIG. 16G illustrates the bias member 1639 in a compressed position as the inner cord clamp 1638 is being pushed away from engagement with the cord. In an example, the inner cord clamp 1638 can be disengaged from the cord 1610 by application of a force downward on the set screw counteracting the bias member 1639. FIG. 16H is a cross-sectional view of the cord assembly 1630 inserted into the saddle body 1620 and the set screw 1640 fully tightened down. In the fully tightened down position, the set screw 1640 compresses the cord 1610 to fully lock it into the implant 1600. In this example, the head 1644 of the set screw 1640 limits how much compression of the cord 1610 is possible within implant 1600. In some examples, the set screw 1640 and cord assembly 1630 are designed to allow for dynamic cord slip above a pre-define cord tension.

FIGS. 17A-17F are various views of a cord clamping set screw assembly (cord assembly 1720). The implant 1700 includes a bone screw with a saddle body 1710 and a cord assembly 1720 that clamps a cord within the saddle body 1710. The bone screw including the saddle body 1710 further includes a pair of threaded saddle arms 1712, instrument interfaces 1714, a cord recess 1716, and instrument grooves 1718 in each corner of the saddle body 1710. The saddle body 1710 is representative of any tulip-style pedicle screw head and the cord assembly 1720 can be adapted for use within any similar spinal bone screw assembly.

The cord assembly 1720 includes set screw 1722 and cord clamp 1730. The cord clamp 1730 attaches to the set screw 1722 via clamp peg 1726 extending from a distal surface of the set screw 1722. The clamp peg 1726 is received into a central bore in the cord clamp 1730 and the set screw 1722 distributes clamping forces onto the cord clamp 1730 via a cylindrical mating surface 1728. The clamp peg 1726 enables the set screw 1722 to rotate relative to the cord clamp 1730 to facilitate engaging the cord assembly with the saddle body 1710. The cord clamp 1730 further includes clamp arms 1732. The clamp arms 1732 include flex grooves 1734 and terminate in clamping tips 1736. The cord clamp 1730 can also include clamp washer extensions 1738 to extend the cord clamping surface area of the cord clamp 1730. The clamp arms 1732 are designed to be compressed onto a cord when the cord assembly is inserted into the saddle body 1710 and the set screw 1722 tightened via threads 1724 engaging with the threaded saddle arms 1712. The flex grooves 1734 allow the clamp arms 1732 to flex outward to accept a cord in between the clamp arms 1732. The cord assembly 1720 is designed to be attached to a cord ex situ and then the cord and cord assembly 1720 implanted into a bone screw with saddle body 1710 already implanted into the vertebral body.

FIGS. 18A-18H are various views of another cord clamping set screw type implant 1800. In this example, the implant 1800 includes a saddle body 1810 and a cord assembly 1820. Again, the saddle body 1810 is representative of any tulip-style pedicle screw that might be used in a typical spinal fusion procedure. In this example, the saddle body 1810 does include a couple structures that might be specific to implant 1800, such as the oval clamp recess 1818 and fenestration 1819. The saddle body 1810 in this example also includes a pair of threaded saddle arms 1812, instrument interfaces 1814, a cord recess 1816, and instrument grooves 1817.

Figures 18A, 18B, 18C, 18D:
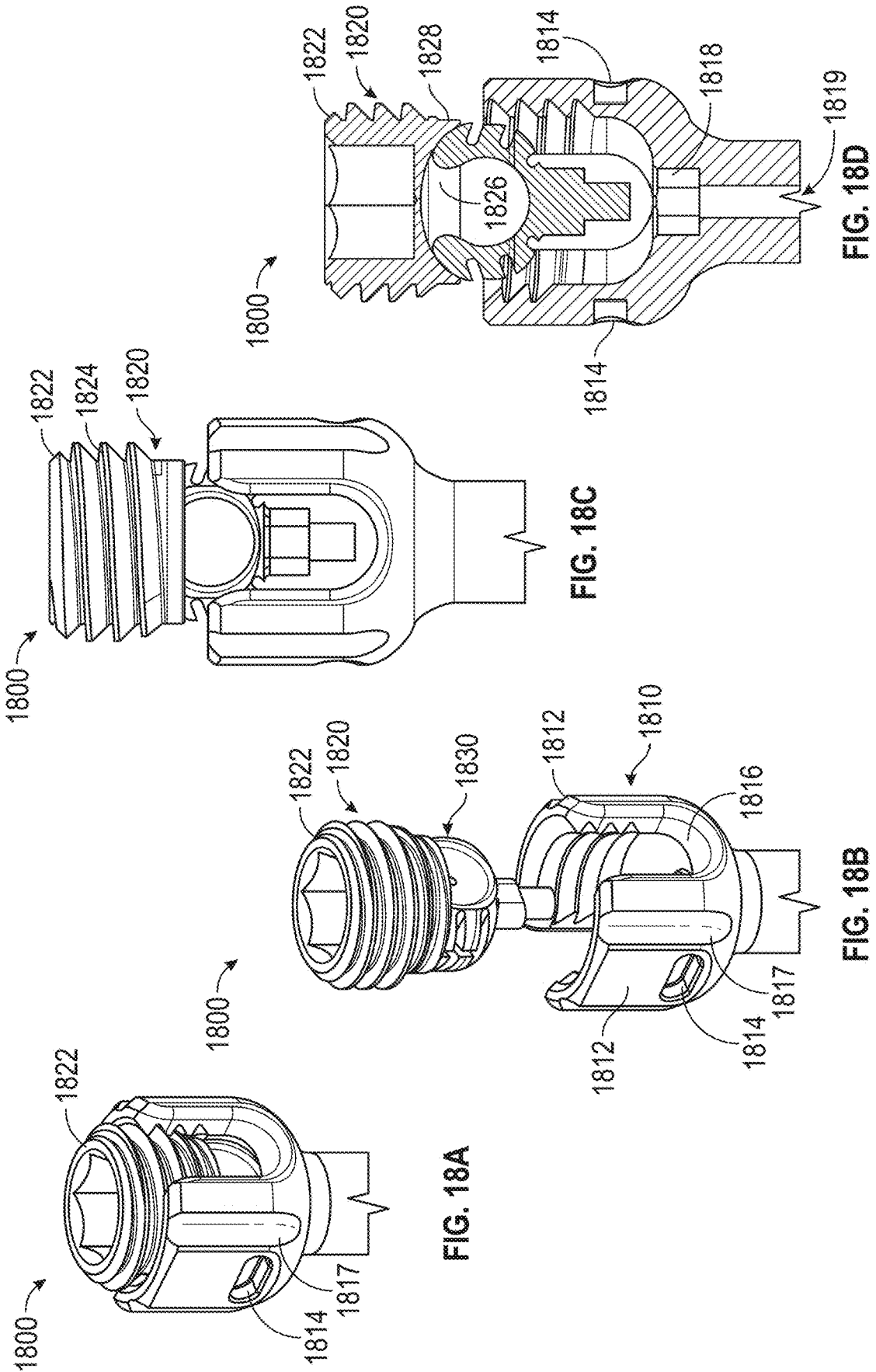

In this example, the cord assembly 1820 includes a set screw 1822 and a cord clamp 1830. The set screw 1822 can couple to the cord clamp 1830 via a spherical concave clamping surface 1826 (as shown in FIGS. 18B and 18D). The set screw 1822 also includes external threads 1824 and a cylindrical mating surface 1828 around an outer distal edge of the set screw 1822 below the external threads 1824. The cord clamp 1830 can include clamp arms 1832, oval alignment extension 1838, and a cylindrical guide peg 1836. The clamp arms 1832 are designed with sufficient flex due to the flex grooves 1834 to receive a cord and hold position on the cord. The cord clamp 1830 is designed to be fabricated from an at least somewhat flexible material, such as Teflon, polyetheretherketone (PEEK) or similar dimensionally stable thermoplastic with characteristic acceptable for implantation into the human body. In other examples, the cord clamp 1830 can be fabricated from metallic materials such as nitinol or titanium. The cylindrical guide peg 1836 and oval alignment extension 1838 features assist in implanting the cord assembly 1820 into the saddle body

1810. The cylindrical guide peg 1836 can first find the oval clamp recess 1818 and then be guided into fenestration 1819 while the oval alignment extension 1838 fit snuggly into the oval clamp recess 1818. Once the cord assembly 1820 is aligned into position in the saddle body 1810, the set screw 1822 is used to tighten the implant 1800 with the concave clamping surface 1826 compressing the clamp arms 1832 around the cord to secure it in position relative to the saddle body 1810.

Figure 19:
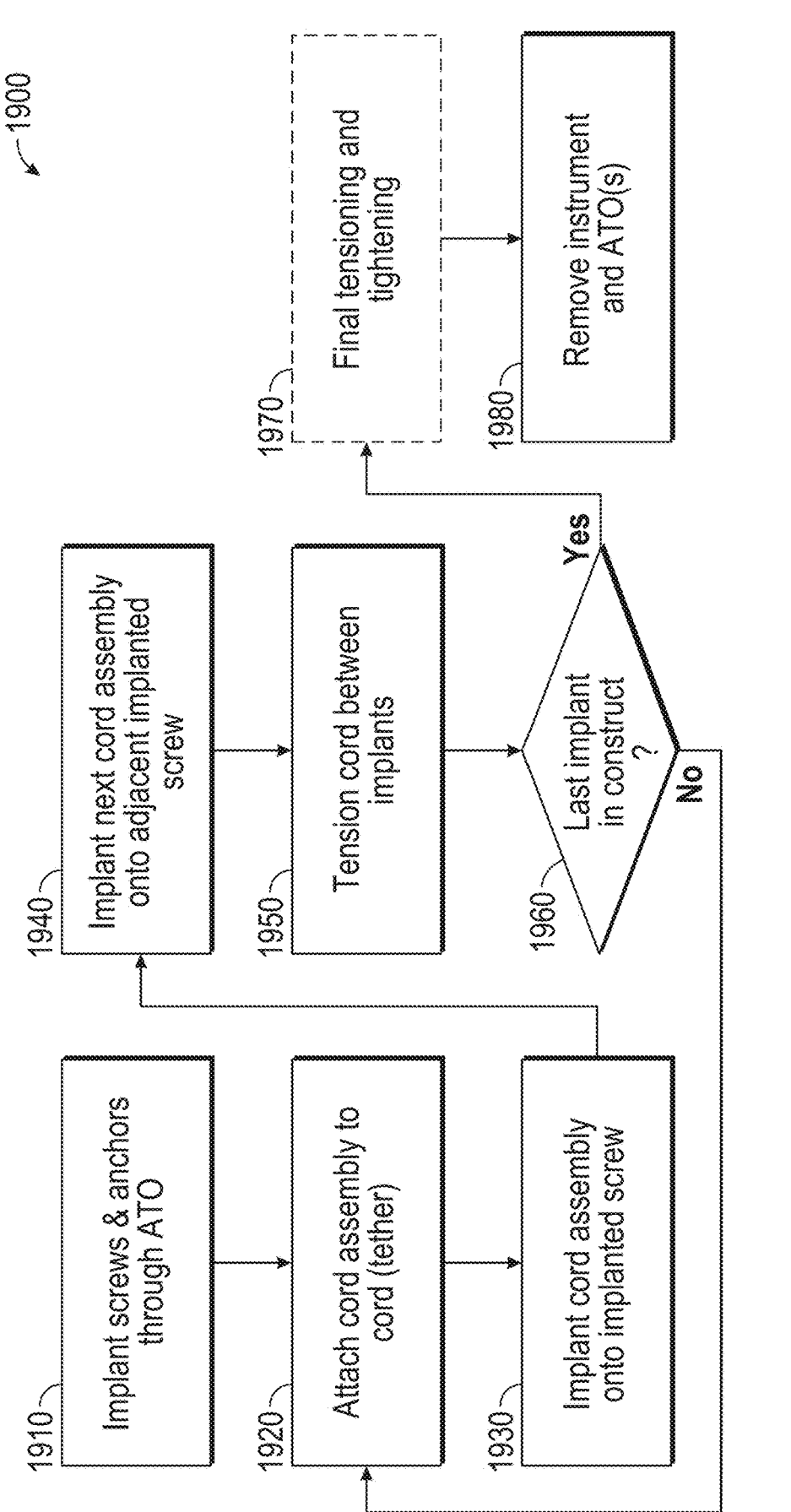
FIG. 19 is a flowchart illustrating a technique for using partially assembled implants in a spinal tethering procedure in accordance with the present disclosure.

FIG. 19 is a flowchart illustrating a technique 1900 for using partially assembled implants in a spinal tethering procedure. Most of the implants discussed above are usable in the technique 1900, such as implants 1000, 1100, 1200, 1300, 1400, 1500, 1600, 1700, 1800, and 2300 (discussed in reference to FIGS. 23A-23G below). The technique 1900 is discussed below in reference to implant 1600, and more specifically in reference to cord assembly 1630. The partially assembled implant technique involves first implanting all of the bone screws or similar implants into the target vertebral bodies that will be part of the spinal tether construct. After the bone screws are implanted, the cord assembly implants are assembled onto the cord ex situ, then the cord with the cord assembly implants are inserted into the already implanted bone screws. The cord assembly implants may all be put on the cord at once or may be assembled onto the cord one by one as they are implanted into the bone screws.

In this example, the technique 1900 can being at 1910 with the surgeon implanting bone screws with or without anchors through one or more all-through-one (ATO) ports. The bone screws implanted at operation 1910 can include the bone screw 850 with expanding anchor 810 for example. The bone screw 850 includes a saddle body comparable to saddle body 1620 and would be compatible with cord assembly 1630. At 1920, the technique 1900 continues with the surgeon attaching at least two cord assemblies 1630 to a cord 1610 (note, this could be done one at a time, but this particular version of the technique 1900 does it two at a time). The technique 1900 continues at 1930 with the surgeon inserting the first cord assembly 1630 attached to cord 1610 through the ATO and into saddle body 1620 in the first bone screw 850 in the tether construct. Next, the technique 1900 continues at 1940 with the surgeon positioning the second cord assembly 1630 attached to the cord 1610 into the second saddle body 1620 of the second bone screw 850. At 1950, the technique 1900 continues with the surgeon tensioning the cord 1610 between the first bone screw and the second bone screw. Tensioning can include tightening the set screws associated with each of the first and second cord assemblies 1630.

Once the first set of two cord assemblies 1630 are implanted and tensioned, the technique 1900 continues at 1960 with the surgeon determining whether the last bone screw in the construct has been reached. If the last bone screw has not had a cord assembly inserted, then the technique 1900 loops back through operations 1920 to 1960 until the cord has been implanted into each bone screw with a cord assembly and at least initially tensioned. Note, after the initial pass-through operations 1920 through 1960, one cord assembly at a time can be assembled onto the cord and the surgeon can progress through the tether construct one bone screw at a time. Back at 1960, the technique 1900 continues on after the last bone screw in the construct is coupled to the cord 1610 to operation 1970. At 1970, the technique 1900 optionally continues with final tensioning and tightening of set screws in the implanted cord assemblies. Final tensioning can involve loosening and re-tightening each set screw while applying distraction pressure between adjacent bone screws. Finally, once the construct has been sufficiently tensioned, the technique 1900 completes at 1980 with removal of all instruments and ATOs from the patient.

Figure 20:
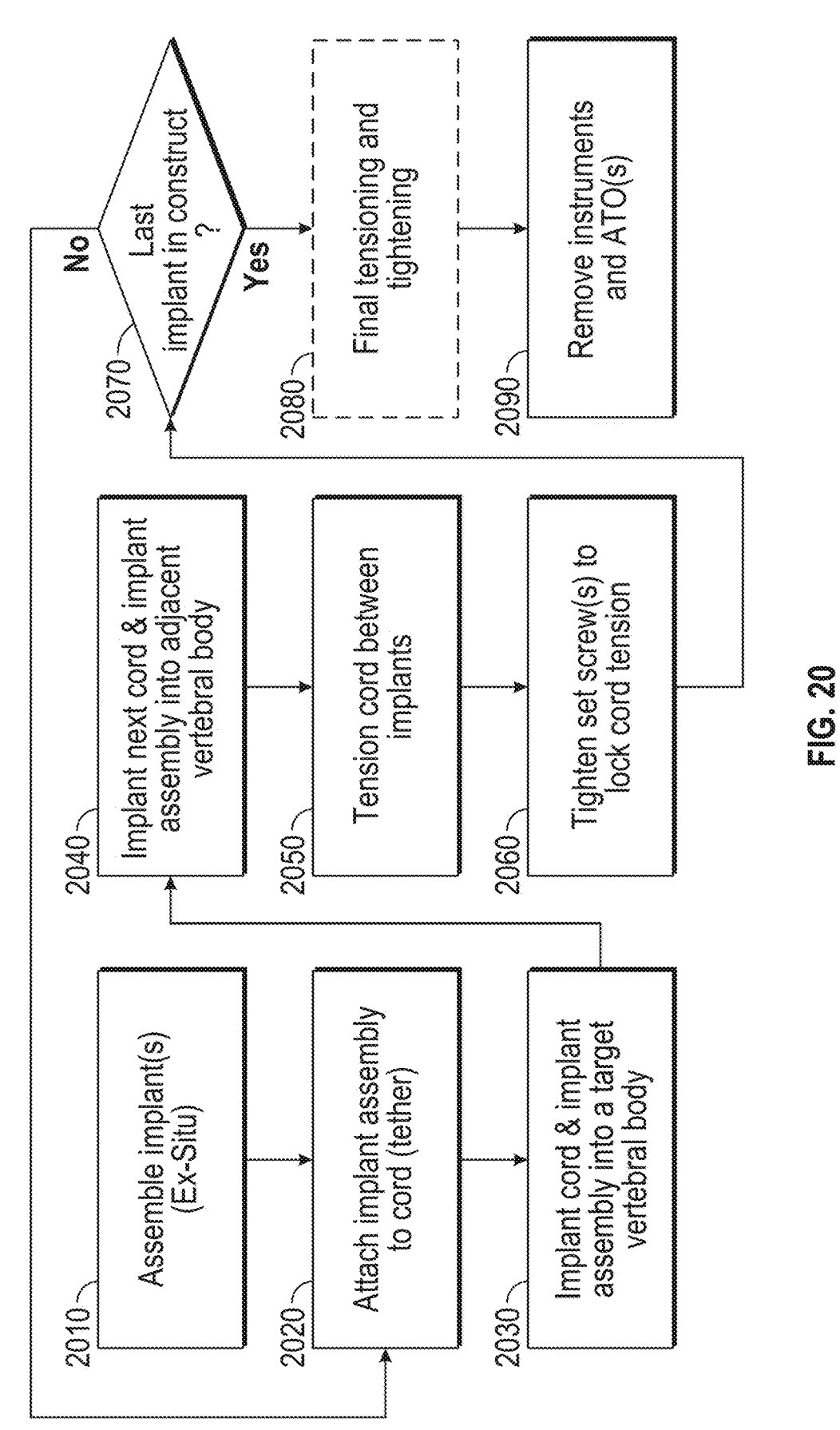
FIG. 20 is a flowchart illustrating a technique for using fully assembled implants in a spinal tethering procedure in accordance with the present disclosure.
Figures 21A, 21B, 21C:
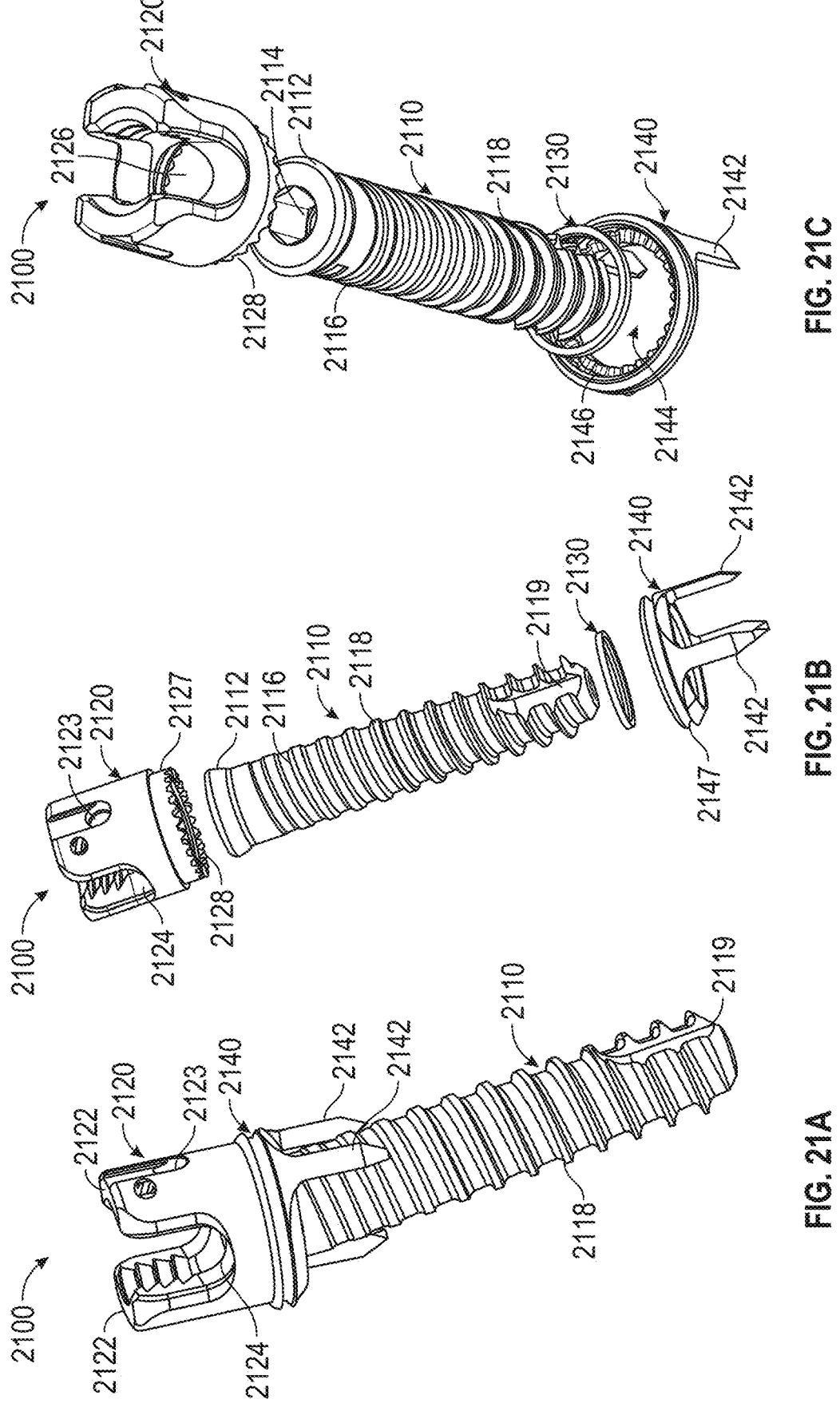
FIGS. 21A-21E are various views of a ploy-axial screw and bone anchor assembly in accordance with the present disclosure.
Figure 21E:
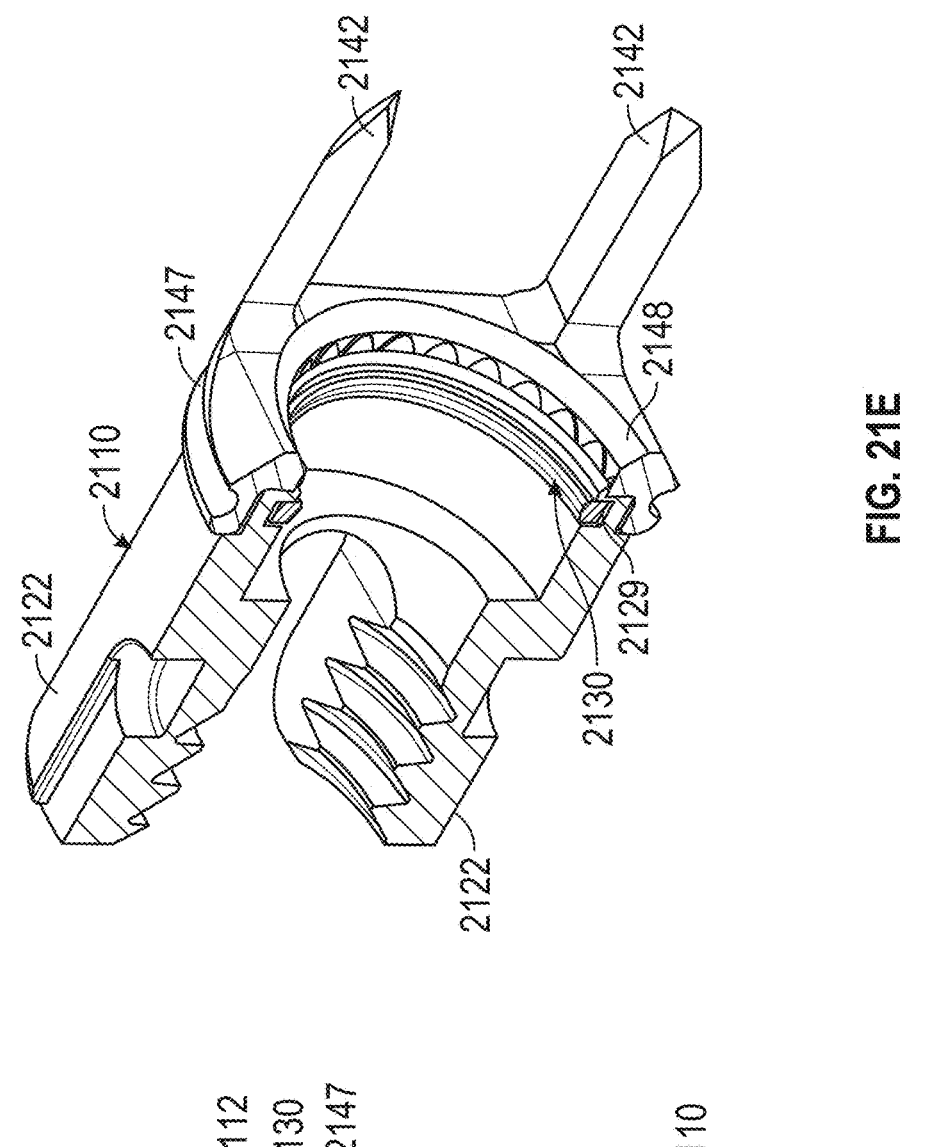
Figure 21D:
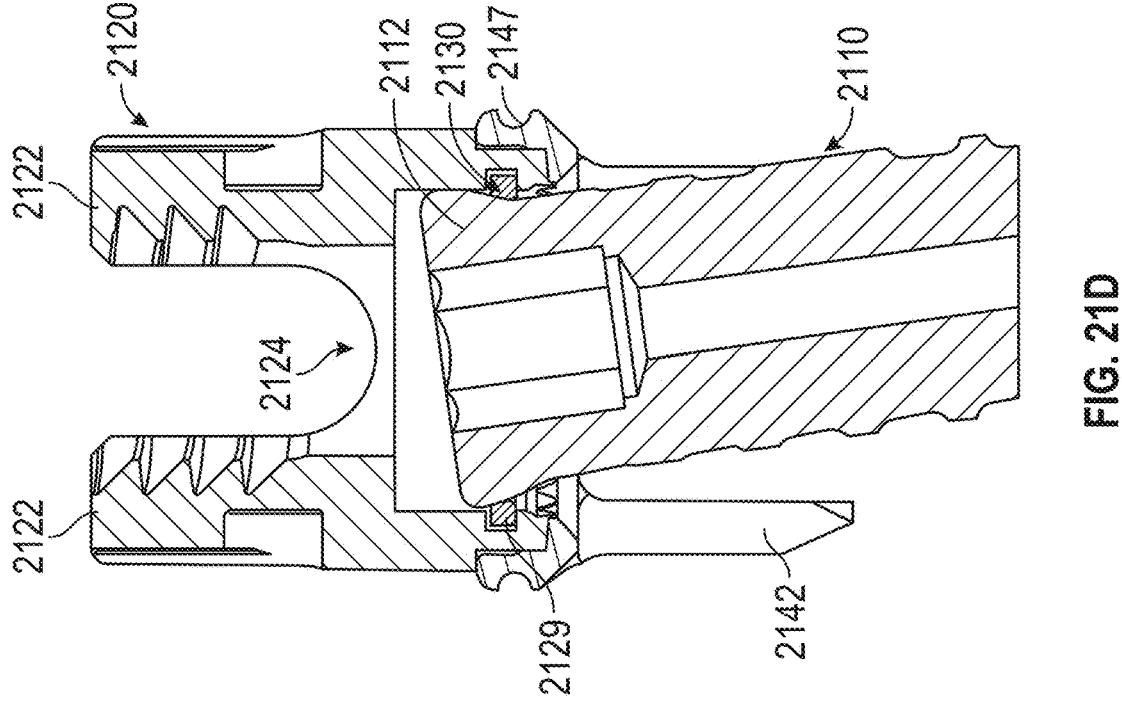

FIG. 20 is a flowchart illustrating a technique 2000 for using fully assembled implants in a spinal tethering procedure. Several of the implants discussed above are usable in the technique 2000, such as implants 1000, 1200, and 1300 in particular. The technique 2000 is discussed below in reference to implant 1000, and more specifically in reference to offset cord clamp 1010. The fully assembled implant technique involves fully assembling the implant onto the cord ex situ, then the cord with the implant(s) are inserted through an ATO and implanted in the target vertebral body. The fully assembled implants may all be put on the cord all at once or may be assembled onto the cord one by one as they are implanted.

In this example, the technique 2000 can begin at 2010 with the implants 1000 assembled ex-situ. At 2020, the technique 2000 continues with the surgeon attaching an assembled implant 1000 onto cord 1070. At this operation, a number of implant assemblies 1000 can be attached to the cord 1070, or they can be attached to the cord one-by-one as they are implanted. At 2030, the technique 2000 continues with the surgeon passing the implant 1000 and the cord 1070 through an ATO and implanting the implant 1000 into a target vertebral body. Next, at 2040, the technique 2000 continues with the next implant 1000 and attached cord 1070 being passed into the patient through the ATO and implanted into an adjacent vertebral body. At 2050, the technique 2000 continues with the surgeon using a distraction instrument (or similar cord tensioning device) to tension the cord between the adjacent vertebral bodies. The technique 2000 continues at 2060 with the surgeon locking set screw(s) on the implants 1000 to retain cord tension induced by the tensioning instrument. At 2070, the technique 2000 continues with the surgeon determining whether the last implant in the construct has been implanted. If there are more implants, the technique 2000 continues back through operations 2020 through 2060 on the next level in the spinal tether construct. Once all implants 1000 have been implanted and tensioned at least initially, the technique 2000 continues with optional operation 2080 where the surgeon can adjust the cord tension with final tensioning and tightening of set screws. At 2090, the technique 2000 completes with all instruments and ATOs being removed from the patient.

FIGS. 21A-21E are various views of implant 2100 that includes a ploy-axial bone screw 2110, a saddle body 2120, and an anchor 2140. The implant 2100 is designed to be implanted as a complete assembly and then have a cord or tether implanted afterward. The bone screw 2110 can include a screw head 2112 and a screw shaft 2116. The screw head 2112 includes a driver interface 2114, while the screw shaft 2116 includes screw threads 2118 and cutting flutes 2119. The saddle body 2120 can include opposing threaded saddle arms 2122 with a cord recess 2124 in between. The saddle body 2120 can also include a screw passage 2126 formed in a lower cylindrical body portion of the saddle body 2120. The lower cylindrical body can also include an inferior cylindrical recess 2127 and an inferior ring gear 2128 around a distal circumference. Within the screw passage 2126, the saddle body 2120 also includes a snap ring groove 2129 to receive a snap ring 2130 that retains the bone screw 2110 once assembled. The anchor 2140 can include anchor spikes 2142 extending inferiorly opposite a superior toothed surface 2146 designed to interface with the inferior ring gear 2129 on the saddle body 2120. Around the superior toothed surface 2146 is a superior cylindrical sidewall 1247 that fits into the inferior cylindrical recess 2127 on the saddle body 2120. Around a distal circumference edge of the anchor 2140 is a chamfered interior edge 2148 that allows for greater angulation of the bone screw 2110. The anchor 2140 may also include other structural features discussed above in reference to other similar anchors.

The implant 2100 can be assembled by inserting the screw head 2112 of the bone screw 2110 into the distal end of the screw passage 2126 of the saddle body 2120. With the screw head 2112 pushed into the saddle body 2120, the snap ring 2130 is inserted into the snap ring groove 2129 to retain the bone screw 2110 within the saddle body 2120. The anchor 2140 can be slid over the distal end of the bone screw 2120 and positioned around the distal end of the saddle body 2120 prior to implantation. Alternatively, the anchor 2140 can be implanted in the target vertebral body, and then the bone screw and saddle body assembly can be implanted through the anchor 2140.

FIGS. 22A-22E are various views of implant 2200 that includes an expanding bone anchor 2210. In this example, the tapered bone anchor 2210 is implanted into a target vertebral body and then saddle insert 2230 is inserted into the tapered bone anchor 2210 to cause expansion of the external threads 2212 along the expansion slots 2214. The purpose of implant 2200 is to enhance the holding strength of a uni-cortical bone screw construct. In currently available spinal tethering systems bi-cortical bone screws are typically used to ensure sufficient holding and avoid screw plow from cord tension. Bi-cortical screws require additional caution during implantation to avoid disturbing soft tissues on the far side of the target vertebral body. Bi-cortical screws are passed through the far cortical bone surface blindly, which can result in negative outcomes in rare instances. Accordingly, the implant 2200 is designed for uni-cortical implantation with the implant only being implanted through the near cortical bone surface and into the cancellous bone within the vertebral body. The expansion of the tapered bone anchor 2210 provides the additional strength instead of passing through the far layer of cortical bone.

In this example, the implant 2200 can include a tapered bone anchor 2210 and a saddle insert 2230. The tapered bone anchor 2210 can include external threads 2212 broken by expansion slots 2214 distributed around the circumference. The bone anchor 2210 can also include an instrument interface 2216 to assist with implanting the bone anchor 2210. Internal features of the bone anchor 2210 can include a saddle funnel 2218 to receive a lower surface of the saddle insert 2230, a central threaded bore 2220, and a tapered internal bore 2222. The saddle insert 2230 can include a saddle body 2232 with opposing threaded saddle arms 2234. The saddle body 2232 can include instrument interfaces 2236, instrument grooves as well as a cord recess 2238 from by the opposing threaded saddle arms 2234. Below the saddle body 2232, the saddle insert 2230 includes a central bore 2240, a threaded anchor interface 2244, and an expansion peg 2246.

Figure 22C:
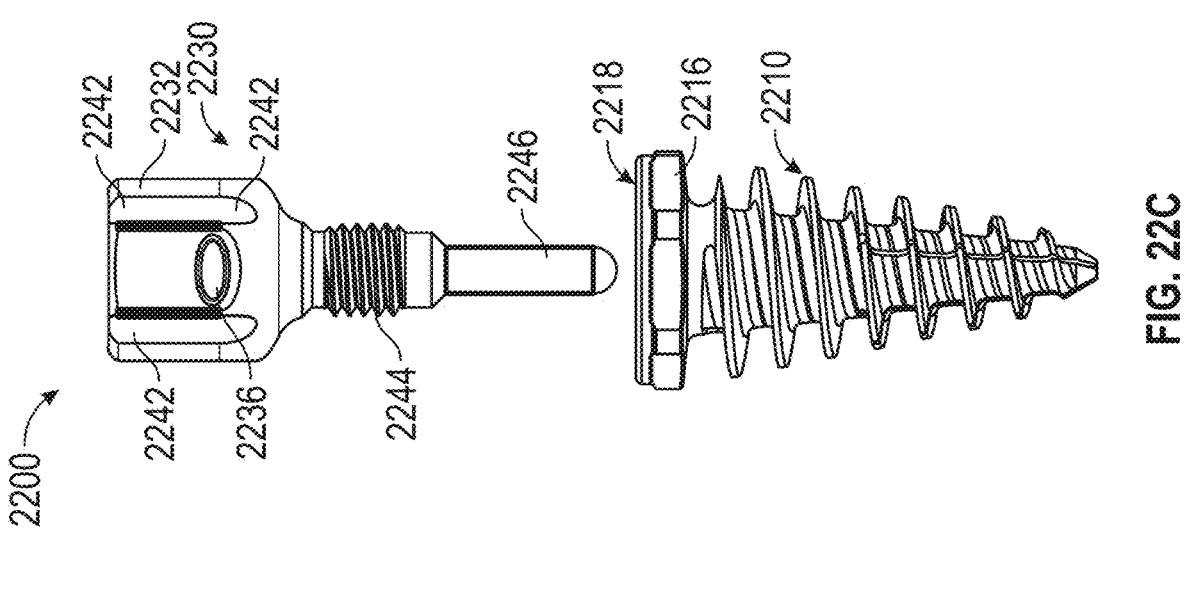
FIGS. 22A-22E are various views of an expanding bone anchor in accordance with the present disclosure.
Figure 22B:
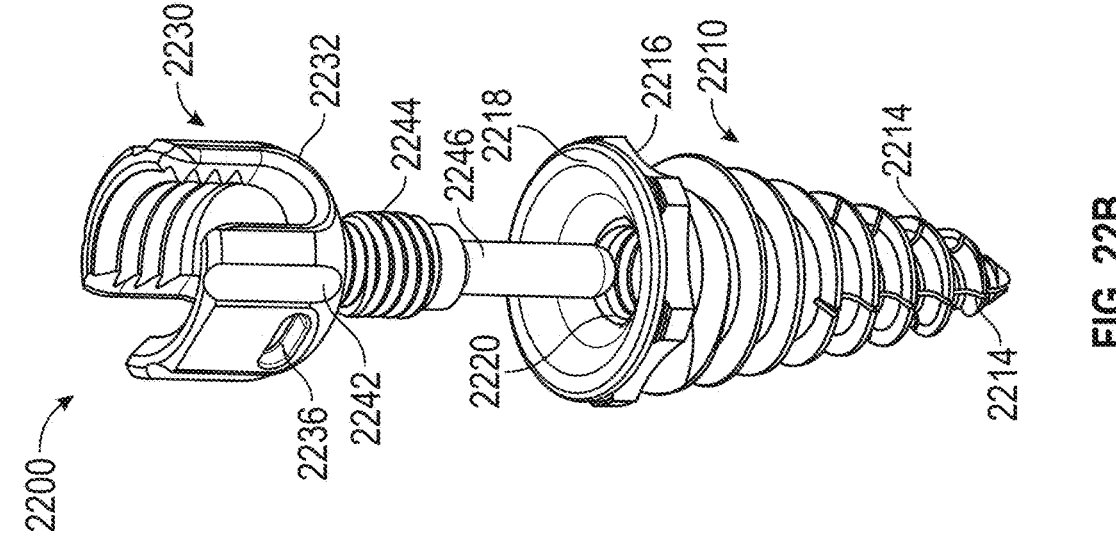
Figure 22A:
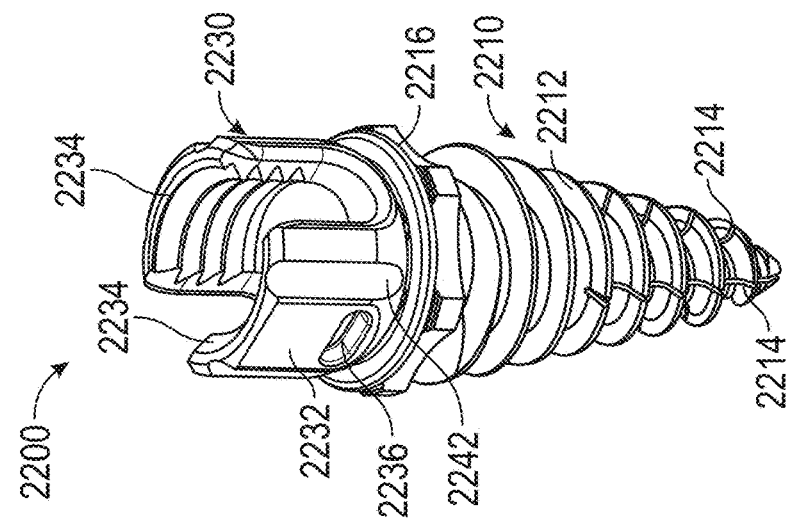
Figures 22D, 22E:
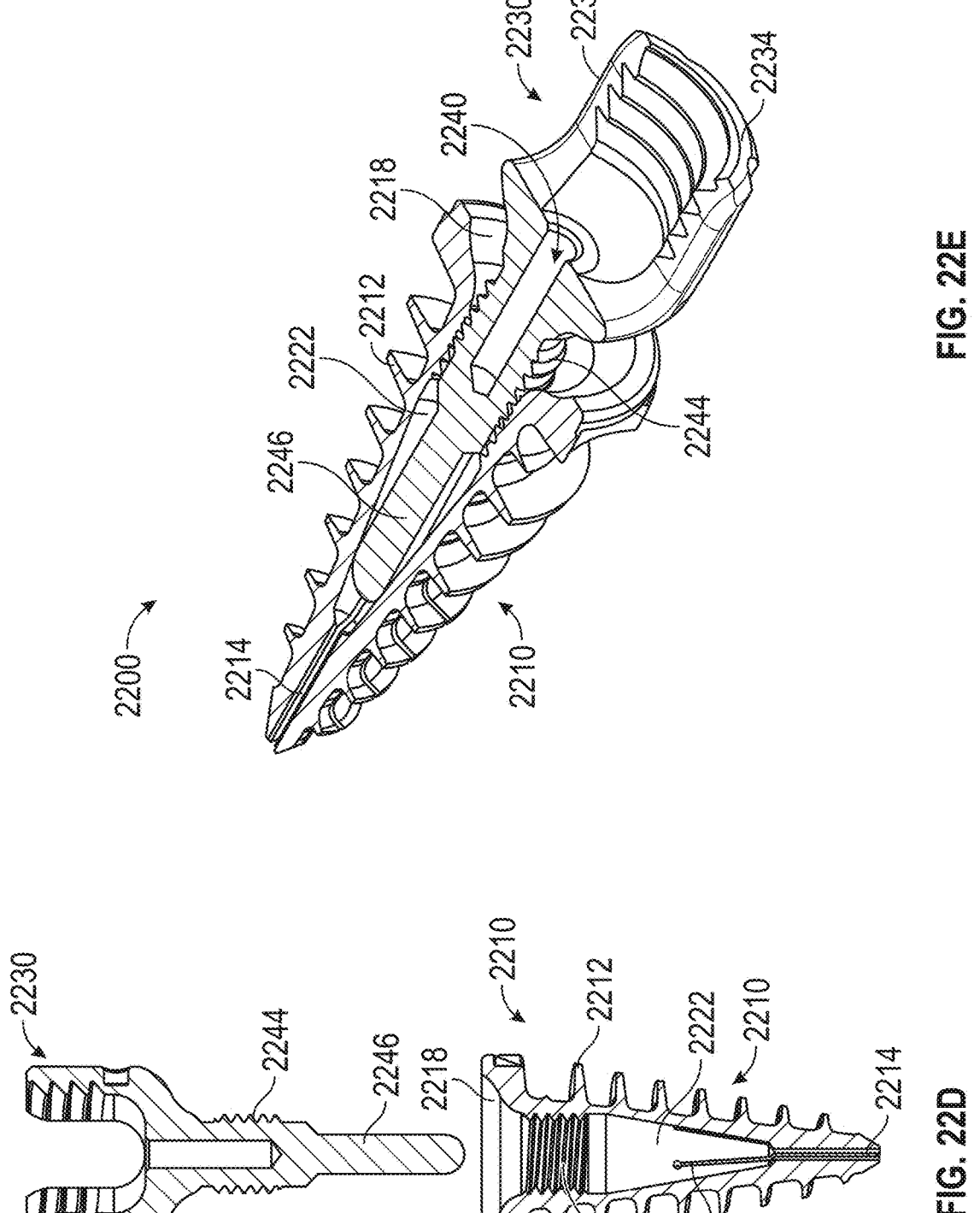
Figures 23A, 23B, 23C, 23D:
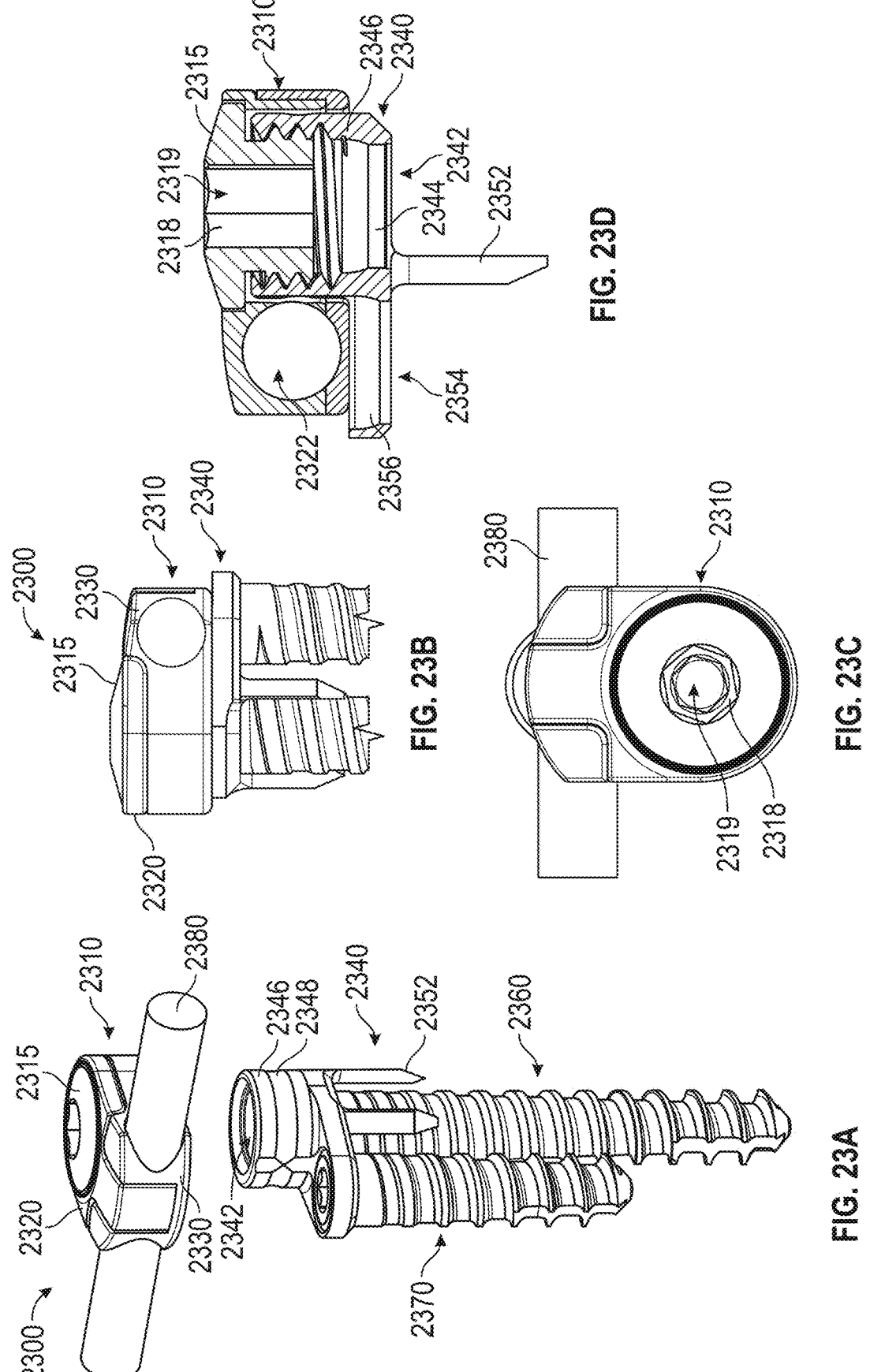
FIGS. 23A-23G are various views of an offset single cord clamp with dual bone screws in accordance with the present disclosure.
Figures 23E, 23F, 23G:
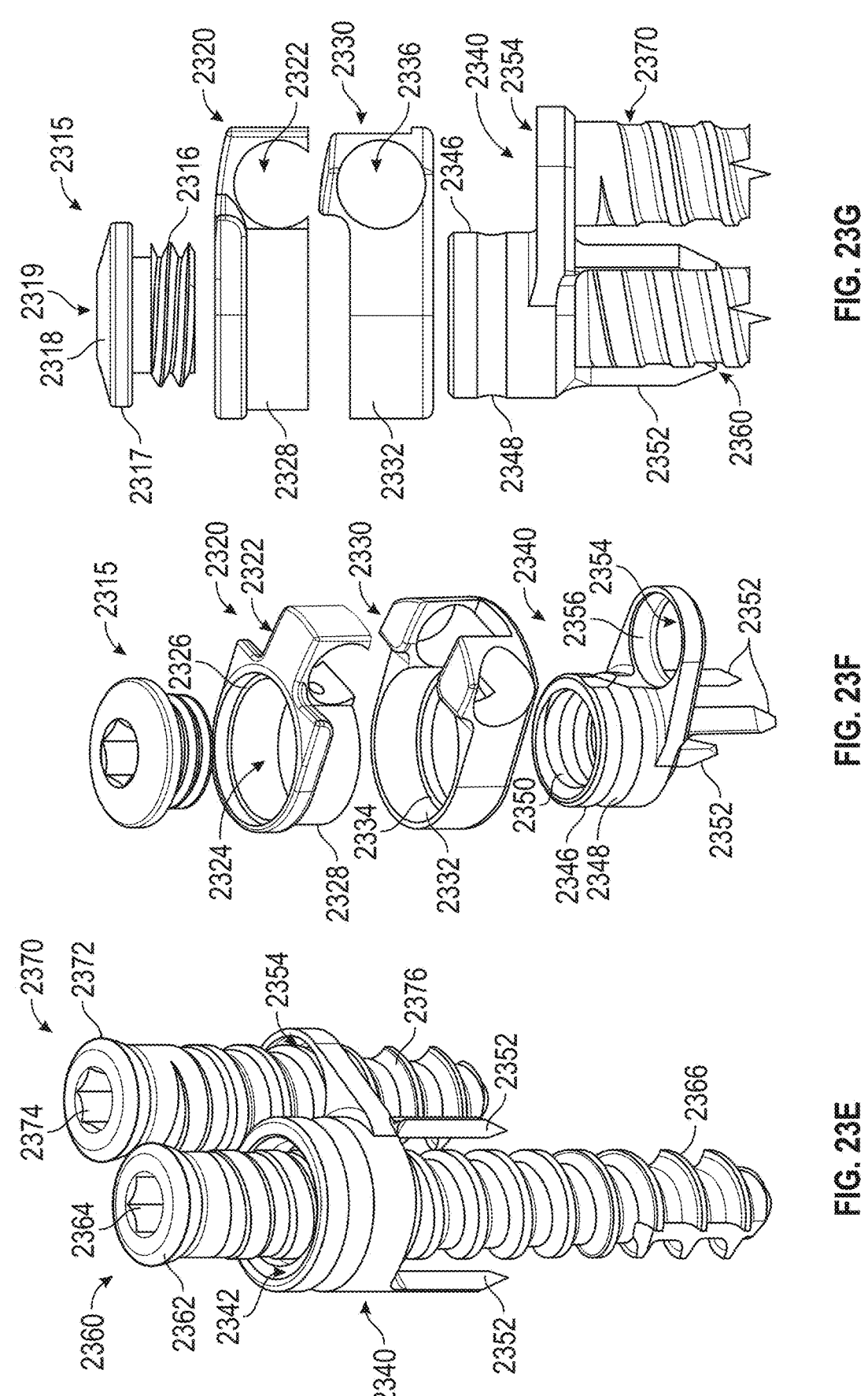

Once the bone anchor 2210 is implanted into a vertebral body, the saddle insert 2230 can be inserted into the central threaded bore 2220. As the threaded anchor interface 2244 engages the central threaded bore 2220, the expansion peg 2246 extends into the tapered internal bore 2222 and pushes the lower portion of the external threads outward expanding the expansion slots 2214. FIG. 22E illustrates the point at which, in this example, the expansion peg 2246 begins to expand the bone anchor 2210. In some examples, the expansion peg 2246 is long enough to extend pass the end of the tapered internal bore 2222 to cause maximum expansion.

The implant 2200 is designed for potential use with cord assemblies discussed above, such as cord assemblies 1450, 1630 or 1720. The implant 220 includes a tulip-style saddle body 2232 that could be adapted for use with any of the noted cord assemblies. In another example, the saddle body 2232 of saddle insert 2230 could be replaced with a threaded post head to allow for a cord assembly, such as cord assembly 1530, to be used with the expanding bone anchor 2210.

FIGS. 23A-23G are various views of an offset single cord clamp 2310 with dual bone screws in accordance with the present disclosure. The cord clamp illustrated in these figures is similar to those discussed above in reference to FIGS. 10A-13F, but includes a two-piece clamp housing (e.g., upper clamp member 2320 and lower clamp member 2330). The two-piece clamp housing enables the cord clamp to be affixed onto the cord prior to implantation by snapping the upper clamp member 2320 into the lower clamp member 2330 and threading the cord 2380 through the cord passages 2322 and 2336—no other structures are required to hold the offset cord clamp 2310 onto the cord 2380 prior to implantation. The offset cord clamp 2310 is illustrated as including dual bone screws (e.g., first bone screw 2360 and second bone screw 2370), but could be modified to use a single bone screw (similar to offset cord clamp 1010). Additionally, the offset cord clamp 2310 attaches to a single cord, but could be modified to clamp two cords (offset or symmetric configurations illustrated above). Accordingly, any of the cord clamp designs illustrated in FIGS. 10A-13F above can be modified to use a similar two-piece housing.

In this example, the implant 2300 includes an offset cord clamp 2310 couplable to a cord 2380 and anchor 2340. The anchor 2340 is designed to receive a first bone screw 2360 and a second bone screw 2370. As noted above, the offset cord clamp 2310 includes an upper clamp member 2320 couplable to a lower clamp member 2330. The upper clamp member 2320 includes a cord passage 2322, a screw passage 2324, a set screw lip 2326 and a cylindrical body 2328. The lower clamp member 2330 includes a receiver cylinder 2332 that receives the cylindrical body 2328. The lower clamp member 2330 also includes an internal lip 2334 and a cord passage 2336. The cord passage 2322 and the cord passage 2336 operate together to couple the offset cord clamp 2310 onto the cord 2380. Once fully assembled in-situ, the set screw 2315 engages the set screw lip 2326 and internal threads 2350 of the anchor 2340 to compress the upper clamp member 2320 into the lower clamp member 2330. Compressing the upper clamp member 2320 and lower clamp member 2330 generates a clamping force throughout the cord passage 2322 and cord passage 2336 to lock the cord in position relative to the offset cord clamp 2310.

In this example, the set screw 2315 includes set screw threads 2316, a set screw head 2317, a driver interface 2318, and an instrument bore 2319. The set screw threads 2316 engage with the internal threads 2350 within the cylindrical body 2346 of the anchor 2340. The set screw head 2317 engages with the set screw lip 2326 within the cylindrical body 2328 of the upper clamp member 2320. The instrument bore 2319 is designed to allow a bone screwdriver to engage with the driver interface 2364 in the first screw head 2362 of the first bone screw 2360.

The anchor in this example, anchor 2340, includes a first screw passage 2342 and a second screw passage 2354 to accommodate dual bone screws. The dual bone screws are intended to increase the holding strength while avoiding bi-cortical screws. The anchor 2340 also includes a first screw seat 2344 and a second screw seat 2356 that are designed to engage with the first screw head 2362 and the second screw head 2372, respectively. The anchor 2340 also includes a cylindrical body 2346 with an external cord groove 2348 and internal threads 2350. The cord groove 2348 is designed to abut a portion of the cord 2380 when the entire implant 2300 is assembled. Anchor spikes 2352 extend inferiorly from the bottom side of the anchor 2340. The anchor spikes 2352 are designed to be embedded into the near cortical bone of the vertebral body to further enhance the strength of implant 2300.

Each of the dual bone screws include screw heads with a flared outer surface that interfaces with the screw seats (2344, 2356) in the anchor 2340. The first bone screw 2360 includes a first screw head 2362, a driver interface 2364, and threads 2366. The second bone screw 2370 includes a second screw head 2372, a driver interface 2374, and threads 2376. In this example, the second bone screw 2370 is smaller than the first bone screw 2360, but the anchor 2340 could be adapted for use with any combination of bone screw sizes.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b) at the time of filing this application, to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. The Abstract is provided to comply with 37 C.F.R. § 1.72 (b), to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment.

What is claimed is:

1. A spinal tethering system comprising:
a flexible elongate cord; and
a plurality of vertebral implants connecting the flexible elongate cord across at least two spinal levels, each vertebral implant of the plurality of vertebral implants comprising:
a fastener including a shank at a distal end and a saddle at a proximal end, the shank operable to be inserted into a respective vertebral body, the saddle operable to receive the flexible elongate cord;
a cord clamp insertable into a proximal end of the saddle after insertion of the flexible elongate cord, the cord clamp comprising:
a first surface; and
an inferior surface opposite the first surface;
wherein a bore extends between the first surface and the inferior surface; and
wherein the cord clamp and the saddle define a cord recess for the flexible elongate cord; and
a set screw operable to engage the cord clamp to secure the flexible elongate cord within the cord recess, the set screw comprising an extension extending from a surface of the set screw;
wherein the set screw extends through the bore and beyond the inferior surface when the set screw is engaged with the cord clamp.

2. The spinal tethering system of claim 1, wherein the saddle comprises a first saddle arm and a second opposing saddle arm.

3. The spinal tethering system of claim 2, wherein the cord clamp is insertable within a saddle cavity defined by the first saddle arm and the second opposing saddle arm and, when the cord clamp is inserted into the proximal end of the saddle, the inferior surface of the cord clamp and a surface of the saddle within the saddle cavity define the cord recess for the flexible elongate cord.

4. The spinal tethering system of claim 2, wherein the cord clamp is engaged with at least one surface of the first saddle arm and the second opposing saddle arm when the flexible elongate cord is secured within the cord recess.

5. The spinal tethering system of claim 1, wherein the cord clamp includes at least one clamp extension to increase an amount of contact area between the cord clamp and the flexible elongate cord when the flexible elongate cord is secured within the cord recess.

6. The spinal tethering system of claim 1, wherein the saddle includes at least one instrument groove on an exterior surface.

7. The spinal tethering system of claim 1, wherein the set screw engages the saddle when the flexible elongate cord is secured within the cord recess.

8. The spinal tethering system of claim 1, wherein an outer portion of the set screw comprises an arcuate structure to linearly displace the set screw in response to set screw rotation.

9. The spinal tethering system of claim 8, wherein the arcuate structure comprises a helical thread extending around at least a portion of a periphery of the set screw.

10. The spinal tethering system of claim 1, each vertebral implant of the plurality of vertebral implants comprising an anchor operable to be inserted into the respective vertebral body, wherein each respective anchor includes a central screw passage operable to receive the corresponding respective fastener prior to insertion of the respective fastener into the respective vertebral body.

11. The spinal tethering system of claim 10, wherein the anchor includes a plurality of spikes extending inferiorly from a periphery of a cylindrical anchor body.

12. The spinal tethering system of claim 11, wherein each spike of the plurality of spikes includes a chisel tip and a retention feature.

13. The spinal tethering system of claim 1, wherein the saddle of each vertebral implant of the plurality of vertebral implants is a dynamic head configured to share cord tension within the flexible elongate cord by releasing a first tension generated at a first spinal level between a first set of vertebral implants of the plurality of vertebral implants to generate a second tension at a second spinal level between a second set of vertebral implants of the plurality of vertebral implants, wherein the second tension is lower than the first tension.

14. The spinal tethering system of claim 13, wherein the dynamic head of each vertebral implant is configured to allow the flexible elongate cord to slip when a cord tension applied to the flexible elongate cord transgresses the first tension.

15. A spinal tethering system comprising:
a flexible elongate cord; and
a first vertebral implant, a second vertebral implant, and a third vertebral implant, each of the first vertebral implant, the second vertebral implant, and the third vertebral implant comprising:

an anchor insertable within a respective vertebral body;

a fastener including a shank at a distal end that is insertable into the respective vertebral body through a central passage within the anchor, the fastener including a saddle at a proximal end; and an assembly comprising a cord clamp and a set screw, the cord clamp comprising a clamp extension extending beyond the saddle when the cord clamp is secured within a cord recess;

wherein the cord clamp is insertable into a proximal end of the saddle;

wherein the cord clamp and the saddle define the cord recess for the flexible elongate cord; and wherein the set screw is operable to secure the flexible elongate cord within the cord recess.

16. The spinal tethering system of claim 15, wherein the cord clamp is engaged with at least one surface of the saddle when the flexible elongate cord is secured within the cord recess.

17. The spinal tethering system of claim 15, wherein the cord clamp is dimensioned to receive a portion of the set screw when the flexible elongate cord is secured within the cord recess.

18. The spinal tethering system of claim 15, wherein the set screw engages the saddle when the flexible elongate cord is secured within the cord recess.

19. A spinal tethering system comprising:

a plurality of vertebral implants, each vertebral implant of the plurality of vertebral implants implantable into a lateral portion of a respective vertebral body, each vertebral implant of the plurality of vertebral implants comprising:

a fastener including a shank at a distal end and a saddle at a proximal end, the shank operable to be inserted into a respective vertebral body, the saddle including a first saddle arm and a second opposing saddle arm;

a cord clamp insertable into a proximal end of the saddle, wherein the cord clamp, the first saddle arm, and the second opposing saddle arm define a cord recess operable to receive a flexible elongate cord; and a set screw operable to secure the flexible elongate cord, once received, within the cord recess;

wherein the cord clamp is engaged with at least one surface of the first saddle arm and the second opposing saddle arm when the flexible elongate cord is secured within the cord recess;

wherein a bore of the cord clamp extends between a first surface of the cord clamp and a second surface of the cord clamp, the bore is dimensioned to receive an extension of the set screw when the flexible elongate cord is secured within the cord recess; and wherein the extension extends through the bore and beyond the second surface when the flexible elongate cord is secured within the cord recess.

20. The spinal tethering system of claim 19, wherein the cord clamp comprises a pair of clamp extensions extending beyond the saddle when the cord clamp is secured within the cord recess.

* * * * *